US012638448B2

(12) United States Patent
Mahler et al.

(10) Patent No.: US 12,638,448 B2
(45) Date of Patent: May 26, 2026

(54) COMPOSITIONS, METHODS, AND KITS FOR DETECTION OF LIPOLYTIC ACTIVITY

(71) Applicant: LONZA LTD, Visp (CH)

(72) Inventors: Hanns-Christian Mahler, Loerrach (DE); Filip Fedorowicz, Jette (BE); Michael Jahn, Loerrach (DE); Andreas Zerr, Basel (CH); Atanas Koulov, Basel (CH)

(73) Assignee: LONZA LTD, Visp (CH)

( * ) Notice: Subject to any disclaimer, the term of this patent is extended or adjusted under 35 U.S.C. 154(b) by 1173 days.

(21) Appl. No.: 17/016,098

(22) Filed: Sep. 9, 2020

(65) Prior Publication Data

US 2021/0096130 A1 Apr. 1, 2021

Related U.S. Application Data

(60) Provisional application No. 62/964,938, filed on Jan. 23, 2020, provisional application No. 62/905,926, filed on Sep. 25, 2019, provisional application No. 62/899,638, filed on Sep. 12, 2019.

(51) Int. Cl.
*G01N 33/573* (2006.01)
*A61K 39/00* (2006.01)
*G01N 21/64* (2006.01)

(52) U.S. Cl.
CPC .......... *G01N 33/573* (2013.01); *A61K 39/00* (2013.01); *G01N 21/6428* (2013.01)

(58) Field of Classification Search
CPC .. G01N 33/573; G01N 21/6428; A61K 39/00; C12Q 1/44; C12Q 1/34
See application file for complete search history.

(56) References Cited

FOREIGN PATENT DOCUMENTS

| | | | | |
|---|---|---|---|---|
| CN | 105039496 A | * 11/2015 | | C12Q 1/44 |
| JP | 2001-333789 A | 12/2001 | | |
| JP | 2017-025017 A | 2/2017 | | |
| WO | 2016/138467 A1 | 9/2016 | | |

OTHER PUBLICATIONS

Iglesias et al. Simplified assays of lipolysis enzymes for drug discovery and specificity assessment of known inhibitors. J. Lipid Res. 2016;57:131-141.*
Ogawa et al. Lactobacillus gasseri SBT2055 suppresses fatty acid release through enlargement of fat emulsion size in vitro and promotes fecal fat excretion in healthy Japanese subjects. Lipids in Health and Disease. 2015; 14(20):1-10.*
Bondos et al. Detection and prevention of protein aggregation before, during, and after purification. Analytical Biochemistry. 2003; 316:223-231.*
Roberts CJ. Protein Aggregation and Its Impact on Product Quality. Curr Opin Biotechnol. 2014;0:211-217.*
Gupta P. To Study the Effect of pH on Lipase. International Journal of Research & Review. 2018:5(8);174-176.*
Abd-Elkaheem et al., "New Colorimetric Method for Lipases Activity Assay in Microbial Media," Am J Anal Chem, Sep. 2013, 4(9): 442-444.
Agarkhed et al., "Effect of Polysorbate 80 Concentration on Thermal and Photostability of a Monoclonal Antibody," AAPS PharmaSaTech, Mar. 2013, 14(1): 1-9.
Asler et al., "Mass spectrometric evidence of covalently-bound tetrahydrolipstatin at the catalytic serine of Streptomyces rimosus lipase," Biochim Biophys Acta, Feb. 2007, 1770: 163-170.
Barbe et al., "Insights into lid movements of Burkholderia cepacia lipase inferred from molecular dynamics simulations," Proteins Struct Funct Bioinforma, Nov. 2009, 77(3): 509-523.
Bates et al., "Kinetics of hydrolysis of polyoxyethylene (20) sorbitan fatty acid ester surfactants," J Pharm Pharmacol, Jun. 1973, 25(6): 470-477.
Bengtsson et al, "Lipoprotein lipase: mechanism of product inhibition," Eur J Biochem, May 1980, 106(2): 557-562.
Blaffert et al., "Spectroscopic methods for assessing the molecular origins of macroscopic solution properties of highly concentrated liquid protein solutions," Anal Biochem, Sep. 2018, 561-562: 70-88.
Borisov et al., "Toward understanding molecular heterogeneity of polysorbates by application of liquid chromatography-mass spectrometry with computer-aided data analysis," Anal Chem, May 2011, 83(10): 3934-3942.
Brito et al., "Determination of the critical micelle concentration of surfactants using the fluorescent probe N-phenyl-1-naphthylamine," Anal Biochem, Feb. 1986, 152(2): 250-255.
Brocca, "Sequence of the lid affects activity and specificity of Candida rugosa lipase isoenzymes," Protein Sci, Oct. 2003, 12(10): 2312-2319.
Carrière et al., "Inhibition of gastrointestinal lipolysis by Orlistat during digestion of test meals in healthy volunteers," Am J Physiol Gastrointest Liver Physiol, Jul. 2001, 281(1): G16-G28.
Champion et al., "Defining your product profile and maintaining control over it, part 2," Bioprocess Int., 2005, 9: 52-57.
Chiu et al., "Knockout of a Difficult-to-Remove CHO Host Cell Protein, Lipoprotein Lipase, for Improved Polysorbate Stability in Monoclonal Antibody Formulations," Biotechnol Bioeng, May 2017, 114(5): 1006-1015.
Daniel et al., "Lipase-catalyzed esterification of palmarosa oil," Eng Life Sci, May 2010, 11(2): 195-200.
Divakar et al., "A multisubstrate assay for lipases/esterases: Assessing acyl chain length selectivity by reverse-phase high-performance liquid chromatography," Anal Biochem, Mar. 2014, 448: 38-40.
Dixit et al., "Residual Host Cell Protein Promotes Polysorbate 20 Degradation in a Sulfatase Drug Product Leading to Free Fatty Acid Particles," J Pharm Sci, May 2016, 105(5): 1657-1666.

(Continued)

*Primary Examiner* — Lynn Y Fan
(74) *Attorney, Agent, or Firm* — Medler Ferro Woodhouse & Mills PLLC

(57) ABSTRACT

The present disclosure provides compositions, methods, and kits for detecting lipolytic activity. In some embodiments, the composition comprises an aqueous assay sample and an organic solvent, wherein the organic solvent comprises 4-methylumbelliferyl oleate (4MuO). Also provided herein are methods for determining the stability of a protein preparation.

22 Claims, 32 Drawing Sheets

(56) References Cited

OTHER PUBLICATIONS

Donbrow et al., "Development of acidity in non-ionic surfactants: formic and acetic acid," Analyst, 1978, 103(1225): 400-402.
Doshi et al., "Understanding Particle Formation: Solubility of Free Fatty Acids as Polysorbate 20 Degradation Byproducts in Therapeutic Monoclonal Antibody Formulations," Mol Pharmaceutics, Sep. 2015, 12(11): 3792-3804.
Duangjai et al., "Inhibitory effects of Tiliacora triandra (Colebr.) Diels on cholesterol absorption," Journal of Complementary and Integrative Medicine, Oct. 2018, 16(1).
Dwivedi et al., "Polysorbate degradation in biotherapeutic formulations: Identification and discussion of current root causes," Int J Pharm, Dec. 2018, 551(1-2): 422-436.
Edelmann et al., "Instability of Polysorbates in Protein Biopharmaceutics," Presentation at DDF Summit dated Mar. 13, 2019. Retrieved from <https://www.ddfevent.com/media/12216/franziska-edelmann.pdf>.
Elgharbawy et al., "Shedding Light on Lipase Stability in Natural Deep Eutectic Solvents," Chem Biochem Eng Q, Sep. 2018, 32(3): 359-370.
Fischer et al., "Specific immune response to phospholipase B-like 2 protein, a host cell impurity in Lebrikizumab clinical material," AAPS J, Jan. 2017, 19(1): 254-263.
Frikha et al., "Structural Homologies, Importance for Catalysis and Lipid Binding of the N-Terminal Peptide of a Fungal and a Pancreatic Lipase," Protein Pept Lett, Feb. 2010, 17(2): 254-259.
Fukuda et al., "Biodiesel Fuel Production by Transesterification of Oils," J Biosci Bioeng, Jan. 2001, 92(5): 405-416.
Gao, "Fragmentation of a highly purified monoclonal antibody attributed to residual CHO cell protease activity," Biotechno. Bioeng, Apr. 2011, 108(4): 977-982.
Glogauer et al., "Identification and characterization of a new true lipase isolated through metagenomic approach," Microb Cell Fact, Jul. 2011, 10(1): 54.
Gupta et al., "Lipase assays for conventional and molecular screening: an overview," Feb. 2003, 37(1): 63-71.
Gupta et al., "Simplified para-nitrophenyl palmitate assay for lipases and esterases," Anal Biochem, Dec. 2002, 311(1): 98-99.
Ha et al., "Peroxide formation in polysorbate 80 and protein stability," J Pharm Sci, Oct. 2002, 91(10): 2252-2264.
Hadváry et al., "The Lipase Inhibitor Tetrahydrolipstatin Binds Covalently to the Putative Active Site Serine of Pancreatic Lipase," J Biol Chem, 1991, 266(4): 2021-2027.
Hall et al., "Polysorbates 20 and 80 Degradation by Group XV Lysosomal Phospholipase A2 Isomer X1 in Monoclonal Antibody Formulations," J Pharm Sci, May 2016, 105(5): 1633-1642.
Han et al., "Anti-obesity effects in rodents of dietary teasaponin a lipase inhibitor," Int J Obesity, Oct. 2001, 25: 1459-1464.
Harrabi et al., "Polysaccharides extraction from Opuntia stricta and their protective effect against HepG2 cell death and hypolipidaemic effects on hyperlipidaemia rats induced by high-fat diet," Arch Physiol Biochem, Oct. 2017, 123(4): 225-237.
Hasan et al., "Methods for detection and characterization of lipases: A comprehensive review," Biotechnology Advances, Jun. 2009, 27(6): 782-798.
Heck et al., "Orlistat, a New Lipase Inhibitor for the Management of Obesity," Pharmacotherapy, Mar. 2000, 20(3): 270-279.
Híreš et al., "Development and Optimization of a High-Throughput Screening Assay for Rapid Evaluation of Lipstatin Production by Streptomyces Strains," Curr Microbiol, Dec. 2017, 75: 580-587.
Hogwood et al., "Host cell protein dynamics in recombinant CHO cells: impacts from harvest to purification and beyond," Bioengineered, Sep. 2013, 4(5): 288-291.
Hvattum et al., "Characterization of polysorbate 80 with liquid chromatography mass spectrometry and nuclear magnetic resonance spectroscopy: specific determination of oxidation products of thermally oxidized polysorbate 80," J Pharm Biomed Anal, Mar. 2012, 62: 7-16.
Jahn, Michael et al., "Measuring Lipolytic Activity to Support Process Improvements to Manage Lipase-Mediated Polysorbate Degradation," Pharm Res, Jun. 2020, 37: 118.
Jette et. al, "Determination of Lipase Activity by a Rhodamine-Triglyceride-Agarose Assay," Anal Biochem, Jun. 1994, 219(2): 256-260.
Johnson et al., "The original Michaelis constant: translation of the 1913 Michaelis-Menten paper," Biochemistry, Oct. 2011, 50(39): 8264-8269.
Jones et al., "Effect of neutral and acid pH on the fluorescence of 4-methylumbelliferone and the implications for dry blood spot assays," Mol Genet Metab, Jan. 2013, 108(2): S51.
Jones et al., "Considerations for the Use of Polysorbates in Biopharmaceuticals," Pharm Res, May 2018, 35(8): 148.
Kerwin et al., "Polysorbates 20 and 80 used in the formulation of protein biotherapeutics: structure and degradation pathways," J Pharm Sci, Aug. 2008, 97(8): 2924-2935.
Khan et al., "The Lid Domain in Lipases: Structural and Functional Determinant of Enzymatic Properties," Front Bioeng Biotechnol, Mar. 2017, 5: Article 16.
Khan, Tarik A. et al., "Key interactions of surfactants in therapeutic protein formulations: A review," Eur J Pharm Biopharm, Nov. 2015, vol. 97, Pt A, pp. 60-67.
Khossravi et al., "Analysis Methods of Polysorbate 20: A New Method to Assess the Stability of Polysorbate 20 and Established Methods that May Overlook Degraded Polysorbate 20," Pharm Res, May 2002, 19(5): 634-635.
Kiese et al., "Shaken, Not Stirred: Mechanical Stress Testing of an IgG1 Antibody," J Pharm Sci, Oct. 2008, 97(10): 4347-4366.
Kishore et al., "The Degradation of Polysorbates 20 and 80 and its Potential Impact on the Stability of Biotherapeutics," Pharm Res, Mar. 2011, 28: 1194-1210.
Kishore et al., "Degradation of polysorbates 20 and 80: studies on thermal autoxidation and hydrolysis," J Pharm Sci, Feb. 2011, 100(2): 721-731.
Kiyotani et al., "Measurement of Lipase Activity of Guinea Pig Peritoneal Macrophages with 4-Methyl-umbelliferyl-oleate," Hiroshima J Med Sci, Mar. 1983, 32(1): 15-18.
Konarzycka-Bessler et al., "A High-Throughput-Screening Method for Determining the Synthetic Activity of Hydrolases," Angew Chem Int Ed, Mar. 2003, 42(12): 1418-1420.
Koster et al., "Study of the hydrolysis of 4-methylumbelliferyl oleate by acid lipase and cholesteryl oleate by acid cholesteryl esterase in human leucocytes, fibroblasts and liver," Biochim Biophys Acta, 1980, 618: 98-105.
Kranz et al., "Factors Influencing Polysorbate's Sensitivity Against Enzymatic Hydrolysis and Oxidative Degradation," J Pharm Sci, Jun. 2019, 108(6): 2022-2032.
Kurihara et al., "Hypolipemic Effect of Cyclocarya paliurus (Batal) Iljinskaja in Lipid-Loaded Mice," Biol Pharm Bull, Mar. 2003, 26(3): 383-385.
Kuroda et al., "Sesquiterpene farnesol as a competitive inhibitor of lipase activity of *Staphylococcus aureus*," FEMS Microbiol Lett, Aug. 2007, 273(1): 28-34.
Labrenz, "Ester Hydrolysis of Polysorbate 80 in mAb Drug Product: Evidence in Support of the Hypothesized Risk After the Observation of Visible Particulate in mAb Formulations," J Pharm Sci, Aug. 2014, 103(8): 2268-2277.
Labrenz, "Lipase Hydrolysis of PS80 in High Concentration mAb Formulation," Presentation based on J Pharm Sci, Aug. 2014, 103(8): 2268-2277.
Lee et al., "Purification and characterization of Pseudomonas fluorescens SIK W1 lipase expressed in *Escherichia coli*," Biochim Biophys Acta, 1993, 1169(2): 156-164.
Levy et al., "Host Cell Protein Impurities in Chromatographic Polishing Steps for Monoclonal Antibody Purification," Biotechnol Bioeng, Jun. 2016, 113(6): 1260-1272.
Lewis et al., "Direct Measurement of Lipase Inhibition by Orlistat Using a Dissolution Linked In Vitro Assay," Clin Pharmacol Biopharm, 2012, 1(3): 1-3.
Li et al., "Adsorption and catalytic activity of Porcine pancreatic lipase on rod-like SBA-15 mesoporous material," Colloids and Surfaces A: Physicochem Eng Aspects, Jun. 2009, 341: 79-85.

(56) References Cited

OTHER PUBLICATIONS

Li et al., "Characterization and stability study of polysorbate 20 in therapeutic monoclonal antibody formulation by multidimensional ultrahigh-performance liquid chromatography-charged aerosol detection-mass spectrometry," Anal Chem, Apr. 2014, 86: 5150-5157.
Lippold et al., "Impact of mono- and poly-ester fractions on polysorbate quantitation using mixed-mode HPLC-CAD/ELSD and the fluorescence micelle assay," J Pharm Biomed Anal, Jan. 5, 2017, vol. 132, pp. 24-34.
Lookene et al., "Interactions of lipoprotein lipase with the active-site inhibitor tetrahydrolipstatin (Orlistat)®," Eur J Biochem, 1994, 222(2): 395-403.
Lopes et al., "Lipase and esterase—to what extent can this classification be applied accurately?" Ciênc Tecnol Aliment, Aug. 2011, 31(3): 603-613.
Lowe, "The triglyceride lipases of the pancreas," J Lipid Res, 2002, 43(12): 2007-2016.
Lunagariya et al., "Inhibitors of Pancreatic Lipase: State of the Art and Clinical Perspectives," EXCLI Journal, Aug. 2014, 13: 897-921.
Lüthi-Peng et al., "Identification of the active-site serine in human pancreatic lipase by chemical modification with tetrahydrolipstatin," FEBS Lett, Mar. 1992, 299(1): 111-115.
Mabey et al., "Critical review of hydrolysis of organic compounds in water under environmental conditions," J Phys Chem Ref Data, 1978, 7(2): 383-415.
Mahler et al., "Protein Aggregation: Pathways, Induction Factors and Analysis," J Pharm Sci, Sep. 2009, 98(9): pp. 2909-2934.
Mahler et al., "Adsorption behavior of a surfactant and a monoclonal antibody to sterilizing-grade filters," J Pharm Sci, Jun. 2010, 99(6): 2620-2627.
McShan et al., "Hydrolysis of Polysorbate 20 and 80 by a Range of Carboxylester Hydrolases," Pda J Pharm Sci and Tech, 2016, 70(4): 332-345.
Mittal, "Determination of CMC of polysorbate 20 in aqueous solution by surface tension method," J Pharm Sci, Aug. 1972, 61(8): 1334-1335.
Nakai et al., "Inhibitory Effects of Oolong Tea Polyphenols on Pancreatic Lipase in Vitro," J Agric Food Chem, Jun. 2005, 53(11): 4593-4598.
Philo, "A Critical Review of Methods for Size Characterization of Non-Particulate Protein Aggregates," Curr Pharm Biotechnol, Jun. 2009, 10(4): 359-372.
Podsedek et al., "In Vitro Inhibitory Effect on Digestive Enzymes and Antioxidant Potential of Commonly Consumed Fruits," J Agric Food Chem, May 2014, 62(20): 4610- 4617.
Pohanka et al., "Biosensors and Bioassays Based on Lipases, Principles and Applications, a Review," Molecules, Feb. 2019, 24: 616.
Robert et al., "Degradation of an Fc-fusion recombinant protein by host cell proteases: Identification of a CHO cathepsin D protease," Biotechnol Bioeng, Dec. 2009, 104(6): 1132-1141.
Rosenstein et al., "Staphylococcal lipases: Biochemical and molecular characterization," Biochimie, Nov. 2000, 82(11): 1005-1014.
Saggu et al., "Identification of subvisible particles in biopharmaceutical formulations using Raman spectroscopy provides insight into polysorbate 20 degradation pathway," Pharm Res, Sep. 2015, 32(9): 2877-2888.
Sarda et al., "Action de la lipase pancréatique sur les esters en emulsion," Biochim Biophys Acta, Dec. 1958, 30(3): 513-521.
Shah et al., "Egg Yolk Factor of *Staphylococcus aureus* II. Characterization of the Lipase Activity," J Bacteriol, Apr. 1965, 89(4): 949-953.
Shukla et al., "Downstream processing of monoclonal antibodies—application of platform approaches," J Chromatogr B Analyt Technol Biomed Life Sci, Mar. 2007, 848(1): 28-39.
Šilha et al., "The Hlb number determination of polyoxyethylene surfactants," Collect Czech Chem Commun, 1989, 54(4): 945-952.
Simons et al., "The Lipase from *Staphylococcus aureus*," Eur J Biochem, Dec. 1996, 242(3): 760-769.
Singh et al., "Are Injection Site Reactions in Monoclonal Antibody Therapies Caused by Polysorbate Excipient Degradants?", J Pharm Sci, Nov. 2018, 107(11): 2735-2741.
Stalder et al., "120. Tetrahydrolipstatin: Degradation Products Produced by Human Carboxyl-ester Lipase," Helv Chim Acta, Aug. 1992, 75(5): 1593-1603.
Stoytcheva et al., "Analytical Methods for Lipases Activity Determination: A Review," Curr Anal Chem, 2012, 8(3): 400-407.
Tomlinson et al., "Polysorbate 20 Degradation in Biopharmaceutical Formulations: Quantification of Free Fatty Acids, Characterization of Particulates, and Insights into the Degradation Mechanism," Mol Pharmaceutics, 2015, 12(11): 3805-3815.
Van Tilbeurgh, "Structure of the pancreatic lipase-procolipase complex," Nature, Sep. 1992, 359: 159-162.
Vanderlaan et al., "Hamster Phospholipase B-Like 2 (PLBL2) A Host-Cell Protein Impurity in Therapeutic Monoclonal Antibodies Derived from Chinese Hamster Ovary Cells," BioProcess Int, Mar. 2015, 13(4): 18-29 & 55.
Weibel et al., "Lipstatin, an inhibitor of pancreatic lipase produced by Streptomyces Toxytricini I. Producing organism, fermentation, isolation and biological activity," J Antbiotics, Aug. 1987, 40(8): 1081-1085.
Werner et al., "Anion-Induced Fluorescence Quenching of a New Zwitterionic Biacridine Derivative," Photochem Photobiol, Oct. 1999, 70(4): 585-589.
Winkler et al., "Structure of human pancreatic lipase," Nature, Feb. 1990, 343: 771-774.
Zheng et al., "Fluorescent microplate assay method for high-throughput detection of lipase transesterification activity," Anal Biochem, May 2018, 549: 26-28.
Zhi et al., "Fluorescent Properties of Hymecromone and Fluorimetric Analysis of Hymecromone in Compound Dantong Capsule," J Spectroscop, Dec. 2012, 2013: 147128.
Zottig et al., "Development of a high-throughput liquid state assay for lipase activity using natural substrates and rhodamine B," Anal Biochem, Mar. 2016, 496: 25-29.
International Search Report and Written Opinion in PCT/US2020/049992, mailed Oct. 26, 2020.
Duangjai and Saokaew, "Inhibitory effects of Tiliacora triandra (Colebr.) Diels on cholesterol absorption," Journal of Complementary and Integrative Medicine 16(1): 20170169 (2019).

* cited by examiner

I (pH < 4)

II (pH 4-7)

III (pH 9-12)

IV (pH > 12)

| Specified 4Mu concentration [μM] | Relative fluorescence units (RFU) | Calculated 4Mu concentration [μM] | Recovery [%] |
|---|---|---|---|
| 0.00 | 83135 | Not applicable | Not applicable |
| 0.01 | 376178 | 0.01 | 124 |
| 0.05 | 1511383 | 0.05 | 108 |
| 0.10 | 2738342 | 0.10 | 99 |
| 0.25 | 6534340 | 0.24 | 96 |
| 0.50 | 13763493 | 0.55 | 109 |
| 1.00 | 22688574 | 0.97 | 97 |
| 2.50 | 55708864 | 2.56 | 102 |
| 5.00 | 106213696 | 4.98 | 100 |

FIG. 19B

COMPOSITIONS, METHODS, AND KITS FOR DETECTION OF LIPOLYTIC ACTIVITY

FIELD OF THE INVENTION

The present disclosure provides compositions, methods, and kits for detecting and/or quantifying lipolytic activity. Also provided herein are methods for determining the stability of a protein preparation. In some embodiments, a composition for detecting lipolytic activity comprises an aqueous assay sample and an organic solvent, wherein the organic solvent comprises 4-methylumbelliferyl oleate (4MuO).

BACKGROUND

Cell cultures can be used for the generation of commercially important proteins such as therapeutic proteins. Besides the target protein, the cells produce host cell proteins (HCPs), e.g. lipases, which can be found in the production pools of the target protein, e.g. the cell culture supernatant or cell lysate. The downstream purification process, which can include various chromatography steps (e.g., in the case of monoclonal antibody production, affinity chromatography), are generally capable of depleting the vast majority of the HCPs. Yet, a 100% depletion of HCPs may not be possible due to the natural principles of the separation and purification methods, which are based on equilibria. An HCP limit accepted by industry and health authorities is at ~1-100 ppm, relative to the amount of active protein. HCPs are typically measured and reported as a sum parameter with the aid of enzyme-linked immunosorbent assays (ELISA), as outlined e.g. in USP <1132>, hence, these typically include a range of different host-derived proteins at various concentrations. Drug substances with the same total HCP content as quantified by ELISA, might have different HCP profiles. This might lead to a situation that a slight process variation causes an increase of a low concentrated specific HCP, e.g. a lipase, which might not be detected by application of the total HCP assay. Thus, a small percentage of HCPs may be present in the final protein product and can have catalytic activity. Residual catalytic activity can have detrimental effects on the product quality, such as stability of excipients, e.g. surfactants such as polysorbates, and ultimately the stability, quality, and safety of the protein product. Minimizing or eliminating these detrimental effects can be of utmost importance if the protein is a therapeutic protein, especially a therapeutic protein used in humans.

Residual lipase activity in protein preparation, for example, due to sub-optimal depletion during the downstream purification process of the target protein can lead to hydrolysis of some excipients, e.g., surfactants. The consequences may include, e.g., formation of sub-visible and visible particles due to the release of non-polar, and therefore insoluble, long chain fatty acids and other degradants from the surfactants, and the loss of stabilization provided by the surfactants. Surfactant degradation can also have an adverse impact on protein quality, e.g., producing peroxides leading to protein degradation, or producing lauric acid inducing protein aggregation. Degradation of surfactants also reduces their concentration in the formulation, potentially causing insufficient protection of the protein, e.g., against interfacial stress (e.g., shaking, freezing/thawing and the like), and also lead to potential differences in safety considerations of the product, e.g., different in vivo liabilities due to the degraded surfactant. Thus, residual lipase activity may lead to a compromised quality of the final protein preparation due to the hydrolysis of excipients. Degradation products of excipients such as, e.g., polysorbates, can also cause safety issues in patients, such as injection site reactions (see, e.g., Singh et al., J Pharm Sci 107(11):2735-2741 (2018)).

SUMMARY OF THE INVENTION

In some embodiments, the present disclosure provides a composition comprising: (a) an aqueous assay sample comprising a protein preparation; and (b) an organic solvent, wherein the organic solvent further comprises 4-methylumbelliferyl oleate (4MuO); wherein the aqueous assay sample has a pH of 5.0 to 7.0; and wherein the aqueous assay sample is about 80% to about 99.9% of the composition, and the organic solvent is about 0.1% to about 20% of the composition.

In some embodiments, the protein preparation is a cell culture supernatant. In some embodiments, the protein preparation is a partially purified protein preparation. In some embodiments, the protein preparation is a purified protein preparation.

In some embodiments, the protein preparation comprises a therapeutic protein.

In some embodiments, the protein preparation comprises a surfactant. In some embodiments, the surfactant is a polysorbate. In some embodiments, the polysorbate is polysorbate-20, polysorbate-80 or combinations thereof.

In some embodiments, the protein preparation further comprises additional host cell proteins.

In some embodiments, the aqueous assay sample further comprises a buffering agent, a salt, or both.

In some embodiments, the salt is sodium chloride, calcium chloride or combinations thereof. In some embodiments, the salt is sodium chloride and calcium chloride. In some embodiments, the sodium chloride is about 50 mM to about 400 mM in the aqueous assay sample. In some embodiments, the sodium chloride is about 100 mM to about 200 mM in the aqueous assay sample. In some embodiments, the calcium chloride is about 0.2 mM to about 10 mM in the aqueous assay sample. In some embodiments, the calcium chloride is about 1.0 mM to about 2.0 mM in the aqueous assay sample.

In some embodiments, the buffering agent has a buffering capacity at about pH 6.0. In some embodiments, the buffering agent is Tris. In some embodiments, the buffering agent is Bis-Tris. In some embodiments, the buffering agent is about 2 mM to about 200 mM in the aqueous assay sample. In some embodiments, the buffering agent is about 10 mM to about 100 mM in the aqueous assay sample. In some embodiments, the buffering agent is about 40 mM to about 60 mM in the aqueous assay sample. In some embodiments, the buffering agent is about 45 mM to about 55 mM in the aqueous assay sample.

In some embodiments, the organic solvent is an alcohol, a sulfoxide, a nitrile, or combination thereof. In some embodiments, the organic solvent is dimethyl sulfoxide (DMSO). In some embodiments, the organic solvent comprises acetonitrile.

In some embodiments, the organic solvent comprises an alcohol. In some embodiments, the organic solvent comprises a mixture of acetonitrile and iso-propanol. In some embodiments, the organic solvent is a $C_1$-$C_6$ alcohol. In some embodiments, the organic solvent is methanol, ethanol, propanol, iso-propanol, butanol, sec-butanol, iso-butanol, tert-butanol, or combinations thereof.

In some embodiments, the composition further comprises a lipase inhibitor. In some embodiments, the lipase inhibitor is (S)-2-formylamino-4-methyl-pentanoic acid (S)-1-[[(2S, 3S)-3-hexyl-4-oxo-2-oxetanyl]methyl]-dodecyl ester (orlistat).

In some embodiments, the lipase inhibitor is in the organic solvent. In some embodiments, the lipase inhibitor is about 1 μM to about 50 μM in the composition. In some embodiments, the lipase inhibitor is about 5 μM to about 25 μM in the composition.

In some embodiments, the present disclosure provides a composition comprising: (a) an aqueous assay sample comprising (i) a purified protein preparation; (ii) a buffering agent; and (iii) a salt; and (b) an organic solvent, wherein the organic solvent further comprises 4-methylumbelliferyl oleate (4MuO); wherein the aqueous assay sample has a pH of 5.0 to 7.0; and wherein the aqueous assay sample is about 80% to about 99.9% of the composition, and wherein the organic solvent is about 0.1% to about 20% of the composition.

In some embodiments, the present disclosure provides a composition comprising: (a) about 90% to about 99.9% (vol/vol) of an aqueous assay sample comprising (i) a purified protein preparation comprising a protein and a lipid; (ii) a buffering agent; (iii) about 1.0 mM to about 2.0 mM calcium chloride; and (iv) about 100 mM to about 200 mM sodium chloride; and (b) about 10% to about 0.1% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

In some embodiments, the present disclosure provides a method of detecting lipolytic activity in an aqueous assay sample, the method comprising (a) combining the aqueous assay sample comprising a protein preparation with an organic solvent comprising 4-methylumbelliferyl oleate (4MuO); and (b) measuring the formation of oleate and 4-methylumbelliferone (4Mu) by fluorescence.

In some embodiments, the present disclosure provides a method of detecting lipolytic activity in an aqueous assay sample, the method comprising (a) combining the aqueous assay sample comprising a protein preparation, with an organic solvent comprising 4-methylumbelliferyl oleate (4MuO) to form an assay composition; (b) combining a control sample comprising a protein preparation and a lipase inhibitor, with an organic solvent comprising 4-methylumbelliferyl oleate (4MuO) to form a control composition; and (c) measuring the formation of oleate and 4-methylumbelliferone (4Mu) by fluorescence in the assay composition and in the control composition.

In some embodiments, the present disclosure provides a method of determining stability of a protein preparation, comprising (a) combining an aqueous assay sample comprising a protein preparation with an organic solvent comprising 4-methylumbelliferyl oleate (4MuO); (b) measuring the formation of oleate and 4-methylumbelliferone (4Mu) by fluorescence; and (c) determining the stability of the protein preparation based on the measured fluorescence.

In some embodiments, the aqueous assay sample has a pH of 5.0 to 7.0. In some embodiments, the aqueous assay sample and the organic solvent are combined at a ratio of about 80:20 to about 98:2. In some embodiments, the aqueous assay sample and the organic solvent are combined at a ratio of about 90:10 to about 99.9:0.1.

In some embodiments, the fluorescence is measured by fluorescence excitation at 330 nm and fluorescence emission at 495 nm. In some embodiments, the fluorescence is measured for up to 24 hours. In some embodiments, the fluorescence is measured for about 24 hours to about 400 hours. In some embodiments, the fluorescence is measured for greater than about 100 hours.

In some embodiments, the aqueous assay sample is incubated with a lipase inhibitor for about 10 minutes to about 1 hour prior to step (a). In some embodiments, the aqueous assay sample is incubated with the lipase inhibitor for about 30 minutes prior to step (a). In some embodiments, the lipase inhibitor is (S)-2-formylamino-4-methyl-pentanoic acid (S)-1-[[(2S,3S)-3-hexyl-4-oxo-2-oxetanyl]methyl]-dodecyl ester (orlistat). In some embodiments, the lipase inhibitor is added at about 1 μM to about 50 μM. In some embodiments, the lipase inhibitor is added at about 5 μM to about 25 μM.

In some embodiments, the present disclosure provides a kit comprising, in two or more containers: (a) an organic solvent; (b) 4-methylumbelliferyl oleate (4MuO); (c) a lipase inhibitor.

In some embodiments, the kit further comprises a buffering agent, a salt, or both. In some embodiments, the kit further comprises a buffer exchange column.

In some embodiments, the present disclosure provides a kit comprising: (a) an organic solvent comprising 4-methylumbelliferyl oleate (4MuO); (b) a column suitable for exchanging buffer of a protein preparation; and (c) a lipase inhibitor.

BRIEF DESCRIPTION OF THE DRAWINGS

FIGS. 1A and 1B show the effect of buffer concentration and pH of Tris and Bis-Tris buffers on pancreatic porcine lipase (PPL) activity and 4-methylumbelliferone (4Mu) fluorescence quenching, respectively. FIG. 1C shows the effect of buffer concentration and pH on lipase activity and autohydrolysis of 4-methylumbelliferyl oleate (4MuO). FIG. 1D shows the pH range at which 4Mu fluorescence was measured. FIG. 1E shows the different forms of 4Mu at various pH.

FIGS. 2A and 2B show the effect of $CaCl_2$ concentration on lipase activity and 4Mu fluorescence quenching, respectively. FIG. 2C shows the effect of $CaCl_2$ concentration on lipase activity and autohydrolysis of 4MuO.

FIGS. 3A and 3B show the effect of NaCl concentration on lipase activity and 4Mu fluorescence quenching, respectively. FIG. 3C shows the effect of NaCl concentration on lipase activity and autohydrolysis of 4MuO.

FIGS. 4A and 4B show the influence of organic solvent on lipase activity and 4Mu fluorescence quenching, respectively. FIG. 4C shows the influence of organic solvent on lipase activity and autohydrolysis of 4MuO.

FIGS. 5A and 5B show the influence of surfactant on lipase activity and 4Mu fluorescence quenching, respectively. FIG. 5C shows the influence of surfactant on lipase activity and autohydrolysis of 4MuO.

FIGS. 6A and 6B show the influence of a lipase inhibitor, orlistat, at three different concentrations on lipase activity and 4Mu fluorescence quenching, respectively.

FIGS. 7A and 7C show the product inhibition influence of theoretically fully degraded PS20 on lipase activity and autohydrolysis of 4Mu. FIGS. 7B and 7D show the product inhibition influence of theoretically fully degraded PS80 on lipase activity and autohydrolysis of 4Mu.

FIG. 8 shows the effect of PS80 on 4Mu fluorescence quenching.

FIGS. 9A and 9B show results of an HPLC-FMA assay to test PS20 (FIG. 9A) and PS80 (FIG. 9B) degradation in varying concentrations of cell culture harvest fluid (CCHF). FIG. 9C shows a theoretical readout of a 4MuO lipase assay. FIG. 9D shows the actual readout of the 4MuO lipase assay testing varying concentrations of CCHF on polysorbate degradation.

FIGS. 10A-10H show results of a 4MuO lipase assay with PS80 at different CCHF concentrations.

FIG. 11 shows the effect of pH of Tris and Bis-Tris on the lipolytic activity of PPL and CCHF, and 4Mu autohydrolysis (AH).

FIG. 12 shows the effects of $CaCl_2$ concentration on lipolytic activity of PPL and CCHF.

FIG. 13 shows the effects of NaCl concentration on lipolytic activity of PPL and CCHF.

FIG. 14 shows the effects of organic solvent on lipolytic activity of PPL and CCHF.

FIG. 15A shows the effects of different surfactants on lipolytic activity of PPL and CCHF. FIG. 15B shows the quenching of 4Mu fluorescence by the different surfactants.

FIG. 16 shows the effect on PPL activity of pre-incubating or co-incubating a sample with a lipase inhibitor, orlistat, at three different concentrations.

FIG. 17A shows the kinetics of a lipase assay performed with a protein-containing formulation with various positive and negative controls (sample, assay, formulation, and autohydrolysis). The samples tested are summarized in Table 10 herein. FIG. 17B is a zoom view of the assay kinetics.

FIG. 18 shows a summary of the lipase assay performed with varying concentrations of CCHF.

FIGS. 19A and 19B relate to Example 1B. FIGS. 19A and 19B show a 4Mu calibration curve in the concentration range of 0.01 to 5 mM and the numerical results of the 4Mu calibration curve, respectively.

DETAILED DESCRIPTION OF THE INVENTION

Figure 1A:
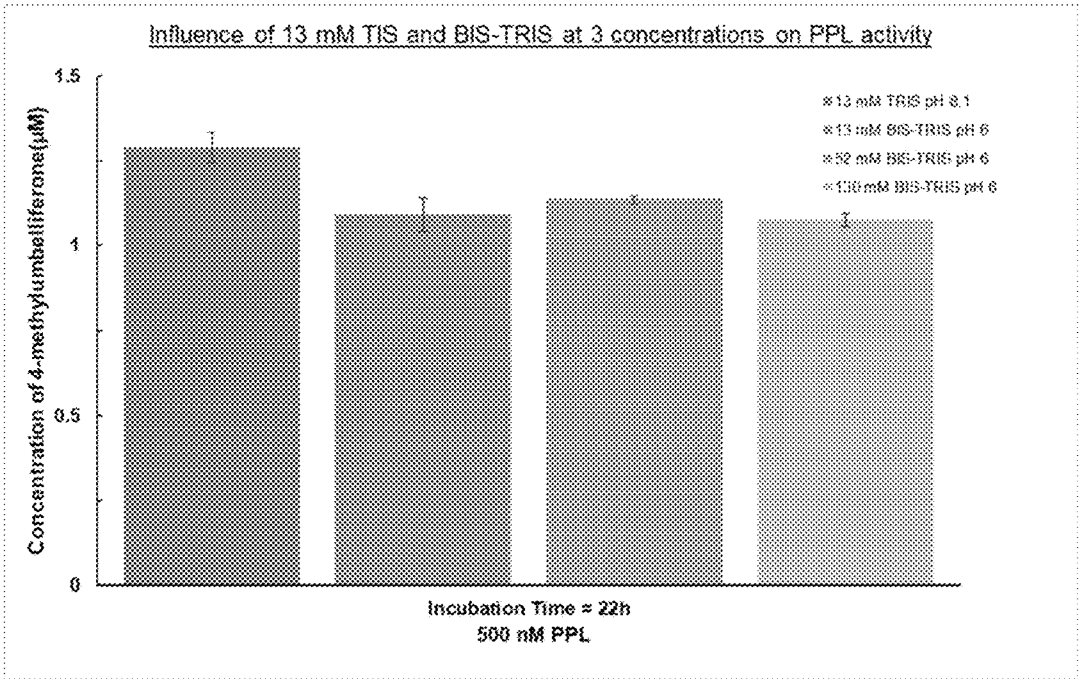
FIGS. 1A-1E relate to Example 1A.

The present disclosure relates to compositions, methods, and kits for detecting lipolytic activity.

As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% or higher variability, depending on the situation. In some embodiments, one of skill in the art will understand the level of variability indicated by the term "about," due to the context in which it is used herein. It should also be understood that use of the term "about" also includes the specifically recited value.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited elements or method steps. It is contemplated that any embodiment discussed in this specification can be implemented with respect to any method, composition, and/or kit of the present disclosure. Furthermore, compositions of the present disclosure can be used to achieve methods and kits of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

As used herein, "protein," "peptide," or "polypeptide" refer to a polymeric form of amino acids, which can be any length. Proteins can include, e.g., antibodies, structural proteins, enzymes, membrane, membrane-associated, and/or transmembrane proteins, transporters, receptors, signaling proteins, and the like. Proteins and/or peptides of the present disclosure also encompass modified proteins, e.g., conjugated to one or more non-peptide substances such as, e.g., a drug, a targeting moiety, a tag such as a visualization tag, and the like. A protein of the present disclosure can be a therapeutic protein, e.g., used in diagnosis, treatment, and/or prevention of a disease or disorder. In some embodiments, a polysorbate described herein can improve stability of the protein in a pharmaceutical formulation. In some embodiments, the therapeutic protein is an antibody. In some embodiments, the therapeutic protein is an antibody-drug conjugate. In some embodiments, a protein preparation described herein includes a protein, e.g., a therapeutic protein.

As used herein in the context of protein preparations, "purification" refers to a process in which one or more substances, e.g., proteins, are isolated from a complex mixture, typically cells, tissues, or organisms. A "purified" protein sample or protein preparation can refer to a sample in which one or more non-water-soluble components of a cell, tissue, or organism (such as, e.g., cell membranes, lipids, aggregated proteins or nucleic acids, and other hydrophobic substances) have been reduced or removed and leaving only the soluble components (such as, e.g., soluble proteins). As used herein, "soluble" can refer to the ability of a substance to dissolve in a certain solvent, e.g., a cell culture medium, a buffer, water or an organic solvent. In the context of proteins, "soluble" can also refer to proteins that do not precipitate and/or aggregate in a certain solvent, e.g., a cell culture medium, a buffer, water, or an organic solvent.

An exemplary purification process can include: growing a cell culture containing the protein of interest, e.g., a therapeutic protein; separating the cells from the culture media; lysing the cells and separating the lysed cells to generate a cell culture supernatant containing the soluble components and a pellet containing the insoluble components described herein; and subjecting the cell culture supernatant to buffer exchange, pH adjustment, centrifugation, filtration (including, e.g., ultrafiltration and/or diafiltration), chromatography, or any combination thereof to generate a purified protein preparation. In some embodiments, a purified protein preparation of the present disclosure is purified by the process described herein. In some embodiments, a partially purified protein preparation of the present disclosure has been subjected to part of the purification process described herein. For example, a partially purified protein preparation may not have been subjected to all of the buffer exchange, pH adjustment, centrifugation, filtration, and/or chromatography steps used for generating the purified protein preparation. In some embodiments, a cell culture supernatant described herein includes a therapeutic protein of the present disclosure. In some embodiments, a partially purified protein preparation described herein includes a therapeutic protein of the present disclosure. In some embodiments, a purified protein preparation described herein includes a therapeutic protein of the present disclosure.

In some embodiments, the present disclosure relates to compositions and methods for the detection of lipolytic activity. Lipolytic activity, i.e., lipolysis, generally refers to the hydrolysis of lipids. The lipolysis reaction can be catalyzed by lipase enzymes, which is a subclass of esterase enzymes. Thus, "lipase" refers to an enzyme that hydrolyzes ester bonds of a lipid, e.g., a triglyceride, a phospholipid, a cholesteryl ester, and the like. Lipases include, e.g., triglyceride lipase, lipoprotein lipase, pancreatic lipase, hepatic lipase, gastric lipase, lingual lipase, endothelial lipase, and phosphatidylserine phospholipase. Lipases are produced naturally, e.g., produced by the pancreas, liver, lingual glands, stomach, thyroids, and/or mucosa in mammals, secreted by certain bacteria and fungi, and/or found in the lysosome. In some embodiments, the lipase is endogenous to the cell from which the protein in the protein purification was derived. In some embodiments, the lipase is endogenous to another biological component in the protein preparation, e.g., a biological component comprising a stabilizing protein added to the protein preparation.

In some embodiments, lipases are produced by cells in a cell culture. In some embodiments, lipases are produced by cells in a cell culture for the production of a protein of interest. Non-limiting examples of cells suitable for production of a protein of interest include bacterial, insect, yeast, mammalian, and/or transgenic cells. Non-limiting examples of cell lines include CHO, HEK 293, HT-1080, PER.C6, CAP, VERO, BHK, HeLa, CV1, Cos, MDCK, 3T3, NS0, NS1, PC12, W138, Sp2/0, HKB-11, TM4, MMT 060562, TR1, MRC 5, FS4, myeloma cell lines, hybridoma cell lines, and hepatoma cell lines. In some embodiments, the cell line for producing the protein of interest is a stable cell line, e.g., wherein the gene for the protein of interest is stably integrated into the genome of the cell. In some embodiments, the cell line for producing the protein of interest is a transient cell line, e.g., wherein the cells express, but do not integrate the gene into the genome.

In some embodiments, the protein of interest is a therapeutic protein. In some embodiments, the protein of interest is purified from the cell culture to generate a purified protein preparation. In some embodiments, lipases in the cell culture are not completely removed from the protein preparation during the purification process. Thus, in some embodiments, a lipase is present in a purified protein preparation.

As referred to herein, "active" lipases are lipases capable of performing lipolysis (also referred to herein as having "lipolytic activity"). Active lipases present in a protein preparation can interfere with downstream processes involving the protein of interest, e.g., therapeutic protein. In some embodiments, a protein preparation comprising a protein of interest, e.g., therapeutic protein, and a lipase is included in a pharmaceutical formulation. In some embodiments, the excipient is added to the protein preparation. In some embodiments, the excipient stabilizes the protein preparation, e.g., by minimizing interfacial stress, reducing protein aggregation, and/or improving protein solubility. In some embodiments, the excipient is a surfactant. In some embodiments, the excipient comprises a fatty acid, an ester, or both. In some embodiments, the excipient is prone to hydrolysis by an active lipase. In some embodiments, the presence of an active lipase in a protein preparation comprising the protein of interest and excipient reduces stability of the preparation. It is therefore advantageous to reliably detect lipolytic activity in a protein preparation, in order to minimize the negative impacts, such as increased particles, safety concerns (due to, e.g., increased injection site reactions), and decreased quality, caused by lipase hydrolysis of excipients.

In some embodiments, the present disclosure provides compositions in which lipolytic activity in a protein preparation can be detected.

In some embodiments, the present disclosure provides a composition comprising (a) an aqueous assay sample comprising a protein preparation; and (b) an organic solvent, wherein the organic solvent further comprises 4-methylumbelliferyl oleate (4MuO); wherein the aqueous assay sample has a pH of 5.0 to 7.0; and wherein the aqueous assay sample is about 80% to about 98% of the composition, and the organic solvent is about 2% to about 20% of the composition.

In further embodiments, the present disclosure provides a composition comprising (a) an aqueous assay sample comprising (i) a purified protein preparation, (ii) a buffering agent, and (iii) a salt; and (b) an organic solvent, wherein the organic solvent further comprises 4-methylumbelliferyl oleate (4MuO); wherein the aqueous assay sample has a pH of 5.0 to 7.0; and wherein the aqueous assay sample is about 80% to about 98% (vol/vol) of the composition, and the organic solvent is about 2% to about 20% (vol/vol) of the composition.

In still further embodiments, the present disclosure provides a composition comprising (a) about 90% to about 98% (vol/vol) of an aqueous assay sample comprising (i) a purified protein preparation, (ii) a buffering agent, (iii) about 1.0 mM to about 20 mM calcium chloride, and (iv) about 100 mM to about 200 mM sodium chloride; and (b) about 2% to about 10% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

As used herein, "aqueous" (e.g., aqueous assay sample) refers to a solution or sample in which water is the solvent. Thus, aqueous assay samples of the present disclosure can include, e.g., cell culture media, buffer solutions, protein samples, and the like. In some embodiments, the aqueous assay sample of the present disclosure comprises a protein preparation.

In some embodiments, the protein preparation is a cell culture supernatant. Cell culture supernatants are described herein and can be obtained, e.g., from a cell culture for producing a protein of interest. In some embodiments, the protein is a therapeutic protein. In some embodiments, a cell culture supernatant is produced after lysing the cultured cells and separating the soluble and insoluble components, e.g., by centrifugation. Examples of cells and cell lines suitable for culturing and protein production are provided herein. In some embodiments, cell culture supernatant comprises a protein of interest, e.g., a therapeutic protein, and additional host cell components. In some embodiments, the additional host cell components comprise additional host cell proteins. In some embodiments, the additional host cell proteins comprises a lipase. In some embodiments, the lipase has lipolytic activity.

In some embodiments, the protein preparation is a partially purified protein preparation. Partially purified protein preparations are described herein and can be obtained, e.g., after undergoing a partial purification procedure (e.g., a purification process described herein) for a protein of interest from a cell culture. In some embodiments, the protein is a therapeutic protein. In some embodiments, a partially purified protein preparation has undergone additional purification steps compared to a cell culture supernatant. In some embodiments, a partially purified protein preparation comprises a therapeutic protein and additional components of the host cell. In some embodiments, the host cell components comprise host cell proteins. In some embodiments, the host cell proteins comprises a lipase. In some embodiments, the lipase has lipolytic activity. In some embodiments, the therapeutic protein is 20% to 95% (w/w), 30% to 90% (w/w) or 40% to 80% (w/w) of all proteins in the in the partially purified protein preparation.

In some embodiments, the protein preparation is a purified protein preparation. Purified protein preparations are described herein and can be obtained, e.g., after undergoing a purification procedure (e.g., a purification process described herein) for a protein of interest from a cell culture. In some embodiments, the protein of interest is a therapeutic protein. In some embodiments, a purified protein preparation a therapeutic protein and additional components of the host cell. In some embodiments, the host cell components comprise host cell proteins. In some embodiments, the host cell proteins comprises a lipase. In some embodiments, the lipase has lipolytic activity. In some embodiments, the therapeutic protein is greater than 70% (w/w), greater than 80% (w/w), greater than 85% (w/w), greater than 90% (w/w), greater than 95% (w/w), or greater than 99% (w/w) of all proteins in the in the purified protein preparation.

In some embodiments, the protein preparation comprises a therapeutic protein. Non-limiting examples of therapeutic proteins include antibodies (such as monoclonal or polyclonal antibodies) and antibody fragments; protein-based vaccines (such as, e.g., hepatitis B surface antigen); blood factors (such as, e.g., Factor VIII and Factor IX); thrombolytic agents (such as, e.g., tissue plasminogen activator); hormones (such as, e.g., insulin, glucagon, growth hormone, and gonadotrophin); hematopoietic growth factors (such as, e.g., erythropoietin and colony stimulating factors); interferons (such as, e.g., interferon-$\alpha$, interferon-$\beta$, and interferon-$\gamma$); interleukin-based proteins (such as, e.g., interleukin-12); and other proteins such as tumor necrosis factor and therapeutic enzymes. Further examples of protein-based therapeutics include belimumab, ipilimumab, belatacept, brentuximab vedotin, aflibercept, asparaginase *Erwinia chrysanthemi,* glucarpidase, obinutuzumab, pembrolizumab, blinatumomab, nivolumab, idarucizumab, asofatase-alfa, daratumumab, elotuzumab, sebelipase alfase, atezolizumab, taliglucerase alfa, raxibacumab, elosulfase alfa, metreleptin, ramucirumab, siltuximab, pembrolizumab, dinutuximab, evolocumab, necitumumab, obiltoxaximab, abatacept, adalimumab, alefacept, etanercept, infliximab, trastuzumab, ustekinumab, denileukin diftitox, and golimumab. Further examples of protein therapeutics are described in, e.g., Dimitrov, Methods Mol Biol 899: 1-26 (2012), Lagasse et al., F1000Res 6: 113 (2017), and Protein Therapeutics, Eds: Vaughan et al., 2017: Wiley-VCH Verlag. Therapeutic proteins can include recombinant proteins, modified proteins and fusion proteins, such as, e.g., antibody-drug conjugates, antibody-cytokine fusions, Fc-fusions, bispecific antibodies, multispecific antibodies, affibody fusions, glycosylated proteins and peptides, and engineered receptor antagonists. In some embodiments, the protein preparation comprising the therapeutic protein is used in a pharmaceutical formulation.

In some embodiments, the protein preparation comprises a commercially important protein, e.g., an industrial enzyme. Commercially important proteins can be used in a variety of industries such as pharmaceuticals, chemical production, biofuels, food and beverage, and consumer products. For example, in some embodiments, the protein preparation is an enzyme used within a process to generate a desired product or may be the product of interest. In some embodiments, the commercially important protein is used in the food, pharmaceutical synthesis, biofuel, chemical, or manufacturing industries. In some embodiments, the industrial enzyme includes, but is not limited to, palatase lipozyme, lipopan, xylose isomerase, bromelain and noopazyme (used in the food industry), cellulase and amylase (used in the biofuel industry), resinase (used in the paper processing industry), amidase (used in the chemical industry), novozym-435 (used in cosmetic production of isopropyl myristate) or subtilisin (used in detergents).

In some embodiments, the protein preparation comprises a pharmaceutical excipient. Pharmaceutical excipients are included, e.g., to aid in the processing of the drug delivery system before, during, or after manufacture; to protect, support, or enhanced stability, bioavailability, or patient acceptability; to assist in product identification and enhance overall safety; to assist in the effectiveness and/or delivery of the drug in use; and/or to assist in maintaining integrity of the drug product during storage. Non-limiting examples of pharmaceutical excipients include surfactants, fillers, diluents, binders, suspending agents, viscosity agents, coatings, flavoring agents, disintegrants, colorants, lubricants, glidants, preservatives, sweeteners, and the like. In some embodiments, the pharmaceutical excipient is added to the protein preparation. In some embodiments, the pharmaceutical excipient is added to the protein preparation before, after, or during purification.

In some embodiments, the pharmaceutical excipient is a surfactant. As used herein, "surfactant" refers to an agent that lowers surface tension or interfacial tension between two liquids. In some embodiments, surfactants can stabilize a composition, e.g., a protein preparation described herein, by minimizing aggregation and/or precipitation and/or improving solubility (e.g., by lowering surface tension and inhibiting protein surface adsorption; see, e.g., Agarkhed et al., AAPS PharmSciTech 14:1-9 (2013)) of one or more components of the composition. Surfactants in pharmaceutical compositions can also modulate bioavailability of an active pharmaceutical ingredient (API); assist the API in maintaining a preferred polymorphic form; prevent aggregation or dissociation; and/or modulate immunogenic responses of active ingredients. Surfactants can include cationic, anionic, non-ionic, zwitterionic, amphoteric, and/or ampholytic surfactants. Non-limiting examples of surfactants include polysorbates (e.g., TWEEN surfactants such as TWEEN 20 and TWEEN 80, which are also known as polysorbate 20, polysorbate 80, respectively) derived from ethoxylated sorbitans esterified with fatty acids (e.g., lauric acid in polysorbate 20 and oleic acid in polysorbate 80); tyloxapols; poloxamers (e.g., PLURONIC F68LF, PLURONIC L-G2LF, PLURONIC L62D, LUTROL F68, and KOLLIPHOR P188); polyoxyethylene castor oil (e.g., KOLLIPHOR EL) and derivatives thereof; sorbitan esters, also known as Spans; polyoxyl stearates; lecitins; phospholipids; polyoxyethylene surfactants such as, e.g., TRITON (e.g., TRITON X-100) and BRIJ (e.g., BRIJ 35); and polyethoxylated fatty acids such as, e.g., MYRJ S40, MYRJ S100, and MYRJ 52.

In some embodiments, the surfactant comprises a fatty acid. In some embodiments, the surfactant comprises an ester. In some embodiments, the surfactant is a polysorbate. Polysorbates are a class of compounds derived from ethoxylated sorbitans esterified with fatty acids and include, e.g., polysorbate 20, polysorbate 40, polysorbate 60, polysorbate 80, polysorbate 21, polysorbate 61, polysorbate 65, polysorbate 81, and polysorbate 81. In some embodiments, the protein preparation provided herein includes a polysorbate. In some embodiments, the polysorbate in the protein preparation is polysorbate 20, polysorbate 80, or combinations thereof.

In some embodiments, the surfactant is at about 0.001% w/v to about 2% w/v of the aqueous assay sample. In some embodiments, the surfactant is at about 0.005% w/v to about 2% w/v of the aqueous assay sample. In some embodiments, the surfactant is at about 0.01% w/v to about 2% w/v of the aqueous assay sample. In some embodiments, the surfactant is at about 0.02% to about 1.5% w/v of the aqueous assay sample. In some embodiments, the surfactant is at about 0.03% to about 1.0% w/v of the aqueous assay sample. In some embodiments, the surfactant is at about 0.04% to about 0.8% w/v of the aqueous assay sample. In some embodiments, the surfactant is at about 0.05% to about 0.6% w/v of the aqueous assay sample. In some embodiments, the surfactant is at about 0.06% to about 0.4% w/v of the aqueous assay sample. In some embodiments, the surfactant is at about 0.07% to about 0.2% w/v of the aqueous assay sample. In some embodiments, the surfactant is at about 0.08% to about 0.15% w/v of the aqueous assay sample. In some embodiments, the surfactant is at about 0.09% to about 0.10% w/v of the aqueous assay sample. In some embodiments, the surfactant is at about 0.01% to about 0.04% w/v of the aqueous assay sample. In some embodiments, the surfactant is a polysorbate. In some embodiments, the surfactant is polysorbate 20, polysorbate 80, or combinations thereof.

In some embodiments, the protein preparation further comprises one or more additional host cell proteins. As described herein, the protein preparation is prepared from a cell culture, i.e., comprising host cells of the protein of interest, e.g., a therapeutic protein. In some embodiments, the protein preparation includes one or more additional host cell proteins. In some embodiments, the additional host cell proteins are soluble in substantially the same conditions as the protein of interest, e.g., therapeutic protein. In some embodiments, the additional host cell proteins are not easily separable from the protein of interest, e.g., therapeutic protein. In some embodiments, the additional host cell proteins comprise a lipase. In some embodiments, one or more of the additional host cell proteins have lipolytic activity.

In some embodiments, the aqueous assay sample comprising the protein preparation further comprises a buffering agent, a salt, or both. In general, a salt of the present disclosure refers to an ionic compound whose anion is not $OH^-$ and $O^{2-}$. In some embodiments, the salt reduces and/or prevents degradation of one or more components in the composition. Suitable salts that can be included in an aqueous assay samples can be selected by one of ordinary skill in the art, including, e.g., sodium salts, potassium salts, calcium salts, ammonium salts, and the like. In some embodiments, the salt is potassium chloride (KCl), sodium chloride (NaCl), sodium carbonate ($Na_2CO_3$), sodium sulfate ($Na_2SO_4$), calcium chloride ($CaCl_2$), ammonium chloride ($NH_4Cl$), ammonium acetate ($NH_4CH_3COO$), ammonium sulfate ($(NH_4)_2SO_4$), or combination thereof. In some embodiments, the salt is NaCl, $CaCl_2$, or combination thereof. In some embodiments, the salt is both NaCl and $CaCl_2$.

In some embodiments, the concentration of NaCl in the aqueous assay sample facilitates accurate and/or efficient detection of lipolytic activity in the sample. In some embodiments, the NaCl is about 10 mM to about 500 mM in the aqueous assay sample. In some embodiments, the NaCl is about 25 mM to about 400 mM in the aqueous assay sample. In some embodiments, the NaCl is about 50 mM to about 300 mM in the aqueous assay sample. In some embodiments, the NaCl is about 75 mM to about 250 mM in the aqueous assay sample. In some embodiments, the NaCl is about 100 mM to about 200 mM in the aqueous assay sample. In some embodiments, the NaCl is about 50 mM, about 60 mM, about 70 mM, about 80 mM, about 90 mM, about 100 mM, about 110 mM, about 120 mM, about 130 mM, 140 mM, 150 mM, 160 mM, 170 mM, 180 mM, 190 mM, or 200 mM in the aqueous assay buffer.

In some embodiments, the NaCl is about 10 mM to about 500 mM in the final composition (aqueous assay sample and organic solvent). In some embodiments, the NaCl is about 25 mM to about 400 mM in the final composition. In some embodiments, the NaCl is about 50 mM to about 300 mM in the final composition. In some embodiments, the NaCl is about 75 mM to about 250 mM in the final composition. In some embodiments, the NaCl is about 100 mM to about 200 mM in the final composition. In some embodiments, the NaCl is about 100 mM to about 140 mM, e.g., 120 mM in the final composition. In some embodiments, the NaCl is about 50 mM, about 60 mM, about 70 mM, about 80 mM, about 90 mM, about 100 mM, about 110 mM, about 120 mM, about 130 mM, 140 mM, 150 mM, 160 mM, 170 mM, 180 mM, 190 mM, or 200 mM in the final composition.

In some embodiments, the concentration of $CaCl_2$ in the aqueous assay sample facilitates accurate and/or efficient detection of lipolytic activity in the sample. In some embodiments, the $CaCl_2$ is about 0.1 mM to about 20 mM in the aqueous assay sample. In some embodiments, the $CaCl_2$ is about 0.2 mM to about 10 mM in the aqueous assay sample. In some embodiments, the $CaCl_2$ is about 0.5 mM to about 5.0 mM in the aqueous assay sample. In some embodiments, the $CaCl_2$ is about 0.7 mM to about 3.0 mM in the aqueous assay sample. In some embodiments, the $CaCl_2$ is about 1.0 mM to about 2.0 mM in the aqueous assay sample. In some embodiments, the $CaCl_2$ is about 0.5 mM, about 0.6 mM, about 0.7 mM, about 0.8 mM, about 0.9 mM, about 1.0 mM, about 1.1 mM, about 1.2 mM, about 1.3 mM, about 1.5 mM, about 1.5 mM, about 1.6 mM, about 1.7 mM, about 1.8 mM, about 1.9 mM, about 2.0 mM, about 2.5 mM, about 3.0 mM, about 3.5 mM, about 4.0 mM, about 4.5 mM, or about 5.0 mM in the aqueous assay sample.

In some embodiments, the $CaCl_2$ is about 0.1 mM to about 20 mM in the final composition (aqueous assay sample and organic solvent). In some embodiments, the $CaCl_2$ is about 0.2 mM to about 10 mM in the final composition. In some embodiments, the $CaCl_2$ is about 0.5 mM to about 5.0 mM in the final composition. In some embodiments, the $CaCl_2$ is about 0.7 mM to about 3.0 mM in the final composition. In some embodiments, the $CaCl_2$ is about 1.0 mM to about 2.0 mM in the final composition. In some embodiments, the $CaCl_2$ is about 0.5 mM, about 0.6 mM, about 0.7 mM, about 0.8 mM, about 0.9 mM, about 1.0 mM, about 1.1 mM, about 1.2 mM, about 1.3 mM, about 1.5 mM, about 1.5 mM, about 1.6 mM, about 1.7 mM, about 1.8 mM, about 1.9 mM, about 2.0 mM, about 2.5 mM, about 3.0 mM, about 3.5 mM, about 4.0 mM, about 4.5 mM, or about 5.0 mM in the final composition.

In some embodiments, the NaCl and $CaCl_2$ reduce and/or prevent degradation of one or more components in the aqueous assay sample. In some embodiments, the NaCl and $CaCl_2$ reduce and/or prevent aggregation and/or precipitation of the protein, e.g., the therapeutic protein. In some embodiments, the NaCl and $CaCl_2$ reduce and/or prevent degradation of one or more components in the composition that is not in the aqueous assay sample, e.g., in the organic solvent. In some embodiments, the NaCl and $CaCl_2$ reduce and/or prevent autohydrolysis of 4-methylumbelliferyl oleate (4MuO). In some embodiments, the NaCl is about 10 mM to about 500 mM, and the $CaCl_2$ is about 0.1 mM to about 20 mM in the aqueous assay sample. In some embodiments, the NaCl is about 25 mM to about 400 mM, and the $CaCl_2$ is about 0.2 mM to about 10 mM in the aqueous assay sample. In some embodiments, the NaCl is about 50 mM to about 300 mM, and the CaChis about 0.5 mM to about 5.0 mM in the aqueous assay sample. In some embodiments, the NaCl is about 75 mM to about 250 mM, and the $CaCl_2$ is about 0.7 to about 3.0 mM in the aqueous assay sample. In some embodiments, the NaCl is about 100 mM to about 200 mM, and the CaChis about 1.0 to about 2.0 mM in the aqueous assay sample. In some embodiments, the NaCl is about 150 mM and the $CaCl_2$ is about 0.3 mM in the aqueous assay sample.

As used herein, a "buffering agent" refers to a substance used in a solution to maintain the pH of the solution. Buffering agents can maintain a solution at a certain pH range (i.e., the buffering capacity in a given range) and prevent a rapid change in pH when additional components are added to the solution. In general, a buffering agent can be a weak acid or weak base. In some embodiments, the buffering agent has a buffering capacity at about pH 5.0, about pH 5.5, about pH 6.0, about pH 6.5, or about pH 7.0. Buffering agents with buffering capacity of about pH 5.0 to about pH 7.0 include, e.g., citrate, acetate, phosphate, MES, Bis-Tris, ADA, ACES, PIPES, MOPSO, Bis-Tris propane, BES, MOPS, TES, HEPES, DIPSO, MOBS, TAPSO, and Tris. The buffering capacity of a buffering agent can be determined by the skilled artisan. In some embodiments, the buffering agent in the aqueous assay sample facilitates accurate and/or efficient detection of lipolytic activity in the sample. In some embodiments, the buffering agent reduces and/or prevents degradation of one or more components in the aqueous assay sample. In some embodiments, the buffering agent reduces and/or prevents aggregation of the protein, e.g., the therapeutic protein. In some embodiments, the buffering agent reduces and/or prevents degradation of one or more components in the composition that is not in the aqueous assay sample, e.g., in the organic solvent of the composition. In some embodiments, the buffering agent reduces and/or prevents autohydrolysis of 4-methylumbelliferyl oleate (4MuO). In some embodiments, the buffering agent is provided in the aqueous assay sample as an aqueous buffer solution.

In some embodiments, the buffering agent is about 5 mM to about 200 mM in the aqueous assay sample. In some embodiments, the buffering agent is about 10 mM to about 100 mM in the aqueous assay sample. In some embodiments, the buffering agent is about 20 mM to about 80 mM in the aqueous assay sample. In some embodiments, the buffering agent is about 30 mM to about 70 mM in the aqueous assay sample. In some embodiments, the buffering agent is about 40 mM to about 60 mM in the aqueous assay sample. In some embodiments, the buffering agent is about 10 mM, about 12 mM, about 15 mM, about 18 mM, about 20 mM, about 22 mM, about 25 mM, about 28 mM, about 30 mM, about 32 mM, about 35 mM, about 38 mM, about 40 mM, about 42 mM, about 45 mM, about 48 mM, about 50 mM, about 52 mM, about 55 mM, about 58 mM, about 60 mM, about 62 mM, about 65 mM, about 68 mM, about 70 mM, about 72 mM, about 75 mM, about 78 mM, about 80 mM, about 82 mM, about 85 mM, about 88 mM, about 90 mM, about 92 mM, about 95 mM, about 98 mM, or about 100 mM in the aqueous assay sample. In some embodiments, the buffering agent is Bis-Tris. In some embodiments, the buffering agent is Tris.

In some embodiments, the buffering agent is about 5 mM to about 200 mM in the final composition (aqueous assay sample and organic solvent). In some embodiments, the buffering agent is about 10 mM to about 100 mM in the final composition (aqueous assay sample and organic solvent). In some embodiments, the buffering agent is about 20 mM to about 80 mM in the final composition. In some embodiments, the buffering agent is about 30 mM to about 70 mM in the final composition. In some embodiments, the buffering agent is about 40 mM to about 60 mM in the final composition. In some embodiments, the buffering agent is about 10 mM, about 12 mM, about 15 mM, about 18 mM, about 20 mM, about 22 mM, about 25 mM, about 28 mM, about 30 mM, about 32 mM, about 35 mM, about 38 mM, about 40 mM, about 42 mM, about 45 mM, about 48 mM, about 50 mM, about 52 mM, about 55 mM, about 58 mM, about 60 mM, about 62 mM, about 65 mM, about 68 mM, about 70 mM, about 72 mM, about 75 mM, about 78 mM, about 80 mM, about 82 mM, about 85 mM, about 88 mM, about 90 mM, about 92 mM, about 95 mM, about 98 mM, or about 100 mM in the final composition.

In some embodiments, the aqueous assay sample comprises NaCl, $CaCl_2$, and a buffering agent. In some embodiments, the NaCl is about 10 mM to about 500 mM, the $CaCl_2$ is about 0.1 mM to about 20 mM, and the buffering agent is about 5 mM to about 200 mM in the aqueous assay sample. In some embodiments, the NaCl is about 25 mM to about 400 mM, the $CaCl_2$ is about 0.2 mM to about 10 mM, and the buffering agent is about 10 mM to about 100 mM in the aqueous assay sample. In some embodiments, the NaCl is about 50 mM to about 300 mM, the $CaCl_2$ is about 0.5 mM to about 5.0 mM, and the buffering agent is about 20 mM to about 8 mM in the aqueous assay sample. In some embodiments, the NaCl is about 75 mM to about 250 mM, the $CaCl_2$ is about 0.7 to about 3.0 mM, and the buffering agent is about 30 mM to about 70 mM in the aqueous assay sample. In some embodiments, the NaCl is about 100 mM to about 200 mM, the $CaCl_2$ is about 1.0 to about 2.0 mM, and the buffering agent is about 40 mM to about 60 mM in the aqueous assay sample. In some embodiments, the NaCl is about 150 mM, the $CaCl_2$ is about 0.3 mM, and the buffering agent is about 45 mM to about 55 mM in the aqueous assay sample. In some embodiments, the buffering agent is Bis-Tris. In some embodiments, the buffering agent is Tris. One of skill in the art would recognize that salts and buffers are commonly found in a protein preparation, and thus the above percentages are provided by example only.

In some embodiments, the pH of the aqueous assay sample is adjusted to maximize the fluorescence intensity of the 4Mu. In some embodiments, the pH of the aqueous assay sample is adjusted to stabilize one or more components of the aqueous assay sample and/or the organic solvent. In some embodiments, a slightly acidic to neutral pH (e.g., about 5.0 to about 7.0) minimizes degradation of components in the aqueous assay sample. In some embodiments, a slightly acidic to neutral pH (e.g., about 5.0 to about 7.0) minimizes aggregation of the therapeutic protein. In some embodiments, a slightly acidic to neutral pH (e.g., about 5.0 to about 7.0) minimizes autohydrolysis of 4-methylumbelliferyl oleate (4MuO).

In some embodiments, the aqueous assay sample has an acidic pH. In some embodiments, the aqueous assay sample has a pH of 5.0 to 7.0. In some embodiments, the aqueous assay sample has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0.

In some embodiments, the composition of the present disclosure comprises an aqueous assay sample as described herein, and an organic solvent. As used herein, "organic solvent" refers a carbon-based substance that can be used to dissolve one or more solutes. Examples of organic solvents include, but are not limited to, hydrocarbons including, e.g., aliphatic hydrocarbons, cyclic hydrocarbons, aromatic hydrocarbons, and halogenated hydrocarbons; ketones; amines; esters; alcohols; aldehydes; ethers; nitriles; sulfoxides; and the like. In some embodiments, the organic solvent is capable of solubilizing 4-methylumbelliferyl oleate (4MuO).

In some embodiments, the organic solvent comprises an alcohol, a sulfoxide, a nitrile, or combination thereof. In some embodiments, the organic solvent is dimethyl sulfoxide (DMSO). In some embodiments, the organic solvent comprises acetonitrile (ACN). In some embodiments, the organic solvent comprises an alcohol. In some embodiments, the organic solvent is a $C_1$-$C_6$ alcohol. In some embodiments, the $C_1$-$C_6$ alcohol is methanol, ethanol, propanol, iso-propanol, butanol, sec-butanol, tert-butanol, pentanol, or hexanol. In some embodiments, the organic solvent is methanol, ethanol, propanol, iso-propanol, butanol, sec-butanol, tert-butanol, or combination thereof. In some embodiments, the organic solvent comprises a mixture of acetonitrile and an alcohol. In some embodiments, the organic solvent comprises a mixture of acetonitrile and iso-propanol. In some embodiments, the acetonitrile and iso-propanol are mixed at a ratio of about 5:1, about 4:1, about 3 :1, about 2:1 or about 1:1.

In some embodiments, 4-methylumbelliferyl oleate (4MuO) is present in the organic solvent. 4MuO has the structure:

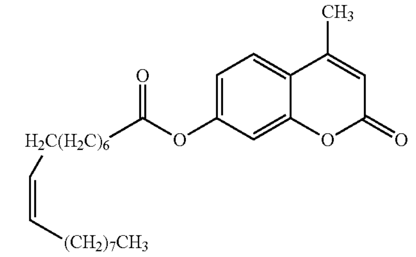

In some embodiments, 4MuO hydrolyzes to form oleic acid and 4-methylumbelliferone (4Mu) (Scheme I):

Scheme I

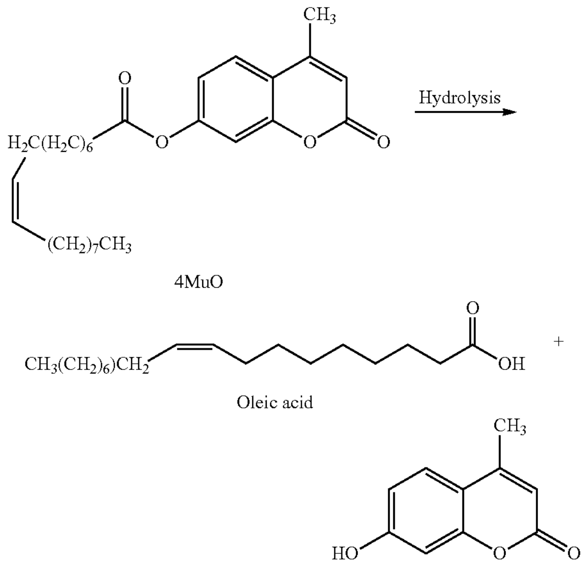

4MuO

Oleic acid

4Mu

In some embodiments, 4MuO is not fluorescent. In some embodiment, 4Mu is fluorescent. In some embodiments, fluorescence of 4Mu is used to detect the hydrolysis of 4MuO by a lipase, and thus is an indicator of lipolytic activity. The skilled artisan will understand that the hydrolysis of 4MuO (as measured by 4Mu fluorescence) will likely indicate that lipolytic activity has occurred in the protein preparation, i.e., that surfactants may have been hydrolyzed, possibly rendering the protein preparation unstable. In some embodiments, fluorescence of 4Mu can be measured at excitation wavelength of about 330 nm and emission wavelength of about 495 nm. In some embodiments, fluorescence of 4Mu can be measured at excitation wavelength of about 327 nm and emission wavelength of about 449 nm. In some embodiments, fluorescence of 4Mu can be measured at excitation wavelength of about 300 nm to about 350 nm and emission wavelength of about 420 nm to about 500 nm. In some embodiments, fluorescence measurement parameters of 4Mu (e.g., the excitation and emission wavelengths) vary when pH is changed. In some embodiments, fluorescence measurement parameters of 4Mu vary when salt and/or buffering agent concentration is changed. In some embodiments, 4MuO is a substrate for a lipase. In some embodiments, 4MuO is hydrolyzed by a lipase in the protein preparation described herein. In some embodiments, 4Mu formation is measured by fluorescence. In some embodiments, lipolytic activity of an assay sample comprising a protein preparation described herein, is measured by the fluorescence of 4Mu.

Various concentrations of 4MuO can be used in the compositions and methods described herein. Generally, the amount of 4MuO should be minimized to minimize the effect of autohydrolysis. In some embodiments, the 4MuO in the organic solvent is about 1 μM to about 1 mM, or about 10 μM to about 500 μM, or about 20 μM to about 200 μM, or about 50 μM to about 150 μM, or about 75 μM to about 125 μM, or about 100 μM.

In some embodiments, the composition comprises the aqueous assay sample comprising the protein preparation as described herein; and the organic solvent comprising 4MuO as described herein. In some embodiments, the composition does not comprise an equal volume of the aqueous assay sample and the organic solvent. In some embodiments, the amount of organic solvent in the composition is less than the amount of aqueous assay buffer in the composition, in order to minimize potentially adverse effects of the organic solvent on the protein preparation, in particular the therapeutic protein. For example, if the amount of organic solvent is too high, the therapeutic protein may aggregate. In some embodiments, the aqueous assay sample is about 70% to about 99.9% by volume of the composition, and the organic solvent is about 0.1% to about 30% by volume of the composition. In some embodiments, the aqueous assay sample is about 70% to about 99.5% by volume of the composition, and the organic solvent is about 0.5% to about 30% by volume of the composition. In some embodiments, the aqueous assay sample is about 70% to about 99% by volume of the composition, and the organic solvent is about 1% to about 30% by volume of the composition. In some embodiments, the aqueous assay sample is about 75% to about 99% by volume of the composition, and the organic solvent is about 1% to about 25% by volume of the composition. In some embodiments, the aqueous assay sample is about 80% to about 98% by volume of the composition, and the organic solvent is about 2% to about 20% by volume of the composition. In some embodiments, the aqueous assay sample is about 90% to about 98% by volume of the composition, and the organic solvent is about 2% to about 10% by volume of the composition. In some embodiments, the aqueous assay sample is about 95% to about 98% by volume of the composition, and the organic solvent is about 2% to about 5% by volume of the composition.

In some embodiments, the aqueous assay sample is about 80%, about 81%, about 82%, about 83%, about 84%, about 85%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% by volume of the composition. In some embodiments, the protein preparation is about 70% to about 85%, about about 75% to about 85%, or about 80% to about 85% by volume of the composition, and the non-protein preparation components of the aqueous assay sample, e.g., the buffering agent and/or salt, comprise about 15% to about 30%, about 15% to about 25%, about 15% to about 20% by volume of the composition. In some embodiments, the organic solvent is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, or about 50% by volume of the composition. One of skill in the art would recognize that salts and buffers are commonly found in a protein preparation, and thus the above percentages are used by example only.

In some embodiments, the composition further comprises a lipase inhibitor. In some embodiments, the lipase inhibitor reduces or abolishes lipolytic activity in the composition by inactivating a lipase. In some embodiments, the lipase inhibitor is included in the composition to provide a negative control for detection of lipolytic activity, i.e., a composition comprising a lipase inhibitor is not expected to have lipolytic activity. In some embodiments, the lipase inhibitor is added to the composition after detecting lipolytic activity, e.g., by measuring fluorescence of 4Mu. In some embodiments, the lipase inhibitor is in the aqueous assay sample. In some embodiments, the lipase inhibitor is water soluble. In some embodiments, the lipase inhibitor is in the organic solvent. In some embodiments, the lipase inhibitor is not water soluble.

In some embodiments, the lipase inhibitor is at a concentration sufficient to reduce or abolish lipolytic activity in the composition. In some embodiments, the lipase inhibitor is at a concentration sufficient to reduce lipolytic activity in the composition by about 50%, about 60%, about 70%, about 80%, about 90%, about 95%, about 99% or about 100% in the composition. In some embodiments, the lipase inhibitor is about 1 μM to about 50 μM in the composition. In some embodiments, the lipase inhibitor is about 2 μM to about 40 μM in the composition. In some embodiments, the lipase inhibitor is about 3 μM to about 35 μM in the composition. In some embodiments, the lipase inhibitor is about 4 μM to about 30 μM in the composition. In some embodiments, the lipase inhibitor is about 5 μM to about 25 μM in the composition. In some embodiments, the lipase inhibitor is about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 16 μM, about 17 μM, about 17 μM, about 18 μM, about 19 μM, about 20 μM, about 21 μM, about 22 μM, about 23 μM, about 24 μM, about 25 μM, about 30 μM, about 35 μM, about 40 μM, about 45 μM, or about 50 μM in the composition.

In some embodiments, the lipase inhibitor is (S)-2-formylamino-4-methyl-pentanoic acid (S)-1-[[(2S,3S)-3-hexyl-4-oxo-2-oxetanyl]methyl ]-dodecyl ester (orlistat). In some embodiments, the lipase inhibitor is an alkaloid, e.g., caffeine, theophylline, and theobromine. In some embodiments, the lipase inhibitor is a carotenoid such as, e.g., fucoxanthin. In some embodiments, the lipase inhibitor is a glycoside, e.g., acteoside, kaempferol-3-O-rutinoside, rutin, kaempferol, quercetin, and luteolin. In some embodiments, the lipase inhibitor is a polyphenol, e.g., galangin, hesperidin, licohalcone A, CT-II, 7-phloroeckol, and isoliquiritigenin. In some embodiments, the lipase inhibitor is a saponin, e.g., sessiloside and chiianoside. In some embodiments, the lipase inhibitor is a terpene, e.g., crocin and crocetin. In some embodiments, the lipase inhibitor is derived from bacteria, e.g., lipstatin, valilactone, percyquinnin, panclicin, ebelactone, vibralactone, and esterastin. In some embodiments, the lipase inhibitor is a synthetic lipase inhibitor, e.g., synthetic analogs of natural fats. Lipase inhibitors are reviewed in Lunagariya yet al., EXCLI J 13: 897-921 (2014).

In some embodiments, the disclosure provides a composition comprising: (a) about 90% to about 99.9% (vol/vol) of an aqueous assay sample comprising (i) a purified protein preparation comprising a protein and a lipid; (ii) a buffering agent; (iii) about 1.0 mM to about 2.0 mM calcium chloride; and (iv) about 100 mM to about 200 mM sodium chloride; and (b) about 10% to about 0.1% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

In some embodiments, the disclosure provides a composition comprising: (a) about 90% to about 99.9% (vol/vol) of an aqueous assay sample comprising (i) a purified protein preparation comprising a protein and a polysorbate surfactant; (ii) a buffering agent; (iii) about 1.0 mM to about 2.0 mM calcium chloride; and (iv) about 100 mM to about 200 mM sodium chloride; and (b) about 10% to about 0.1% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

In some embodiments, the present disclosure provides a composition comprising: (a) about 90% to about 99.9% (vol/vol) of an aqueous assay sample comprising (i) a partially purified protein preparation comprising a protein and a lipid; (ii) a buffering agent; (iii) about 1.0 mM to about 2.0 mM calcium chloride; and (iv) about 100 mM to about 200 mM sodium chloride; and (b) about 10% to about 0.1% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

In some embodiments, the present disclosure provides a composition comprising: (a) about 90% to about 99.9% (vol/vol) of an aqueous assay sample comprising (i) a cell culture supernatant comprising a protein and a lipid; (ii) a buffering agent; (iii) about 1.0 mM to about 2.0 mM calcium chloride; and (iv) about 100 mM to about 200 mM sodium chloride; and (b) about 10% to about 0.1% (vol/vol) of an organic solvent selected from methanol, ethanol, propanol, iso-propanol, butanol, sec-butanol, iso-butanol, tert-butanol, dimethyl sulfoxide (DMSO), acetonitrile, or combinations thereof, further comprising 4-methylumbelliferyl oleate (4MuO); wherein the aqueous assay sample has a pH of 5.0 to 7.0.

In additional embodiments, the compositions provided herein are suitable to be used in a method for detecting lipolytic activity in a protein preparation. In some embodiments, the present disclosure further provides methods of detecting lipolytic activity in an aqueous assay sample.

In some embodiments, the present disclosure provides a method of detecting lipolytic activity in an aqueous assay sample, the method comprising (a) combining the aqueous assay sample comprising a protein preparation with an organic solvent comprising 4-methylumbelliferyl oleate (4MuO); and (b) measuring the formation of oleate and 4-methylumbelliferone (4Mu) by fluorescence.

In some embodiments, the aqueous assay sample is an aqueous assay sample described herein. In some embodiments, the aqueous assay sample has a pH of 5.0 to 7.0.

In some embodiments, the aqueous assay sample further comprises a buffering agent, a salt, or both, as described herein. Examples of buffering agents and salts and concentrations thereof suitable for the present methods are also provided herein. In some embodiments, the salt is sodium chloride (NaCl), calcium chloride ($CaCl_2$), or combinations thereof. In some embodiments, the salt is sodium chloride and calcium chloride. In some embodiments, the sodium chloride is about 50 mM to about 400 mM in the aqueous assay sample. In some embodiments, the sodium chloride is about 100 mM to about 200 mM in the aqueous assay sample. In some embodiments, the calcium chloride is about 0.2 mM to about 10 mM in the aqueous assay sample. In some embodiments, the calcium chloride is about 1.0 mM to about 2.0 mM in the aqueous assay sample.

In some embodiments, the buffering agent has a buffering capacity at about pH 6.0. In some embodiments, the buffering agent is Tris. In some embodiments, the buffering agent is Bis-Tris. In some embodiments, the buffering agent is about 2 mM to about 200 mM in the aqueous assay sample. In some embodiments, the buffering agent is about 10 mM to about 100 mM in the aqueous assay sample. In some embodiments, the buffering agent is about 40 mM to about 60 mM in the aqueous assay sample. In some embodiments, the buffering agent is about 45 mM to about 55 mM in the aqueous assay sample.

In some embodiments, the protein preparation is a protein preparation described herein. In some embodiments, the protein preparation is a cell culture supernatant. In some embodiments, the protein preparation is a partially purified protein preparation. In some embodiments, the protein preparation is a purified protein preparation. Protein preparations purified to varying degrees, e.g., cell culture supernatant, partially purified protein preparation, and purified protein preparation, are described herein. In some embodiments, the protein preparation comprises a therapeutic protein, e.g., a therapeutic protein described herein. The methods of the present disclosure advantageously allow simple and efficient determination of lipolytic activity in a protein preparation throughout the purification process thereof. For example, the lipolytic activity of a cell culture supernatant (or subsequent purification process product) can be measured using the present methods to determine whether it is necessary to remove lipases during subsequent purification steps. Advantageously, the present methods can be used on products throughout the purification process in order to determine whether lipolytic activity in the protein preparation has been properly abolished.

In some embodiments, the protein preparation comprises additional host cell proteins. In some embodiments, the additional host cell proteins comprise a lipase. Lipases are described herein.

In some embodiments, the protein preparation comprises a surfactant, e.g., a surfactant described herein. In some embodiments, the surfactant is a polysorbate. In some embodiments, the polysorbate is polysorbate 20, polysorbate 80, or combination thereof.

In some embodiments, the organic solvent is an organic solvent described herein. In some embodiments, the organic solvent is an alcohol, a sulfoxide, a nitrile, or combination thereof. In some embodiments, the organic solvent is dimethyl sulfoxide (DMSO). In some embodiments, the organic solvent comprises acetonitrile. In some embodiments, the organic solvent comprises an alcohol. In some embodiments, the organic solvent is a $C_1$-$C_6$ alcohol. In some embodiments, the organic solvent is methanol, ethanol, propanol, iso-propanol, butanol, sec-butanol, tert-butanol, or combination thereof. In some embodiments, the organic solvent comprises a mixture of acetonitrile and isopropanol.

In some embodiments, the acetonitrile and isopropanol are mixed at a ratio of about 3:1.

In some embodiments, the organic solvent comprises 4-methylumbelliferyl oleate (4MuO). The structure of 4MuO is provided herein. In some embodiments, 4MuO hydrolyzes to form oleic acid and 4-methylumbelliferone (4Mu), as described, e.g., in Scheme I. The structure of 4Mu is provided herein. In some embodiments, 4Mu is fluorescent. In some embodiments, 4Mu fluorescence is measured at about 330 nm excitation and 495 mm emission.

In some embodiments, the method comprises measuring fluorescence for up to 24 hours. In some embodiments, the fluorescence is measured for about 24 hours to about 400 hours. In some embodiments, the fluorescence is measured for greater than about 24 hours. In some embodiments, the fluorescence is measured for greater than about 100 hours. In some embodiments, the fluorescence is measured for greater than about 300 hours. It should be understood that the fluorescence measurement is not necessarily a continuous measurement, and that the fluorescence can be measured at predetermined time points. In some embodiments, the fluorescence is measured at selected time points between about 12 hours to about 400 hours. In some embodiments, the fluorescence is measured at a time point of about 24 hours, about 48 hours, about 72 hours, about 96 hours, about 120 hours, about 144 hours, about 168 hours, about 192 hours, about 216 hours, about 240 hours, about 264 hours, about 288 hours, about 312 hours, about 336 hours, about 360 hours, about 384 hours, or about 400 hours. The period of time for which fluorescence is measured can be chosen on the level of lipase activity in the protein preparation. For example, low levels of lipolytic activity may require a longer period of detection due to slower hydrolysis of 4MuO.

In some embodiments, a protein preparation comprising a therapeutic protein is purified, then stored for a period of time (e.g., for less than 4 hours, less than 8 hours, less than 1 day, about 1 day, about 2 days, about 3 days, about 4 days, about 5 days, about 6 days, about 1 week, greater than 1 week, about 2 weeks, greater than 2 weeks, about 3 weeks, greater than 3 weeks, about 1 month, greater than 1 month, about 2 months, greater than 2 months, about 3 months, or greater than 3 months). The protein preparation is then subjected to the present method to detect lipolytic activity.

In some embodiments, the aqueous assay sample and the organic solvent are combined at a ratio of about 70:30 to about 99:1. In some embodiments, the aqueous assay sample and the organic solvent are combined at a ratio of about 75:25 to about 99:1. In some embodiments, the aqueous assay sample and the organic solvent are combined at a ratio of about 80:20 to about 98:2. In some embodiments, the aqueous assay sample and the organic solvent are combined at a ratio of about 85:15 to about 98:2. In some embodiments, the aqueous assay sample and the organic solvent are combined at a ratio of about 90:10 to about 98:2. In some embodiments, the aqueous assay sample and the organic solvent are combined at a ratio of about 95:5 to about 98:2.

In some embodiments, the aqueous assay sample is incubated with a lipase inhibitor for about 10 minutes to about 1 hour prior to step (a), combining the aqueous assay sample comprising the protein preparation and the organic solvent. In some embodiments, the aqueous assay sample is incubated with a lipase inhibitor for about 15 minutes to about 45 minutes, for about 20 minutes to about 40 minutes, or for about 30 minutes prior to step (a). In some embodiments, incubation of the aqueous assay sample with a lipase inhibitor reduces or abolishes lipolytic activity. In some embodiments, incubation of the aqueous assay sample with a lipase inhibitor provides a negative control for the detection of lipolytic activity. In embodiments wherein the aqueous assay sample is incubated with a lipase inhibitor prior to step (a), the measured fluorescence is expected to be low, i.e., indicating low or lack of lipolytic activity. Lipase inhibitors are described herein. In some embodiments, the lipase inhibitor is (S)-2-formylamino-4-methyl-pentanoic acid (S)-1-[[(2S,3S)-3-hexyl-4-oxo-2-oxetanyl]methyl]-dodecyl ester (orlistat). In some embodiments, the lipase inhibitor is about 1 μM to about 50 μM in the composition. In some embodiments, the lipase inhibitor is about 5 μM to about 25 μM in the composition.

In some embodiments, a control sample is measured in parallel with an aqueous assay sample for lipolytic activity. In some embodiments, the present disclosure provides a method of detecting lipolytic activity in an aqueous assay sample, the method comprising (a) combining the aqueous assay sample comprising a protein preparation, with an organic solvent comprising 4-methylumbelliferyl oleate (4MuO) to form an assay composition; (b) combining a control sample comprising a protein preparation and a lipase inhibitor, with an organic solvent comprising 4-methylumbelliferyl oleate (4MuO) to form a control composition; and (c) measuring the formation of oleate and 4-methylumbelliferone (4Mu) by fluorescence in the assay composition and in the control composition. In some embodiments, the protein preparation of (a) and the protein preparation of (b) are provided from the same protein preparation. For example, a protein preparation from a cell culture is obtained from which two aliquots can be removed. One aliquot can be the protein preparation of the aqueous assay sample, and the other aliquot can be the protein preparation of the control sample. In some embodiments, the protein preparation of (a) and the protein preparation of (b) comprise substantially the same components. In some embodiments, the protein preparation of (a) and the protein preparation of (b) are expected to have the same level of lipolytic activity. In some embodiments, the aqueous assay sample and the control sample have substantially the same components except for the lipase inhibitor in the control sample. In some embodiments, the control sample comprising the lipase inhibitor is a negative control sample, i.e., no fluorescence is expected to be detected. In some embodiments, the method further utilizes a positive control sample, i.e., wherein fluorescence is expected. In some embodiments, a positive control sample comprises a known quantity of 4Mu. In some embodiments, a positive control sample comprises a known quantity of 4MuO and a known quantity of an active lipase.

As discussed herein, a lipase having lipolytic activity can interfere with components of a protein preparation. In some embodiments, a lipase having lipolytic activity hydrolyzes fatty acids and/or esters present in a protein preparation. In some embodiments, a lipase having lipolytic activity hydrolyzes a surfactant present in a protein preparation. In some embodiments, hydrolysis of the surfactant reduces stability of the protein preparation. By measuring the amount of lipolytic activity using the methods provided herein, the level of hydrolysis that has occurred in the protein preparation can then be determined based on the measured amount of lipolytic activity, thereby determining the stability of the protein preparation. In some embodiments, the present disclosure provides a method of determining stability of a protein preparation, comprising (a) combining an aqueous assay sample comprising a protein preparation with an organic solvent comprising 4-methylumbelliferyl oleate (4MuO); (b) measuring the formation of oleate and 4-methylumbelliferone (4Mu) by fluorescence; and (c) determining the stability of the protein preparation based on the measured fluorescence. For example, increased fluorescence, relative to a control, would indicate the presence of lipases, indicating that excipients, e.g., surfactants such as polysorbate, have been hydrolyzed, thereby forming non-polar, and therefore insoluble, long chain fatty acids that may destabilize the protein in the protein preparation. In some embodiments, the method is used to determine the stability of a protein preparation for a pharmaceutical formulation.

In some embodiments, the disclosure provides for kits suitable for providing the compositions of the present invention. In some embodiments, the disclosure provides for a kit which can be used to accomplish the methods of the present invention. For example, in some embodiments, the present disclosure further provides a kit comprising, in two or more containers: (a) an organic solvent; (b) 4-methylumbelliferyl oleate (4MuO); and (c) a lipase inhibitor.

Any suitable container can be used in the kits described herein. In some embodiments, the container is a vial. In some embodiments, the container is a bottle. In some embodiments, each container is a compartment of a multi-compartment container. In some embodiments, the organic solvent and the 4MuO are in a first container, and the lipase inhibitor is in a second container. In some embodiments, the organic solvent and the lipase inhibitor are in a first container, and the 4MuO is in a second container. In some embodiments, the lipase inhibitor and the 4MuO are in a first container, and the organic solvent is in a second container. In some embodiments, the lipase inhibitor and the organic solvent are in a first container, and the 4MuO and the organic solvent are in a second container. In some embodiments, the 4MuO is provided as a solid, e.g., a powder. In some embodiments, the 4MuO is provided in solution, e.g., in the organic solvent. In some embodiments, the lipase inhibitor is provided as a solid, e.g., a powder such as a lyophilized powder. In some embodiments, the lipase inhibitor is provided in solution, e.g., in the organic solvent. In any of the above embodiments, the (a) an organic solvent; (b) 4-methylumbelliferyl oleate (4MuO); and/or (c) a lipase inhibitor can be include in their respective containers to receive a predetermined specific amount of protein preparation, wherein the amount of each component is sufficient to practice the method of determining lipolytic activity described herein. In some embodiments, the kit further comprises instructions for utilizing the kit to determine lipolytic activity as in the methods described herein.

In some embodiments, the kit further comprises a buffering agent, a salt, or both. Suitable buffering agents and salts are described herein. In some embodiments, a user of the kit provides a protein preparation for use with the kit. In some embodiments, the protein preparation of the user is in a buffer unsuitable for use with the kit, e.g., a buffer that promotes auto-hydrolysis of the 4MuO and/or degradation of the lipase inhibitor. In some embodiments, the kit provides a buffer exchange column. In some embodiments, the buffer exchange column exchanges the buffer of the user's protein preparation into a buffer suitable for use with the kits provided herein. Examples of buffer exchange columns include, but are not limited to, ZEBA columns from THERMO FISHER, PD-10, SEPHADEX, HIPREP, and HITRAP columns from GE HEALTHCARE, VIVAFLOW and VIVASPIN concentrators from SARTORIUS, BIO-SPIN and ECONO columns from BIO-RAD, and SPINOUT columns from G-BIOSCIENCES.

The column of the kit described herein can be used to exchange the buffer system. Columns used for this purpose are known to the skilled artisan. For example, the column could be used to exchange the buffer in a protein preparation to a buffer more suitable to practice the methods of determining lipolytic activity as described herein.

In some embodiments, the present disclosure provides a kit comprising: (a) an organic solvent comprising 4-methylumbelliferyl oleate (4MuO); (b) a column suitable for exchanging buffer of a protein preparation; and (c) a lipase inhibitor.

Suitable organic solvents for kits of the present disclosure include organic solvents described herein. In some embodiments, the organic solvent is an alcohol, a sulfoxide, a nitrile, or combination thereof. In some embodiments, the organic solvent is dimethyl sulfoxide (DMSO). In some embodiments, the organic solvent comprises acetonitrile. In some embodiments, the organic solvent comprises an alcohol. In some embodiments, the organic solvent is a $C_1$-$C_6$ alcohol. In some embodiments, the organic solvent is methanol, ethanol, propanol, iso-propanol, butanol, sec-butanol, iso-butanol, tert-butanol, or combinations thereof. In some embodiments, the organic solvent comprises a mixture of acetonitrile and isopropyl alcohol.

Suitable lipase inhibitors for kits of the present disclosure include lipase inhibitors described herein. In some embodiments, the lipase inhibitor is (S)-2-formylamino-4-methyl-pentanoic acid (S)-1-[[(2S,3S)-3-hexyl-4-oxo-2-oxetanyl]methyl]-dodecyl ester (orlistat). In some embodiments, the lipase inhibitor is used as a control when practicing the method of determining lipolytic activity as described herein.

Suitable salts for kits of the present disclosure include salts described herein. In some embodiments, the salt is sodium chloride, calcium chloride or combinations thereof. In some embodiments, the salt is sodium chloride and calcium chloride.

Suitable buffering agents for kits of the present disclosure include buffering agents described herein. In some embodiments, the buffering agent is Tris. In some embodiments, the buffering agent is Bis-Tris.

In some embodiments, the kit further comprises instructions for performing an assay to determine lipolytic activity. In some embodiments, the assay comprises a method described herein.

All references cited herein, including patents, patent applications, papers, textbooks and the like, and the references cited therein, to the extent that they are not already, are hereby incorporated herein by reference in their entirety.

EXAMPLES

Chemicals and reagents for the experiments described herein are as follows:

2-propanol (IPA, 99.9%), acetonitrile (ACN, HPLC Plus, ≥99.9%), calcium chloride (≥97%), Triton X-100 (laboratory grade), sodium phosphate monobasic monohydrate (ACS reagent, ≥95%), dimethyl sulfoxide (DMSO, Reagent Plus, ≥99.5%), were obtained from Sigma-Aldrich (now Merck KGaA). 4-methylumbelliferone (4Mu, ≥98%) and N-phenyl-1-naphtylamine (NPN, reagent grade, 98%) were obtained from Aldrich. Sodium chloride (Bioreagent, ≥99%), TRIZMA® hydrochloride (reagent grade, 99.0%), TRIZMA® base (Primary Standard and Buffer, ≥99.9%), Lipase from Porcine pancreas (PPL, Type II, 100-500 U/mg), BIS-TRIS hydrochloride (≥99.0% (titration)), 4-Methylumbelliferyl oleate (4MuO, suitable for fluorescence, ≥95% (HPCE)) and KOLLIPHOR® P 188 (suitable for cell culture) was obtained from Sigma. Acetonitrile (LC-MS grade) was obtained from Thermo Fisher. Ethanol (EtOH, gradient grade for liquid chromatography) and hydrochloric acid 25% v/v was obtained from Merck. Sucrose (USP/NF, EP, JP, high purity) was obtained from Pfanstiehl. Sodium hydroxide 1M solution was obtained from Honeywell Fluka™. Sodium chloride (USP, multi compendial), L-histidine (USP, multi compendial), L-histidine monohydrochloride (FCC, multi compendial), PS20 (NF) and PS80 (NF) were obtained from J.T. Baker. Highly purified water, in the following named 'water' was prepared by using a water purification system (Barnstead™ GenPure™ Pro, Thermo Fisher). pH was measured using a pH meter (780 pH Meter, Metrohm) and Pt pH electrode (Unitrode Pt1000, Metrohm). Cell culture harvest fluid (CCHF) containing a mixture of lipases as part of the HCPs, produced from a proprietary CHO cell line expressing a non-therapeutic monoclonal antibody (mAb 1), as well as mAb 1, were obtained from Lonza Biologics, Slough, UK.

Example 1A

Lipase Assay Development I: pH

A lipase assay was developed based on a method described in Kurihara et al., Biol Pharm Bull 26: 383-385 (2003), utilizing 4-methylumbelliferyl oleate (4MuO) as substrate for the lipase enzyme.

Porcine pancreas lipase (PPL) was used in the assay development. In this experiment, 500 nM PPL and 4MuO were incubated for 22 hours in one of four different buffer systems and tested for 4MuO fluorescence quenching and auto-hydrolysis: (a) 10.4 mM Tris pH 8.1, (b) 10.4 mM Bis-Tris pH 6, (c) 41.6 mM Bis-Tris pH 6, (d) 104 mM Bis-Tris pH 6.

Figure 1B:
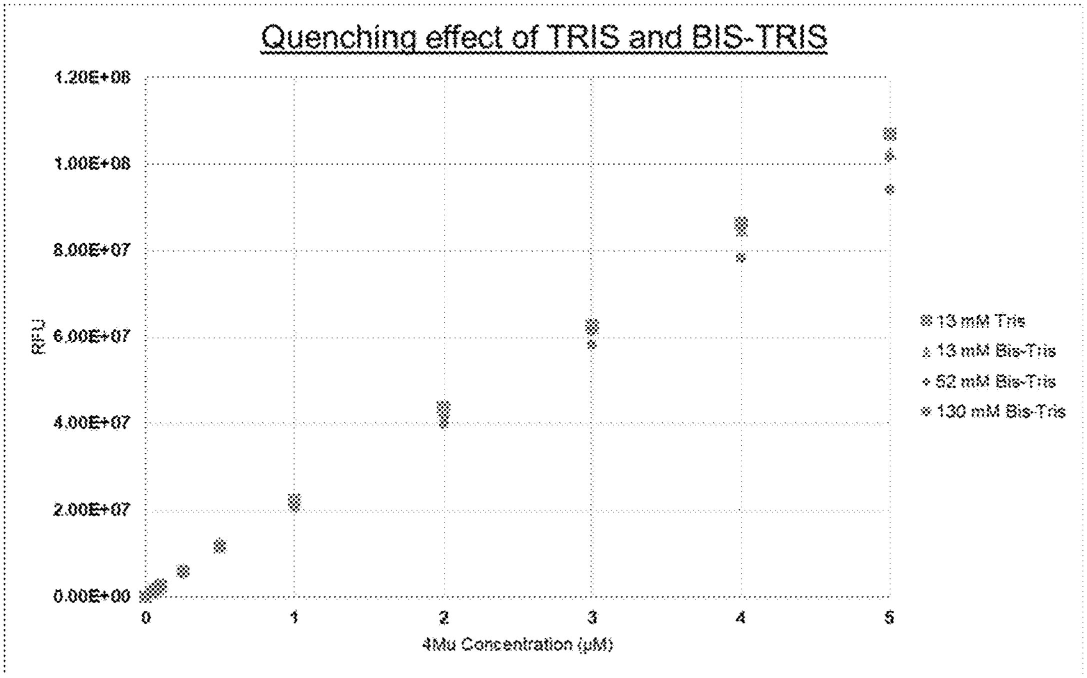
Figure 1C:
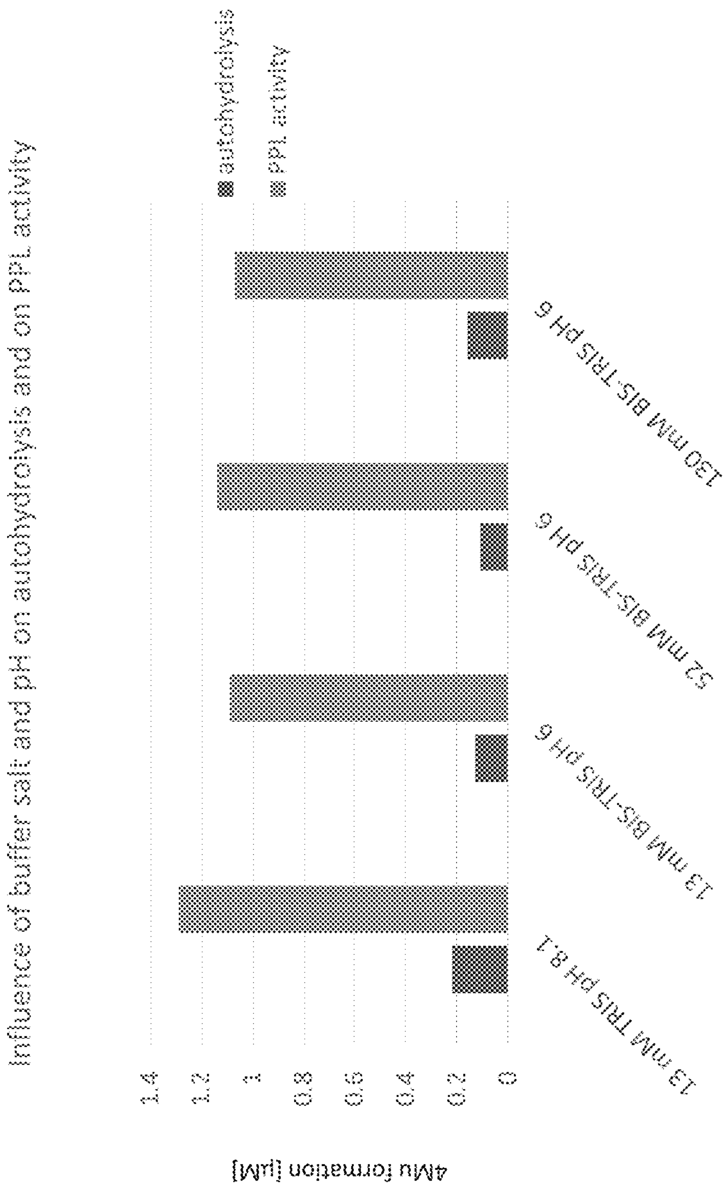

Results in FIGS. 1A-1B and Table 1 show that 4MuO auto-hydrolysis was reduced at pH 6 compared with pH 8. FIG. 1C shows that auto-hydrolysis rate at pH 8 was almost double the rate at pH 6. Lipase was slightly (<20%) more active in pH 8 compared with pH 6. Buffer concentration did not appear to have a strong influence on autohydrolysis and lipase activity. Lipolytic activity appeared to be the highest in 41.6 mM Bis-Tris buffer. Fluorescence quenching was observed in 104 mM Bis-Tris buffer.

TABLE 1

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| 10.4 mM TRIS pH 8.1 | 0.22 | 1.51 | 1.29 |
| 10.4 mM BIS-TRIS pH 6 | 0.13 | 1.22 | 1.09 |
| 41.6 mM BIS-TRIS pH 6 | 0.11 | 1.26 | 1.14 |
| 104 mM BIS-TRIS pH 6 | 0.16 | 1.23 | 1.07 |

Figure 1E:
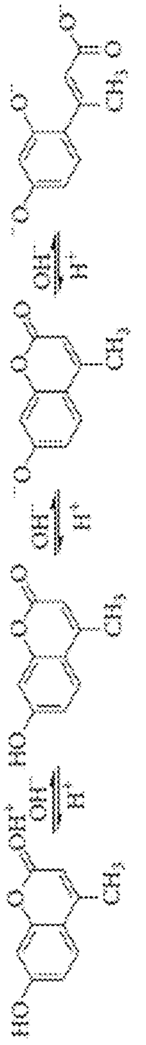
Figure 1D:
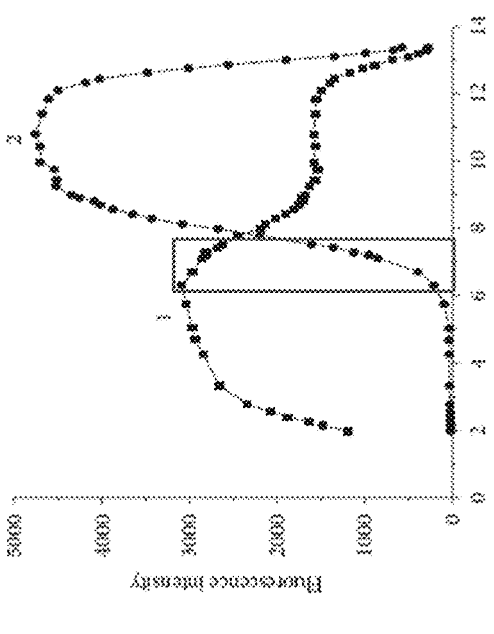

The auto-hydrolysis of 4MuO was further investigated. The pKa of 4Mu is approximately 7.7. FIG. 1D shows the pH range at which 4Mu was measured (graph reproduced from Zhi et al., J Spectrosc 1 (2013) doi:10.1155/2013/147128). FIG. 1E shows the four forms of 4Mu over various pH ranges (reproduced from Zhi et al., 2013). Form II is prevalent and displays its excitation and emission at $\lambda_{ex}$ of 320 nm and $\lambda_{em}$ of 445 nm.

Example 1B

Lipase Assay Development I: pH

Figure 19A:
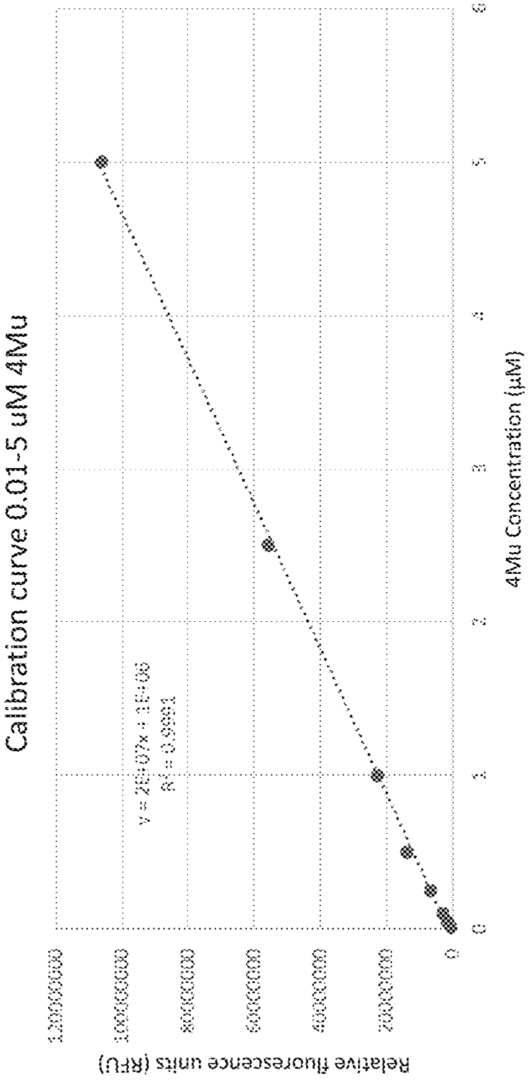

A further study was performed to assess various buffering agents and pH of a lipase assay buffer. The following volume ratios were applied (all v/v): sample (75%), High Concentration Matrix Buffer (HCMB) (20%), organic solvent (5%). The mixtures were incubated in timeframes of about 24 hours to about 300 hours. Assay components were transferred into 96 well plates and analyzed for fluorescent intensity. For 4Mu calibration curves, the reference standard 4Mu was prepared at concentrations of 0 μM, 0.2 μM, 1 μM, 2 μM, 5 μM, 10 μM, 20 μM, 50 μM and 100 μM in the organic solvent and spiked at 5% (v/v) to the final concentrations of 0 μM, 0.1 μM, 0.05 μM, 0.1 μM, 0.25 μM, 0.5 μM, 1 μM, 2.5 μM and 5 μM to the other assay components. It was seen that the slope of the calibration curve slightly shifted from the low calibration range (0.01-0.5 μM) to the high calibration range up to 5 μM. Therefore, quantitative results of 4Mu at a concentration range up to 0.5 μM were calculated with a reduced calibration curve from 0.01-0.5 μM. A 4Mu calibration curve is shown in FIGS. 19A and 19B.

In this study, the "sample" was a placebo formulation buffer that included 20 mM L-histidine, pH 6 (pH adjustment was performed by addition of 25% (w/v) HCl or 1 M NaOH), 250 mM sucrose, 0.5% cell culture harvest fluid (CCHF) or approximately 0.0025 mg/mL porcine pancreatic lipase (PPL). The HCMB included TRIS (208 mM) at pH 7 and 8 or BIS-TRIS (208 mM) at pH 6 (pH adjustment was performed by addition of 25% (w/v) HCl or 1 M NaOH), NaCl (200 mM, 600 mM or 1800 mM), $CaCl_2$ (0.52 mM, 5.2 mM or 52 mM). The organic solvent was either methanol (MeOH), dimethylsulfoxide (DMSO) or isopropanol (IPA), containing 4MuO at 100 μM, and 5% (v/v) organic solvent/substrate were added. Assay components were transferred into 96 well plates and analyzed for fluorescent intensity.

For fluorescent analysis, samples were transferred into 96-well microplates (Thermo Scientific™ Nunc™ F96 MicroWell™ black polystyrene plates). The fluorescence measurement was carried out with the Molecular Devices SpectraMax iD3 microplate reader and the SMP 7.1 software. The maximum excitation ($\lambda_{ex}$) and emission wavelengths ($\lambda_{em}$) were at 330 nm and 495 nm, respectively, after optimization using the SoftMax Pro 7.1 (SMP 7.1) wavelength optimization mode for an intermediate concentration of 4Mu. The fluorescence signal was read in between approximately 24 h to approximately 300 h incubation time, and new 96-well microplates were prepared for each reading by transferring 200 μL of liquid (including sample, HCMB and organic solvent) into each well. Fluorescence measurements were carried out at ambient temperature.

Figure 11:
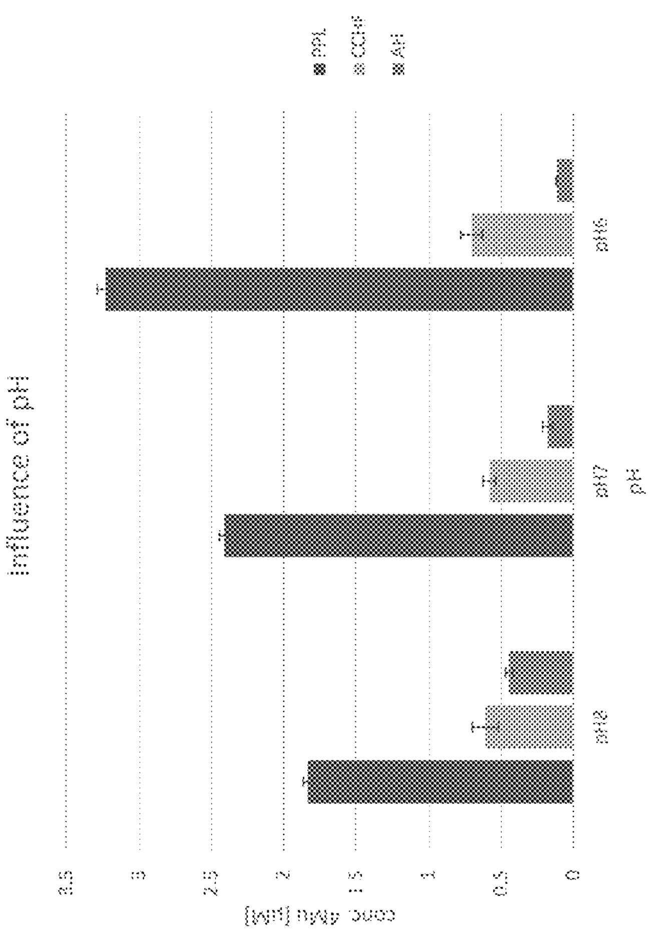
FIG. 11 relates to Example 1B.

Results for the evaluation of the two different buffers (TRIS or BIS-TRIS) at pH 6, pH 7, or pH 8 are shown in FIG. 11. The conversion of 4MuO to 4Mu was measured by monitoring fluorescence intensity of 4Mu. Samples containing either PPL or CCHF, and 4MuO autohydrolysis were evaluated. The most significant impact of the pH modification was observed for autohydrolysis (AH), which decreased by a factor of ~5 when lowering the pH from 8 to 6. The 4Mu concentration in the samples of different pH was measured against calibration curves of 4Mu in reference samples at the same pH, i.e. the observed trend is not due to a different response of 4Mu fluorescence at different pH but is due to different reaction rates. The PPL activity increased almost by a factor of 2 when decreasing the pH from 8 to 6, whereas the CCHF lipolytic activity was not affected. The pH dependency of PPL was previously reported in Li et al., "Adsorption and catalytic activity of Porcine pancreatic lipase on rod-like SBA-15 mesoporous material," *Colloids and Surfaces A: Physicochem Eng Aspects* 2009; 341:79-85. However, this pH dependency may not be identical for any other type of lipase possibly present in HCPs contained in the DS pools. pH 6 was considered most suitable also from the perspective, that many therapeutic protein formulations, where polysorbate degradation was observed and reported, are typically maintained at slightly acidic pH and hence, adaptation of the assay pH to ~6 is assumed to cover the culprits (e.g., lipases) responsible for causing lipase-mediated hydrolytic polysorbate degradation. Therefore, BIS-TRIS at a concentration of 200 mM was selected to be added in the HCMB to yield a final assay concentration of 40 mM at pH 6.

Example 2A

Lipase Assay Development II: $CaCl_2$

The calcium chloride concentration in the lipase assay buffer was investigated. A lipase assay using 500 nM PPL and 4MuO were performed at 3 different $CaCl_2$ concentrations to investigate 4MuO fluorescence quenching and auto-hydrolysis: (a) 0.104 mM $CaCl_2$; (b) 1.04 mM $CaCl_2$; and (c) 10.4 mM $CaCl_2$.

Figure 2A:
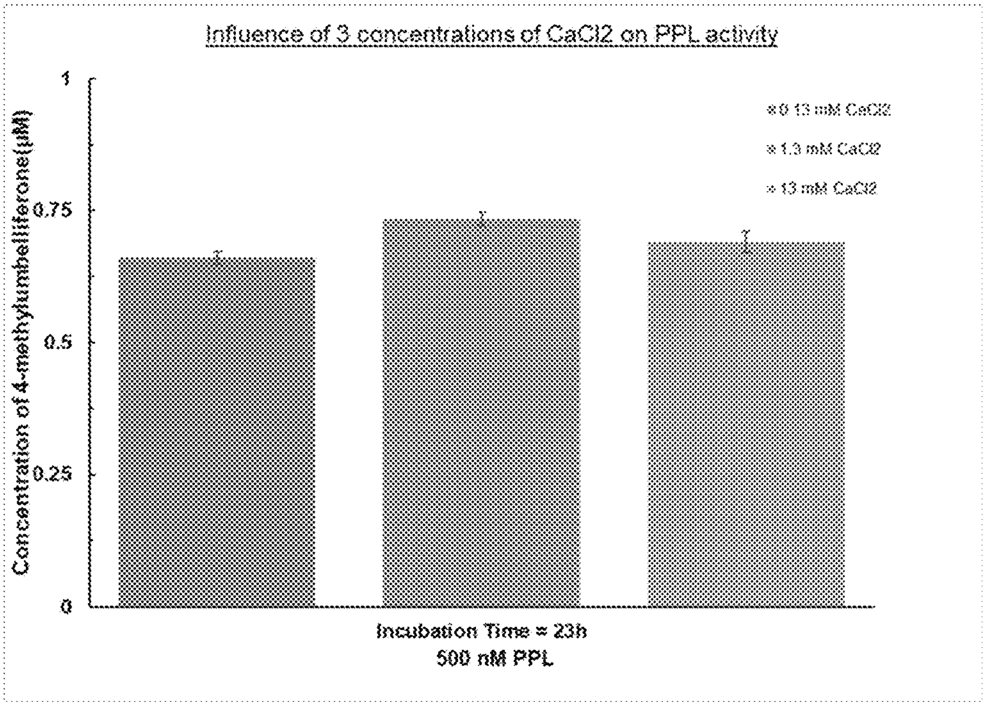
FIGS. 2A-2C relate to Example 2A.
Figure 2B:
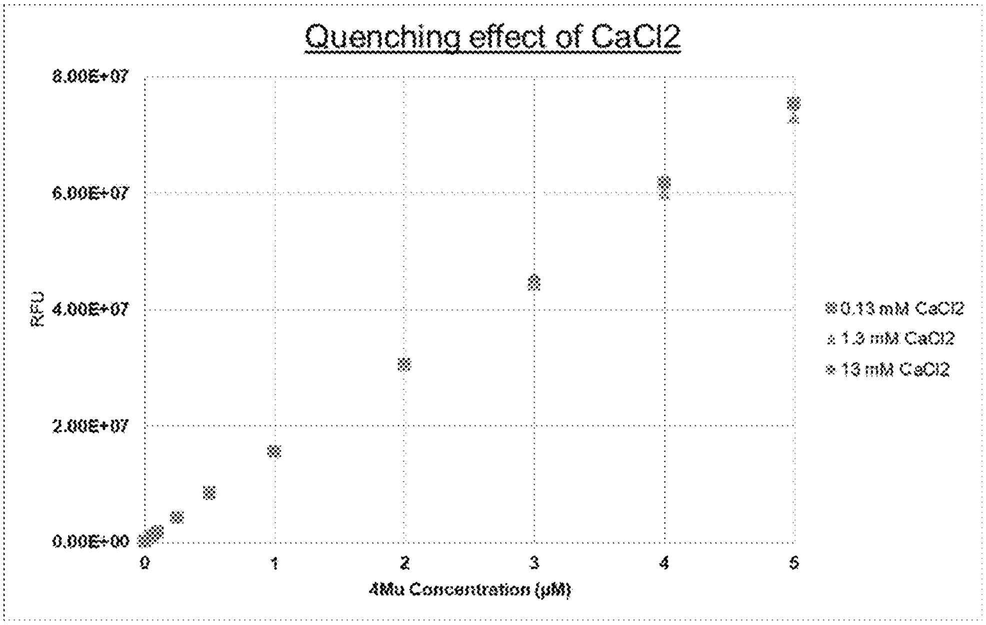
Figure 2C:
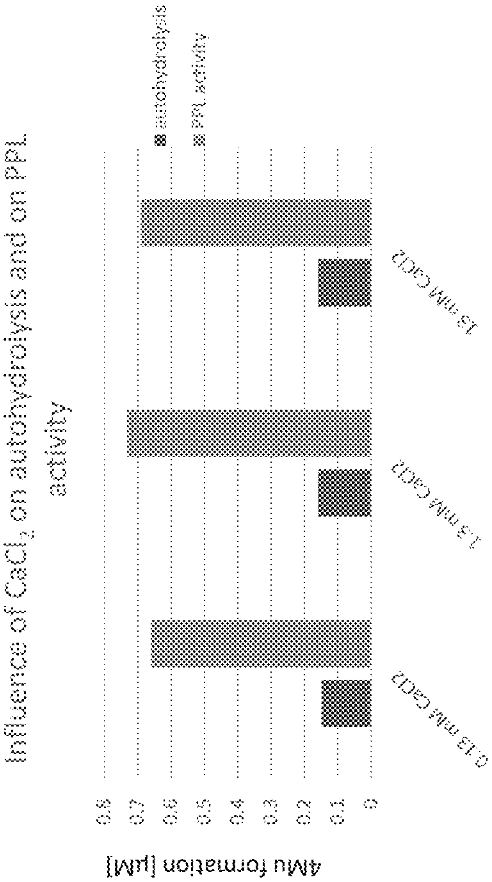

Results in FIGS. 2A-2C and Table 2 show that no 4MuO auto-hydrolysis occurred, and no fluorescence quenching by the chloride anion was observed. Lipase activity was the highest in 1.3 mM $CaCl_2$.

TABLE 2

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| 0.104 mM $CaCl_2$ | 0.15 | 0.81 | 0.66 |
| 1.04 mM $CaCl_2$ | 0.16 | 0.90 | 0.73 |
| 10.4 mM $CaCl_2$ | 0.16 | 0.85 | 0.69 |

Example 2B

Lipase Assay Development II: $CaCl_2$

The calcium chloride concentration in the lipase assay buffer was investigated in a further experiment. The sample, HCBM composition, and experimental procedures were as described in Example 1B, with $CaCl_2$ was included in the HCMB at 0.52 mM, 5.2 mM, or 52 mM as described in Example 1B.

Figure 12:
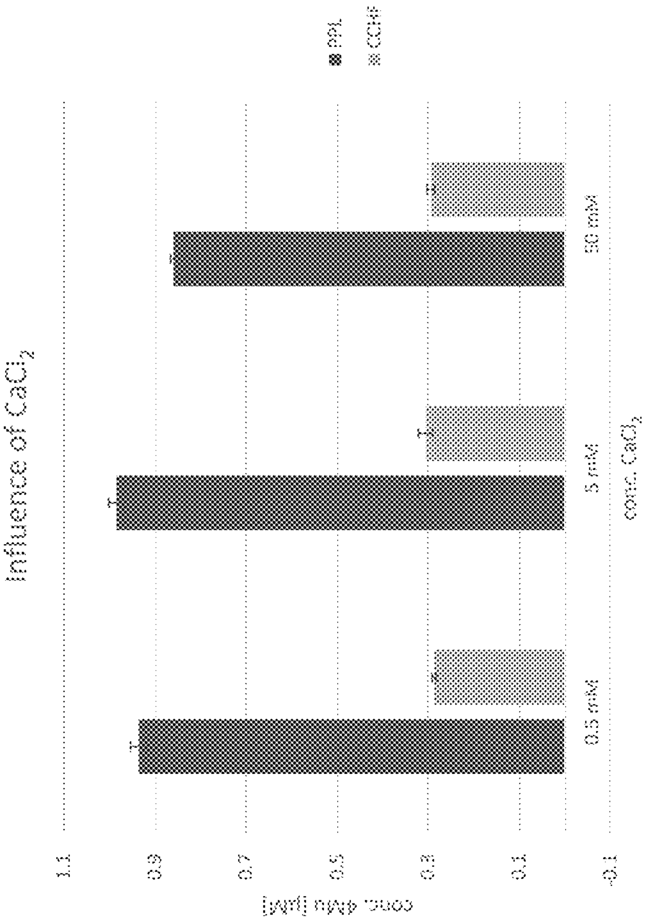
FIG. 12 relates to Example 2B.

Results for the evaluation of different $CaCl_2$ concentrations in HCMB with samples containing either PPL or CCHF are shown in FIG. 12. It was observed that at the highest concentration of $CaCl_2$, the PPL activity slightly decreased. In consideration of the requirements for the HCMB to establish similar assay conditions for various drug substance/drug product matrices, 5 mM $CaCl_2$ was selected to be added to the HCMB to yield a final assay concentration of 1 mM $CaCl_2$.

Example 3A

Lipase Assay Development III: NaCl

The sodium chloride concentration in the lipase assay buffer was investigated. A lipase assay using 500 nM PPL and 4MuO were performed at 3 different NaCl concentrations to investigate 4MuO fluorescence quenching and auto-hydrolysis: (a) 40 mM NaCl; (b) 120 mM NaCl; and (c) 360 mM NaCl.

Figure 3A:
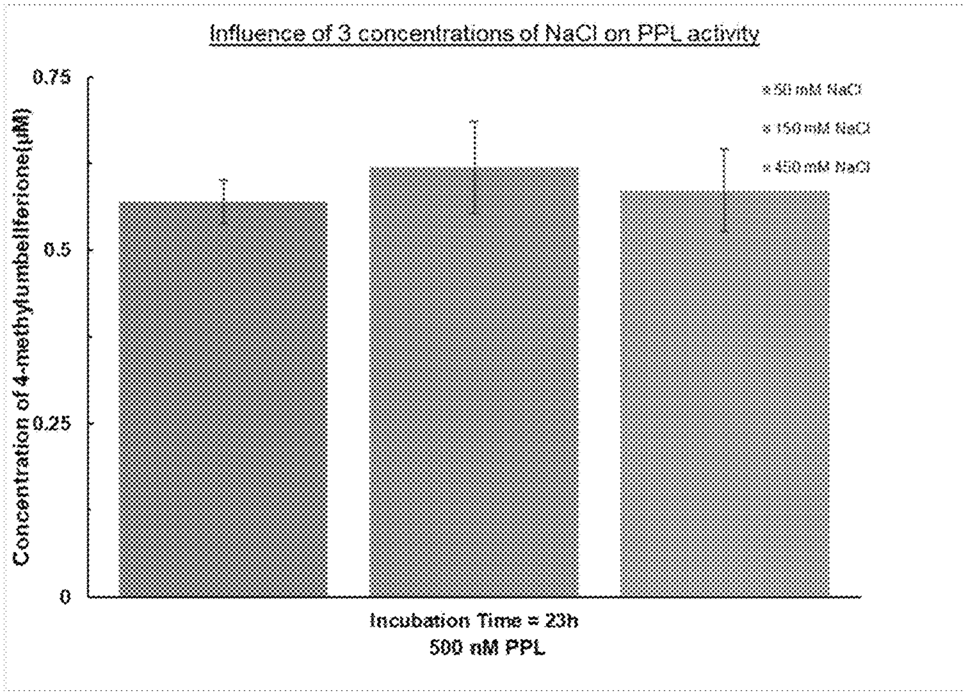
FIGS. 3A-3C relate to Example 3A.
Figure 3B:
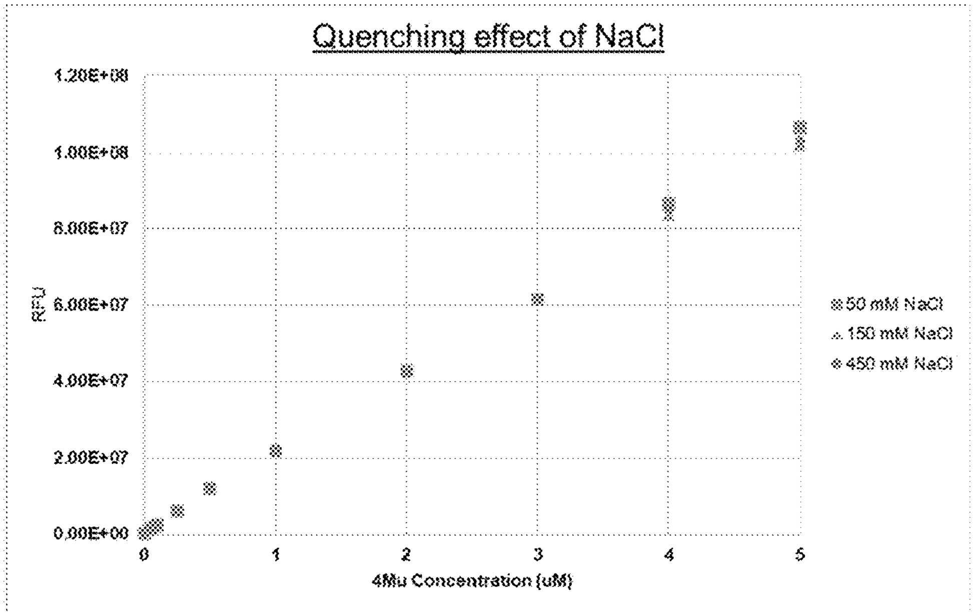
Figure 3C:
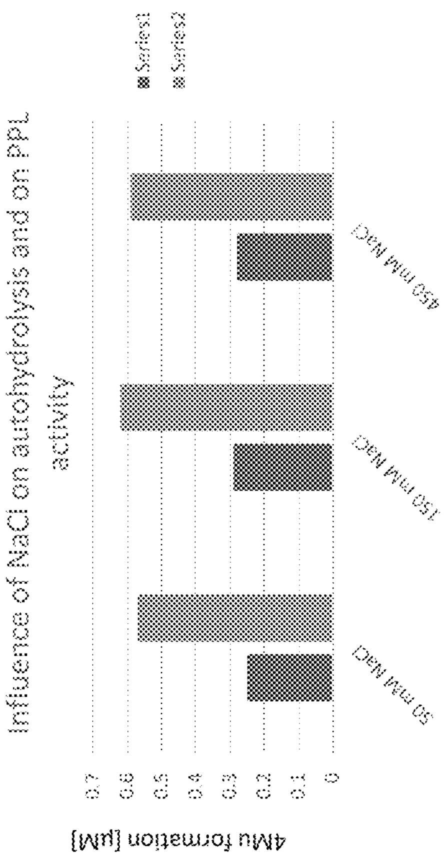

Results in FIGS. 3A-3C and Table 3 show that no 4MuO auto-hydrolysis occurred, and no fluorescence quenching by the chloride anion was observed. Lipase activity was the highest in 120 mM NaCl.

TABLE 3

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| 40 mM NaCl | 0.25 | 0.82 | 0.57 |
| 120 mM NaCl | 0.29 | 0.91 | 0.62 |
| 360 mM NaCl | 0.28 | 0.86 | 0.59 |

Example 3B

Lipase Assay Development III: NaCl

The sodium chloride concentration in the lipase assay buffer was investigated in a further experiment. The sample, HCBM composition, and experimental procedures were as described in Example 1B. NaCl was included in the HCMB at 200 mM, 600 mM, or 1800 mM as described in Example 1B.

Figure 13:
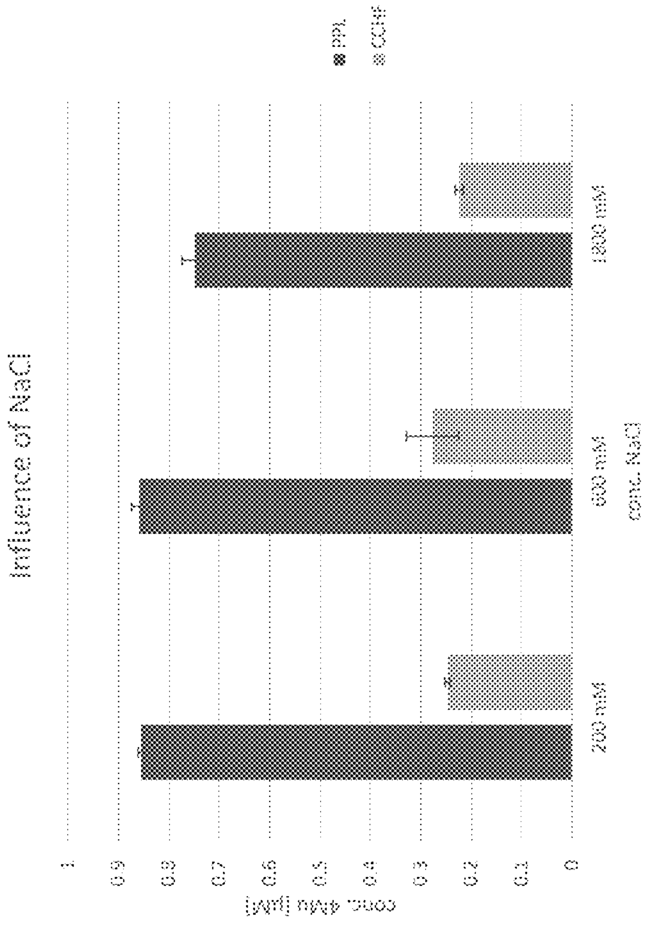
FIG. 13 relates to Example 3B.

Results for the evaluation of different NaCl concentrations in HCMB with samples containing either PPL or CCHF are shown in FIG. 13. It was observed that at the highest concentration of NaCl, the PPL activity slightly decreased. In consideration of the requirements for the HCMB to establish similar assay conditions for various drug substance/drug product matrices, 600 mM NaCl was selected to be added to the HCMB to yield a final assay concentration of 120 mM NaCl.

Example 4A

Lipase Assay Development IV: Organic Solvent

The organic solvent in the lipase assay buffer was investigated. A lipase assay using 500 nM PPL and 4MuO were performed using 3 different organic solvents to investigate 4MuO fluorescence quenching and auto-hydrolysis: (a) DMSO; (b) isopropanol (IPA); and (c) methanol (MeOH).

Figure 4A:
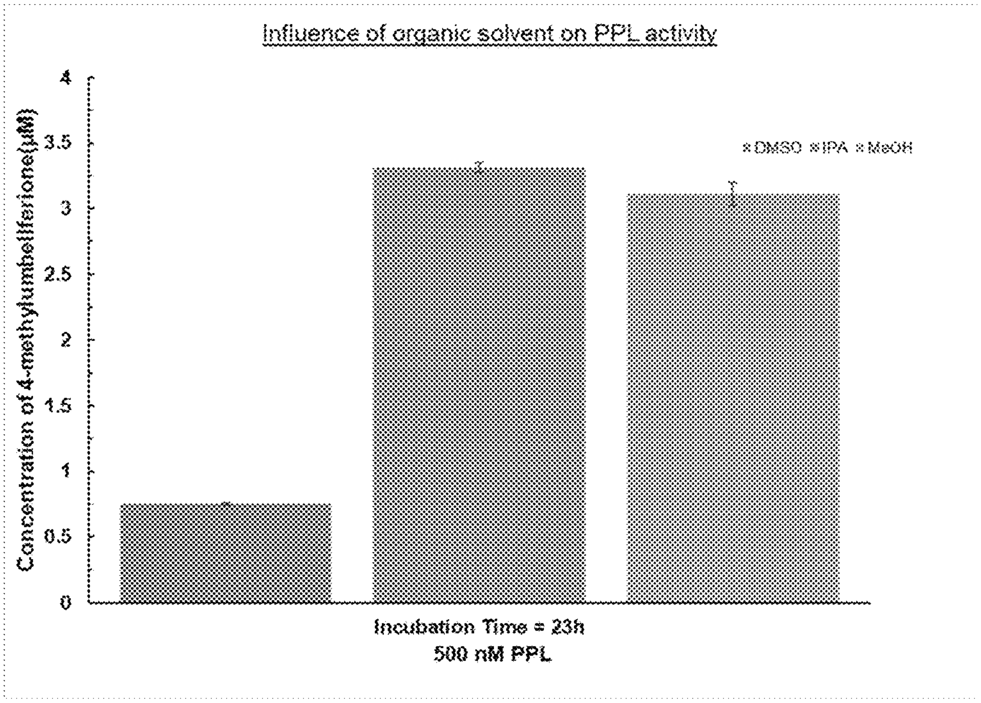
FIGS. 4A-4C relate to Example 4A.
Figure 4B:
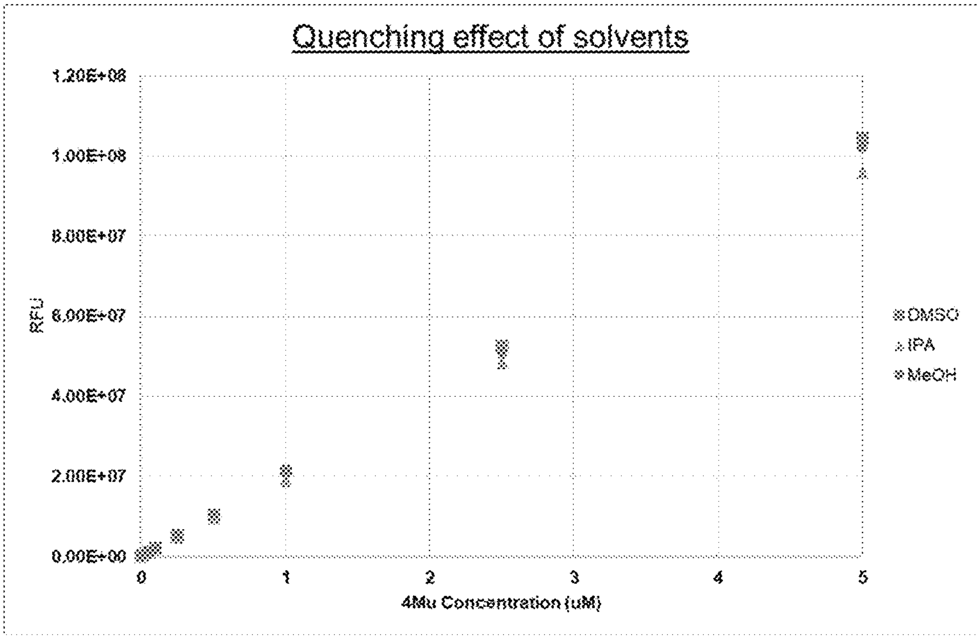
Figure 4C:
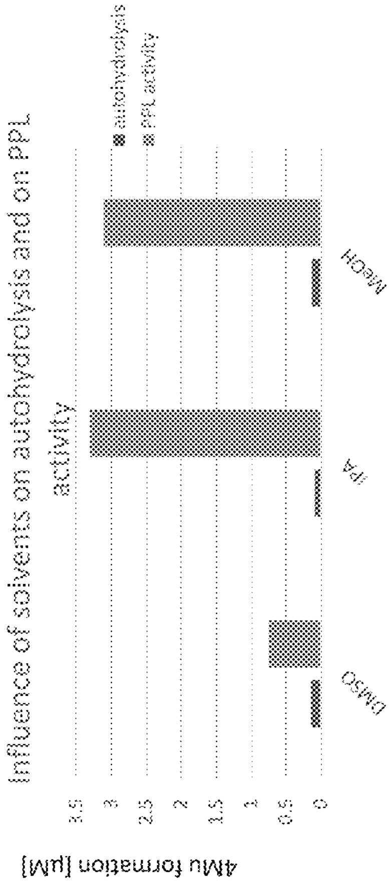

Results in FIGS. 4A-4C and Table 4 show that of the three solvents, the lowest auto-hydrolysis, but slight fluorescent quenching was observed with isopropanol. However, methanol had comparable results. Furthermore, Glogauer et al., Microb Cell Fact 10: 54 (2011) indicate that methanol may have activity enhancing abilities.

TABLE 4

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| DMSO | 0.14 | 0.89 | 0.75 |
| IPA | 0.09 | 3.41 | 3.31 |
| MeOH | 0.13 | 3.24 | 3.11 |

Example 4B

Lipase Assay Development IV: Organic Solvent

The organic solvent in the lipase assay buffer was investigated in a further experiment. The sample, HCBM composition, and experimental procedures were as described in Example 1B. The organic solvents methanol (MeOH), dimethylsulfoxide (DMSO), or isopropanol (IPA) containing 100 μM 4MuO were included in the assay reaction as described in Example 1B.

Figure 14:
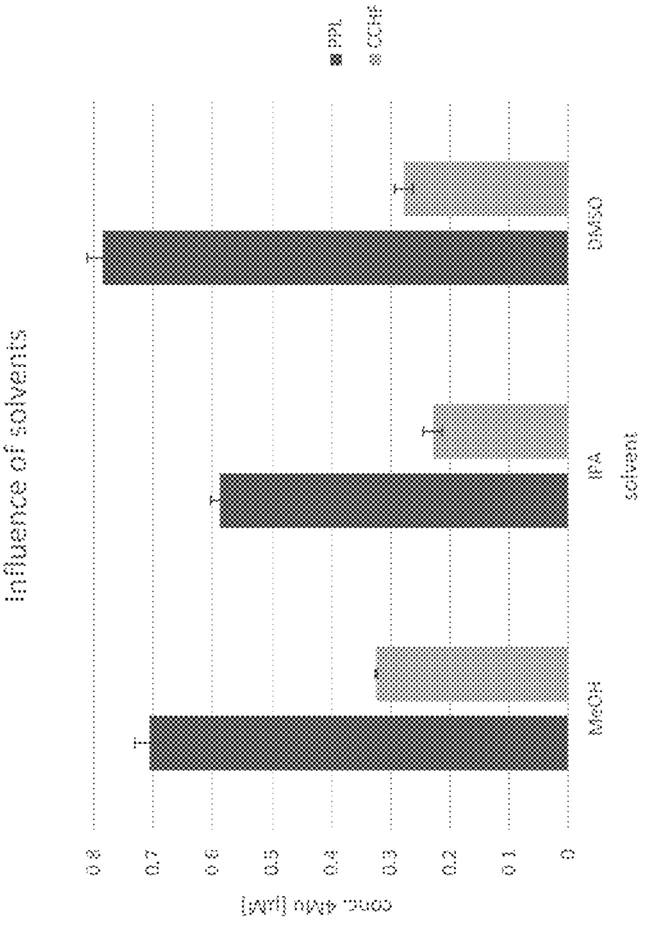
FIG. 14 relates to Example 4B.

Results for the evaluation of different organic solvents with samples containing either PPL or CCHF are shown in FIG. 14. Unlike prior results reported in Glogauer et al., "Identification and characterization of a new true lipase isolated through metagenomic approach," *Microb Cell Fact* 2011; 10:54, which reported a strong influence of different solvents on LipC12 lipase isolated by a metagenomic approach from *E. coli*. In Glogauer et al., MeOH—and, to a lower degree, IPA—showed an activating effect, increasing LipC12 lipase activity by a factor of >10. However, the studied bacterial enzyme likely has very different properties, e.g., as evidenced by a different optimal pH for activity compared with the results in Example 1B. Based on the results in FIG. 14, MeOH was selected to be added to the HCMB.

Example 5A

Lipase Assay Development V: Surfactant

The lipase assay buffer performance in the presence of surfactant was investigated. A lipase assay using 500 nM PPL and 4MuO were performed using 2 surfactants at 2 different concentrations to investigate 4MuO fluorescence quenching and auto-hydrolysis: (a) TRITON X-100 0.012% w/v, (b) TRITON X-100 0.06% w/v, (c) KOLLIPHOR P188 0.032% w/v, and (d) KOLLIPHOR P188 0.16% w/v. A control containing no surfactant was also tested.

Figure 5A:
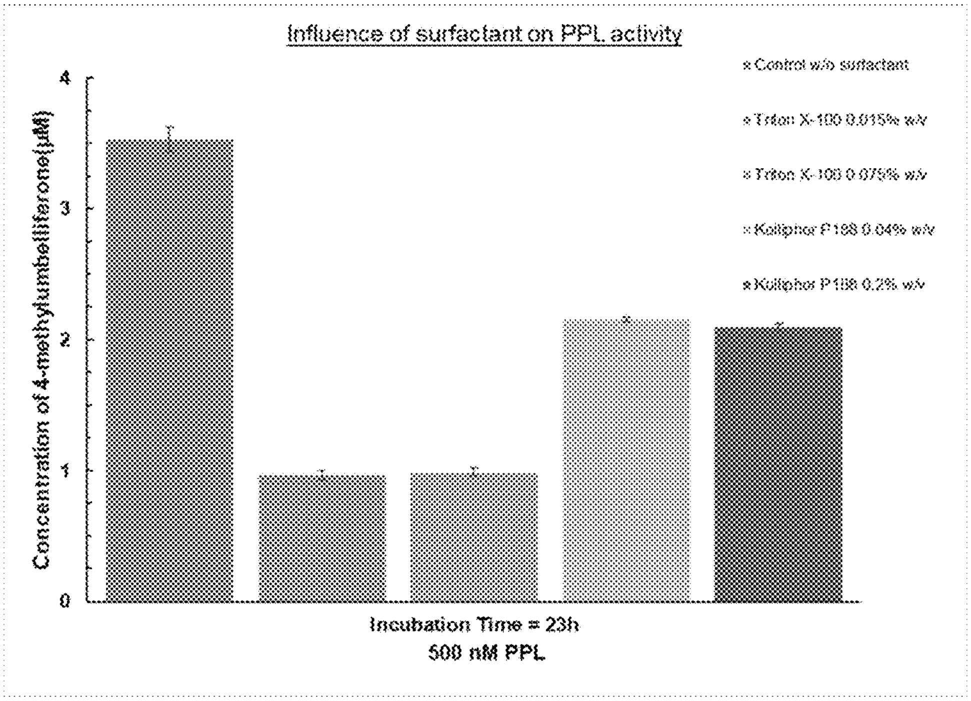
FIGS. 5A-5C relate to Example 5.
Figure 5B:
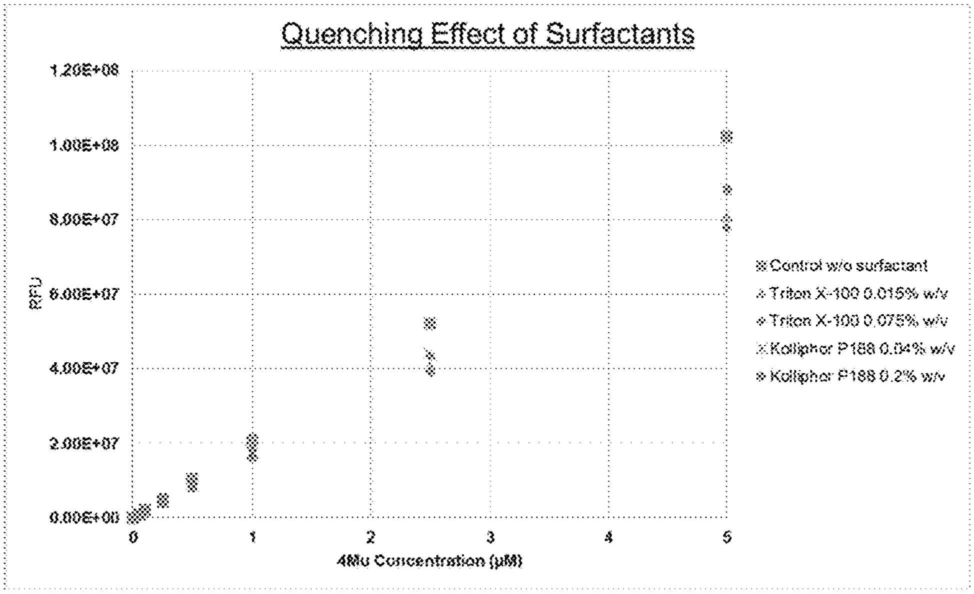
Figure 5C:
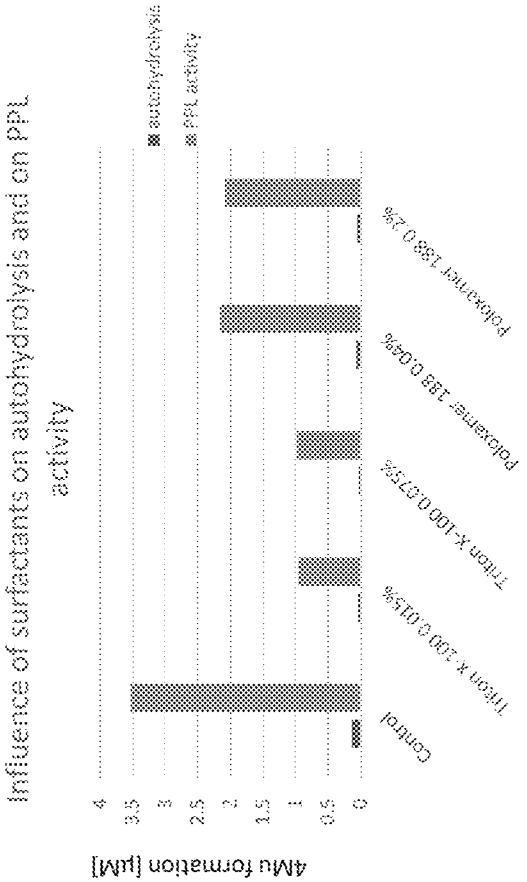

Results in FIGS. 5A-5C and Table 5 show that samples with surfactant had the lowest auto-hydrolysis, but fluorescence quenching was observed. Lipolytic activity also appeared to decrease with surfactant.

TABLE 5

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| Control | 0.14 | 3.67 | 3.53 |
| Triton X-100 0.012% w/v | 0.04 | 1.00 | 0.96 |
| Triton X-100 0.06% w/v | 0.03 | 1.01 | 0.98 |
| Kolliphor P188 0.032% w/v | 0.07 | 2.23 | 2.16 |
| Kolliphor P188 0.16% w/v | 0.06 | 2.15 | 2.09 |

Example 5B

Lipase Assay Development V: Surfactant

A further study was performed to assess the effect of a surfactant on the lipolytic activity of PPL and CCHF. The surfactants polysorbate-20 (PS20) and polysorbate-80 (PS80), which can be found in biopharmaceutical drug product formulations, were evaluated. A poloxamer was also tested, as previous work (Gupta et al., "Simplified para-nitrophenyl palmitate assay for lipases and esterases," *Anal Biochem* 2002; 311: 98-99) suggested that surfactants solubilize poorly soluble substrate such as para-nitrophenyl palmitate.

Samples contained 20 mM L-histidine at pH 6, 250 mM sucrose, a surfactant (either polysorbate-20 (PS20), polysobate-80 (PS80), or poloxamer at 0.02% or 0.06% (all w/v), or as a control not containing a surfactant), 0.5% CCHF or 0.0025 mg/mL PPL. The HCMB contained 208 mM BIS-TRIS at pH 6, 600 mM NaCl, 5.2 mM $CaCl_2$. 5% (v/v) of the organic solvent MeOH containing 100 μM 4MeO were added to the assay. Assay components were transferred into 96 well plates and analyzed for fluorescent intensity as described above for Example 1B.

Figure 15B:
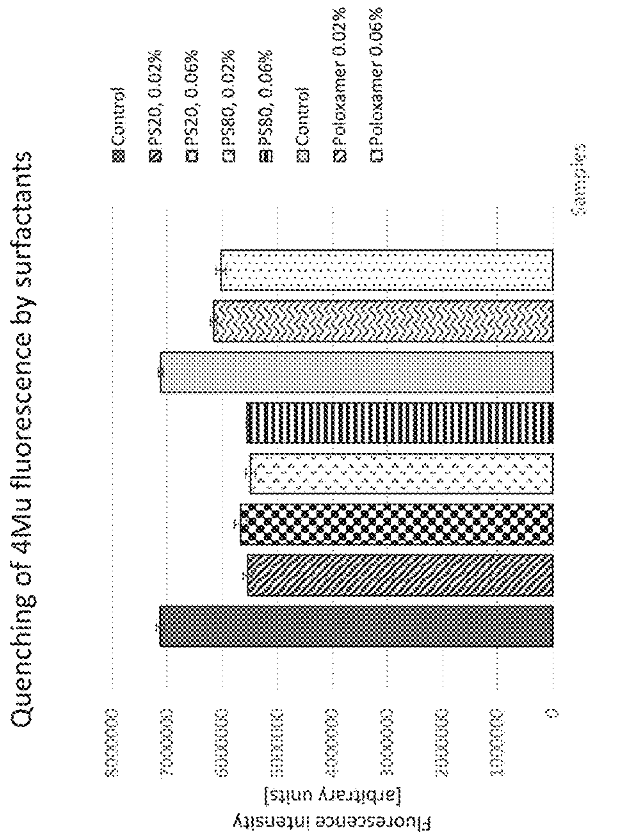
FIGS. 15A and 15B relate to Example 5B.

Results of the effect of surfactants on lipolytic activity are shown in FIG. 15. The presence of the surfactants had a noticeable impact on lipolytic activity. The polysorbates drastically decreased 4Mu formation by >90% for PPL and by ~80% for CCHF, and PS80 decreased 4Mu formation slightly more pronounced compared to PS20.

There are several possible reasons for these observations: (1) the polysorbates, consisting of fatty acid esters, were a competitive substrate/inhibitor for the lipases, and/or (2) the nonpolar substrate 4MuO was incorporated into the micellar structure of polysorbate, thereby being reduced in concentration in the aqueous medium, and hence negatively affecting enzymatic rate constants, which are correlating with substrate concentration (according to e.g. the concept of Michaelis-Menten kinetics), and/or (3) the lipase enzymes were structurally affected, leading potentially to an unfolding and thereby to a decrease in activity.

Interestingly, the concentration of polysorbate appears to have had an effect on CCHF lipolytic activity, with higher polysorbate concentration yielding lower activity, whereas PPL was similarly active at the two different chosen concentrations of both polysorbates. Poloxamer on the other hand influenced lipolytic activity of PPL and CCHF in a very different way. The activity of PPL was reduced to ~50% compared to the control, and—as already seen with the polysorbates—the chosen concentrations of the surfactant did not show a distinct variability in enzyme activity. The lipolytic activity of CCHF was positively influenced by poloxamer, at least at a surfactant concentration of 0.02%, and apparently not affected at a concentration of 0.06%. While not being bound by any particular theory, one reason for the enzymatic behavior in the presence of the surfactants as well as the concentration dependency may be the combination of more than one cause. For example, lipase kinetics and mechanistic investigations are difficult, due to the fact that the enzymes catalyze reactions on substrates that are poorly soluble in water, e.g. triglycerides and other fats. At the water/fat interface the enzymes are activated by movement of a lid domain, which in the closed form protects the active site, whereas in the open form allows access of the substrate to the active site. See, e.g., Lowe, "The triglyceride lipases of the pancreas," *J Lipid Res* 2002; 43(12): 2007-2016.

Figure 15A:
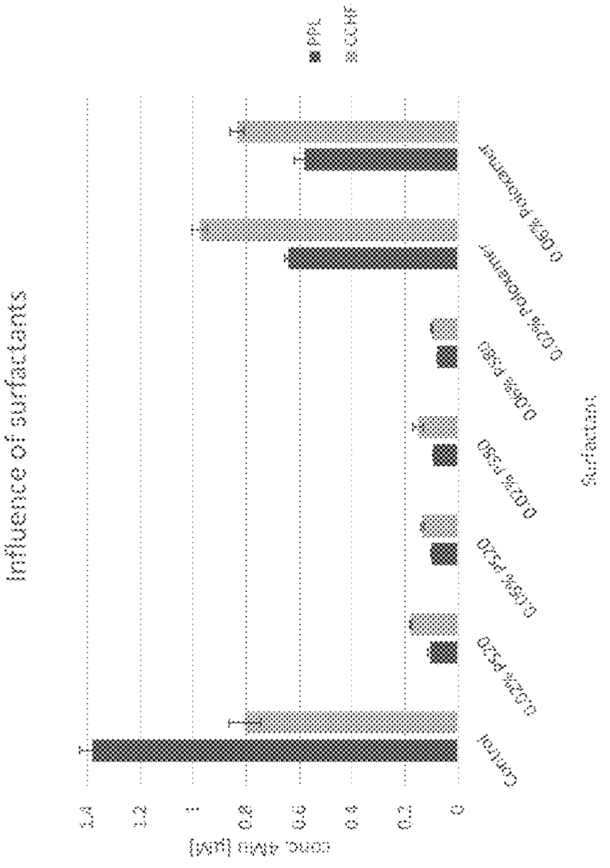

Notably, the polysorbates have a negative impact on lipolytic activity for the model lipase PPL and for CCHF. The fluorescence intensity of the 4Mu hydrolysis product was also influenced (reduced by ~20%) in the presence of the surfactants (see FIG. 15B), which also contributes to the decreased signal intensity of the 4Mu product, as seen in FIG. 15A.

Example 6A

Lipase Assay Development VI: Lipase Inhibitor

The lipase inhibitor orlistat was chosen for the lipase assay control experiments, and thus assay performance was evaluated with different concentrations of the inhibitor. Orlistat was developed as a mechanism based inhibitor to bind covalently to the active site serine of pancreatic lipases, thereby inhibiting the enzymes. This mode of action made it an orally administered medication to treat obesity and related symptoms that are based on gastrointestinal fat hydrolysis. There is no study published that investigated systematically, which lipase classes can be inhibited by orlistat. It was however previously reported that apart from mammalian also bacterial lipases, e.g. the one from *Streptomyces rimosus,* could be inhibited at millimolar orlistat concentration, and that inhibition occurred by covalent modification of the active site serine. See, e.g., Hadvary et al., "The lipase inhibitor tetrahydrolipstatin binds covalently to the putative active site serine of pancreatic lipase," *J Biol Chem* 1991; 266(4):2021-2027; Heck et al., "Orlistat, a new lipase inhibitor for the management of obesity. *Pharmacotherapy* 2000; 20(3):270-279; Asler et al., "Mass spectrometric evidence of covalently-bound tetrahydrolipstatin at the catalytic serine of *Streptomyces rimosus* lipase," *Biochim Biophys Acta.* 2007; 1770:163-170. In such previous studies, a large volume ratio of 50% (v/v) organic solvent in the final assay was necessary to introduce the hydrophobic inhibitor at this high concentration. As such high organic solvent concentration was not foreseen in the current lipase assay due to potential impairment with the other assay components, e.g. precipitation of the pharmaceutically active protein, it was opted to use lower solvent—and also inhibitor—concentrations. This should not necessarily negatively impact the assay readout, because mammalian lipases were found to be inhibited at much lower, i.e. nanomolar, orlistat concentration. See, e.g., Lewis et al., "Direct measurement of lipase inhibition by Orlistat using a dissolution linked in vitro assay," *Clin Pharmacol Biopharm* 2012; 1(3): 1-3.

Lipase activity was tested after co- and pre-treatment of a sample containing 500 nM PPL with orlistat (lipase inhibitor) at 3 concentrations to investigate 4MuO fluorescence quenching and auto-hydrolysis: (a) co-treatment 25 μM orlistat, (b) co-treatment 15 μM orlistat, (c) co-treatment 5 μM orlistat, (d) pre-treatment 25 μM orlistat, (e) pre-treatment 15 μM orlistat, and (f) pre-treatment 5 μM orlistat. A control sample with no orlistat was also tested.

Figure 6A:
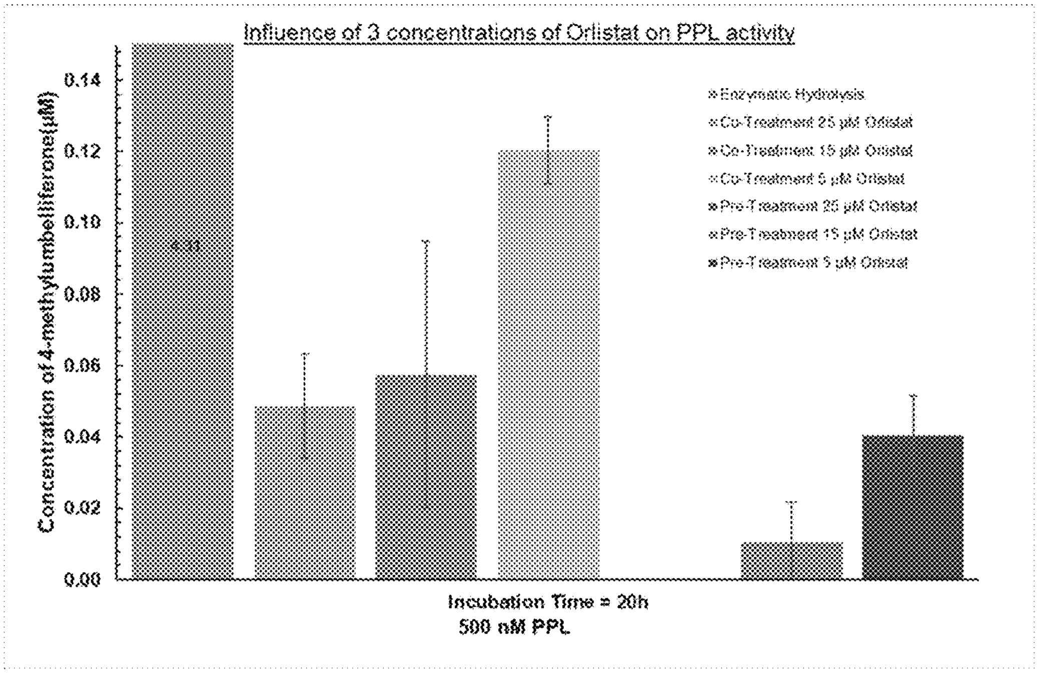
FIGS. 6A-6B relate to Example 6.
Figure 6B:
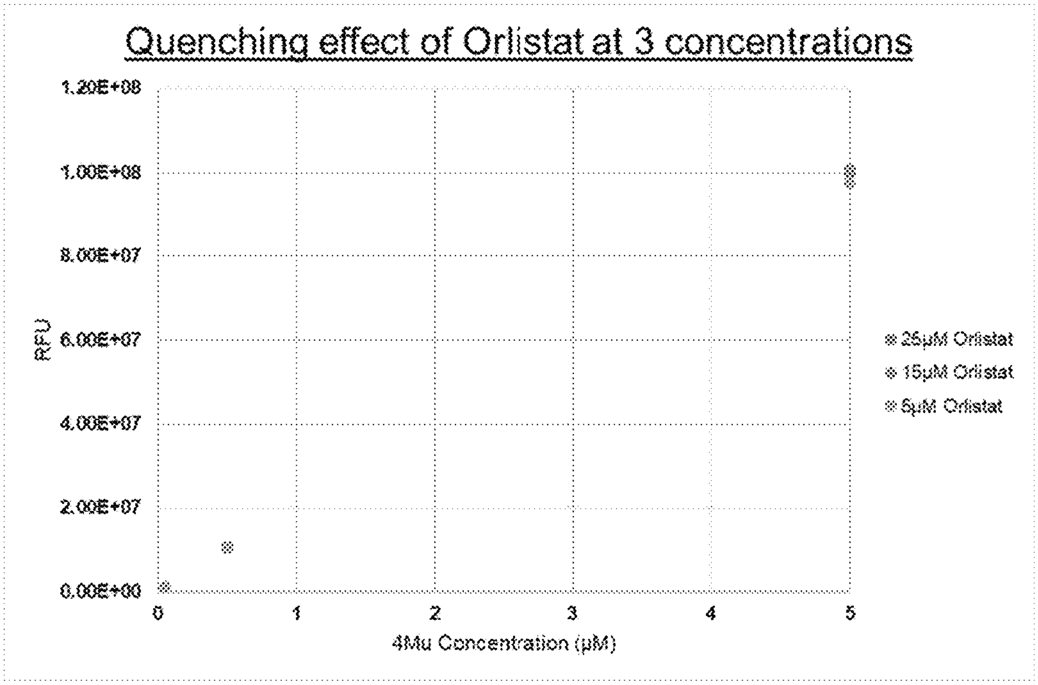
Figure 7A:
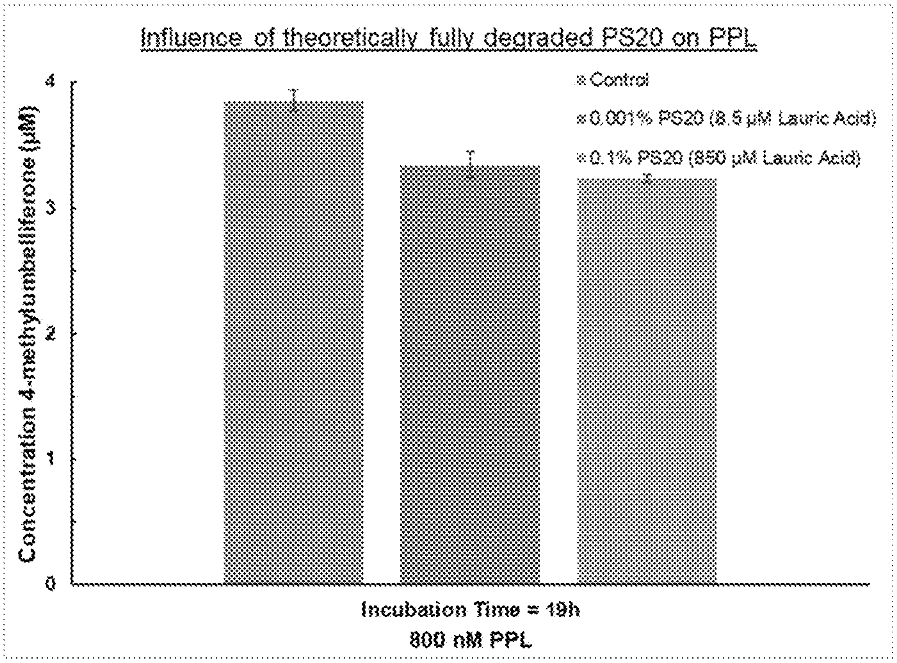
FIGS. 7A-7D relate to Example 7.
Figure 7B:
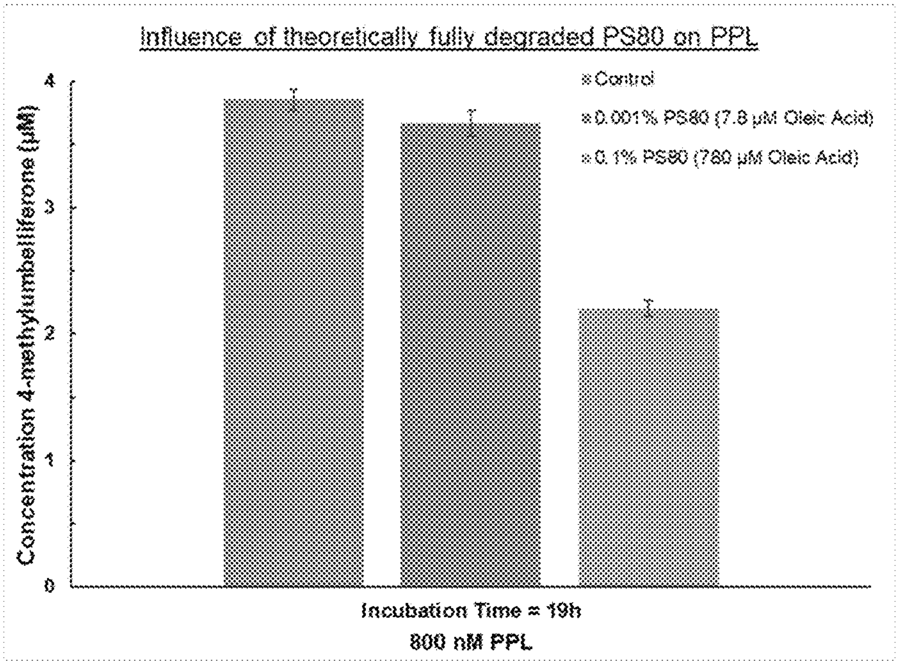
Figure 7C:
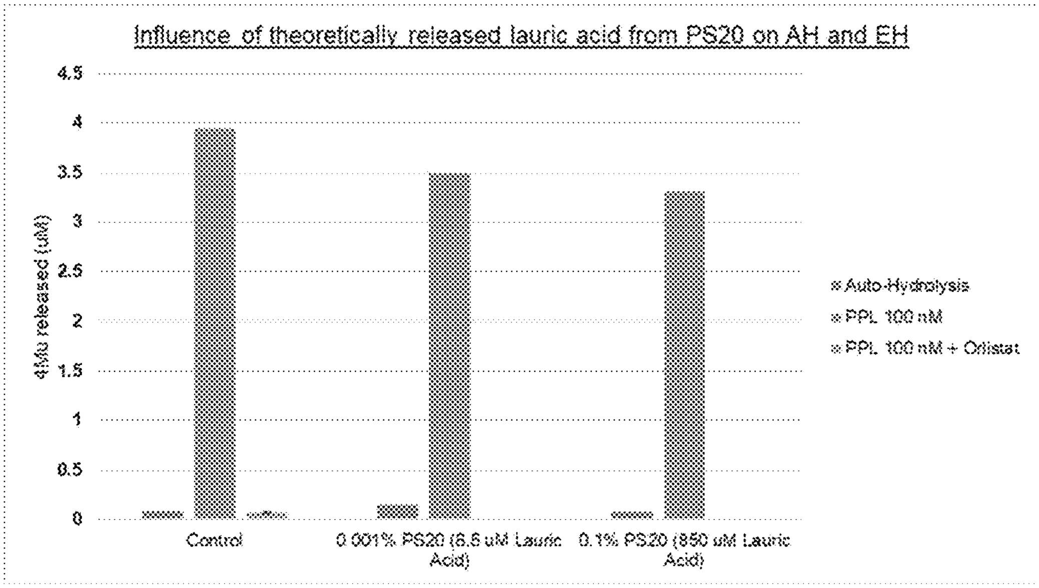
Figure 7D:
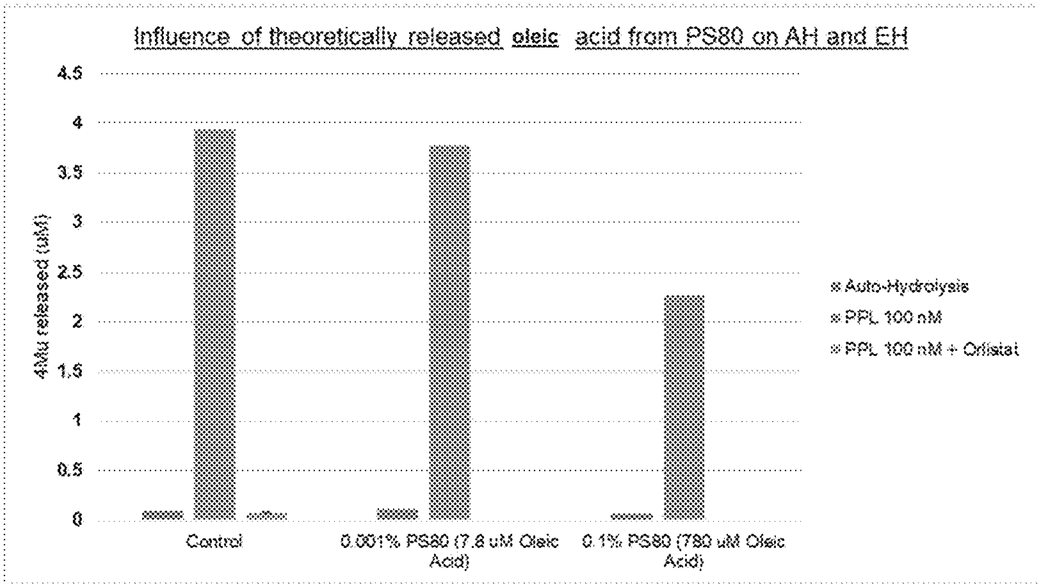

Results in FIGS. 6A-6B and Table 6 show that pre-treatment (30 minutes) with orlistat at 25 μM completely abolished lipolytic activity. Residual activity was observed with the lower orlistat concentrations. No fluorescence quenching was observed.

TABLE 6

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| Control | 0.09 | 4.40 | 4.31 |
| Co-Treatment 25 μM | / | 0.14 | 0.05 |
| Co-Treatment 15 μM | / | 0.14 | 0.06 |
| Co-Treatment 5 μM | / | 0.21 | 0.12 |
| Pre-Treatment 25 μM | / | 0.07 | 0 |
| Pre-Treatment 15 μM | / | 0.10 | 0.01 |
| Pre-Treatment 5 μM | / | 0.13 | 0.04 |

Example 6B

Lipase Assay Development VI: Lipase Inhibitor

The concentration of the lipase inhibitor orlistat was evaluated in a further experiment. Samples, HCMB composition, and experimental procedures were performed as in Example 1B. The inhibitor was prepared in MeOH at concentrations of 200, 600 and 1000 μM. For the pre-incubation experiments, the inhibitor solutions were supplemented at 2.5% (v/v) to the assay and pre-incubation for 30 min was performed. Then MeOH containing 4MuO at 200 μM was added at 2.5% (v/v) to the assay. For the co-incubation experiments, MeOH containing 100 μM 4MuO and Orlistat (100 μM, 300 μM and 500 μM) was added at 5% (v/v). High PPL concentration of 0.0335 mg/mL was used.

Three concentrations of orlistat, i.e., 5 μM, 15 μM, and 25 μM (relative to the final assay volume) were tested, with a "worst case," i.e., very high lipase concentration of 0.0335 mg/mL PPL. At these concentrations, the final assay solutions were clear and did not show turbidity due to potential insolubility of the inhibitor. Additionally, the effect on lipase activity was studied when orlistat was submitted directly to the assay with the substrate in MeOH at 5% (v/v), versus pre-addition of orlistat to the enzyme containing sample in 2.5% (v/v) of MeOH and incubation for 30 min before adding the substrate in another 2.5% (v/v) volume fraction of MeOH.

Figure 16:
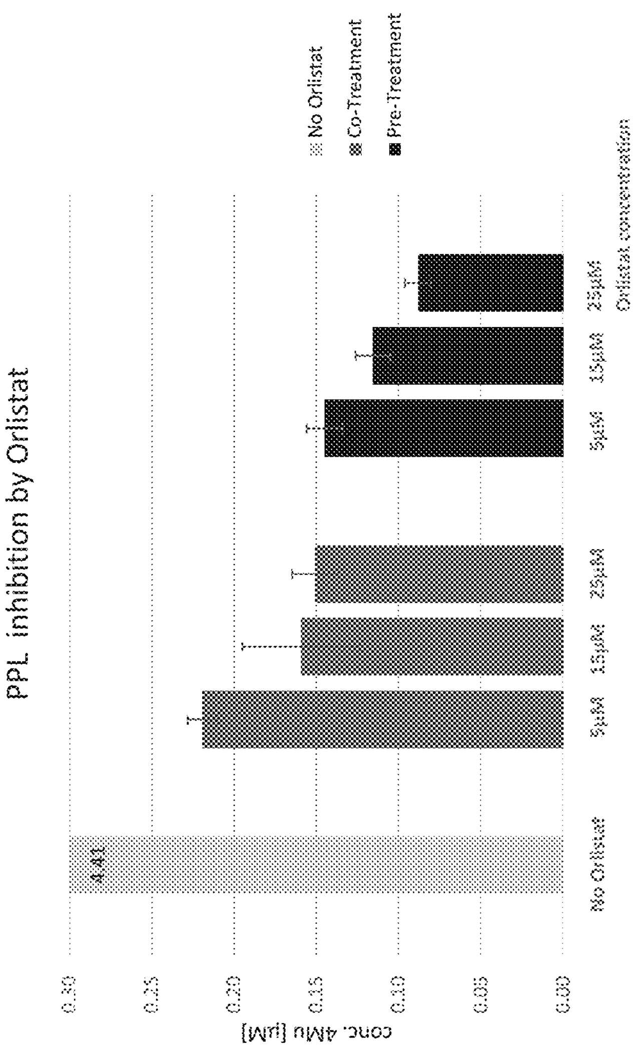
FIG. 16 relates to Example 6B.

Results of the lipase inhibitor evaluation are shown in FIG. 16. Due to the high PPL concentration as described above, 4MuO was almost completely hydrolyzed within 24 hours in the absence of orlistat. It can also be seen that orlistat inhibited PPL, and the inhibitory effect correlated with orlistat concentration, i.e., highest inhibitory effect was observed with 25 μM orlistat. Pre-incubation of the enzyme with the inhibitor had a beneficial effect, i.e. the enzyme activity at the highest tested orlistat concentration of 25 μM was reduced by ~50% in the pre-treated sample compared to the sample where substrate and inhibitor were added at the same time. Therefore, orlistat was chosen to be supplemented to the negative controls at high concentration, i.e. at 25 and the negative controls would be pre-incubated for ~30 min with the inhibitor before adding the substrate.

Example 7

Lipase Assay Development VII: Fatty Acid Product Inhibition

Fatty acid product inhibition was tested in the lipase assay using oleic acid and lauric acid, at 2 concentrations of theoretically degraded PS20 and PS80: (a) 0.1% and (b) 0.001%. In this experiment, the concentration of PPL was 800 nM.

Results in FIGS. 7A-7D and Table 7 show that the lauric acid above 8.5 μM inhibits lipase activity with no large difference between 8.5 μM and 850 μM. For oleic acid, significant product inhibition was observed at 780 μM.

TABLE 7

| Conditions (final Conc.) | Auto-Hydrolysis (AH) (μM) | Total Hydrolysis (AH + EH) (μM) | Enzymatic Hydrolysis (EH − AH) (μM) |
|---|---|---|---|
| Control | 0.09 | 3.94 | 3.85 |
| 0.001% PS20 (8.5 μM Lauric Acid) | 0.15 | 3.49 | 3.34 |
| 0.1% PS20 (850 μM Lauric Acid) | 0.08 | 3.31 | 3.23 |
| 0.001% PS80 (7.8 μM Oleic Acid) | 0.11 | 3.77 | 3.66 |
| 0.1% PS80 (780 μM Oleic Acid) | 0.06 | 2.27 | 2.21 |

Example 8

Lipase Assay Development VIII: Quenching Effects

Figure 8:
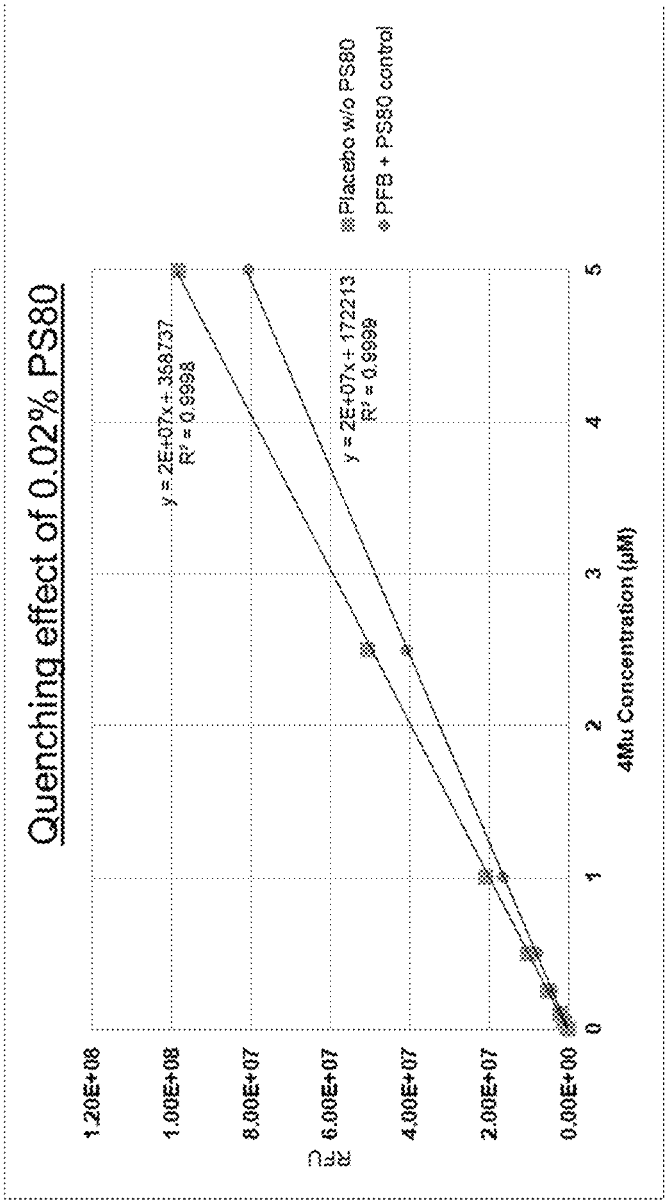
FIG. 8 relates to Example 8.

The quenching effect of polysorbate 80 was investigated. A sample containing 800 nM PPL and fresh PS80 was tested against a control with 800 nM PPL and no PS80. Results in FIG. 8 show that PS80 decreases the RFU values of each standard, suggesting a mild quenching effect.

Example 9

Lipase Assay Evaluation: CCHF

To evaluate the applicability of the assays developed in Examples 1-8 to study lipolytic activity in drug substances/drug products, the assay was evaluated at lipase concentrations that might lead to polysorbate degradation within a timeframe in which such degradation would be observed in the drug product, e.g., within 1 month.

Samples for this study contained 20 mM L-histidine at pH 6, 250 mM sucrose, the surfactants PS20 or PS80 at 0.02% (w/v), and various concentrations of CCHF (0%, 0.001%, 0.005%, 0.01%, 0.05%, 0.1%, 0.5%, 1%, 2%, all v/v). The samples were stored for 1 month at room temperature and at 2-8° C. The samples were analyzed by HPLC-FMA as described below and the lipase assay herein. For the assay positive controls the samples were supplemented with 0.055 mg/mL PPL. The HCMB contained 208 mM BIS-TRIS at pH 6, 600 mM NaCl, 5.2 mM $CaCl_2$. 5% (v/v) of the organic solvent MeOH containing 100 μM 4MuO were added to the assay. For negative controls that contained orlistat the inhibitor was prepared in MeOH at 1000 μM, and 2.5% (v/v) were supplemented to the assay and pre-incubation for 30 min was performed. Then MeOH containing 4MuO at 200 μM was added at 2.5% (v/v) to the assay. Assay components were transferred into 96 well plates and analyzed for fluorescent intensity as described for Example 1B.

The quantitative analysis of intact PS20 and PS80 was carried out using a high-performance liquid chromatography (HPLC) system (Waters Alliance e2695) equipped with an isocratic pump, an auto sampler, a knitted reactor coil (1 mL; Supelco #57410-U) and a fluorescence detector (Waters 2475 FLR Detector). Samples were injected into a mobile phase containing 5 μM N-phenyl-1-napthylamine (NPN), 15 ppm (w/v) Brij® 35 dissolved in a solution of 150 mM NaCl, 50 mM TRIS, 5% (v/v) ACN at pH 8. Fluorescence was measured at $\lambda_{ex}$=350 nm and $\lambda_{em}$=420 nm. The Empower 3 chromatographic data system (CDS) was used for peak integration and analysis.

Table 9 summarizes the samples tested:

TABLE 9

| Sample | HCMB (84 μL) | Matrix (315 μL) | MeOH (21 μL) | Comment |
|---|---|---|---|---|
| Assay positive control | HCMB containing 4 μM PPL | Authentic sample | 21 μL MeOH containing 100 μM 4MuO | |
| Assay negative control | HCMB containing 4 μM PPL | Authentic sample | 10.5 μL MeOH containing 1 mM Orlistat 10.5 μL MeOH containing 200 μM 4MuO | Pre-incubate with Orlistat for 30 min, then add 4MuO |
| Sample | HCMB | Authentic sample | 21 μL MeOH containing 100 μM 4MuO | |
| Sample negative control | HCMB | Authentic sample | 10.5 μL MeOH containing 1 mM Orlistat 10.5 μL MeOH containing 200 μM 4MuO | Pre-incubate with Orlistat for 30 min, then add 4MuO |
| Autohydrolysis | HCMB | Placebo | 10.5 μL MeOH containing 1 mM Orlistat 10.5 μL MeOH containing 200 μM 4MuO | |
| Reference standard | HCMB | Placebo | 21 μL MeOH containing 0.2-100 μM 4MU | |

Figure 9A:
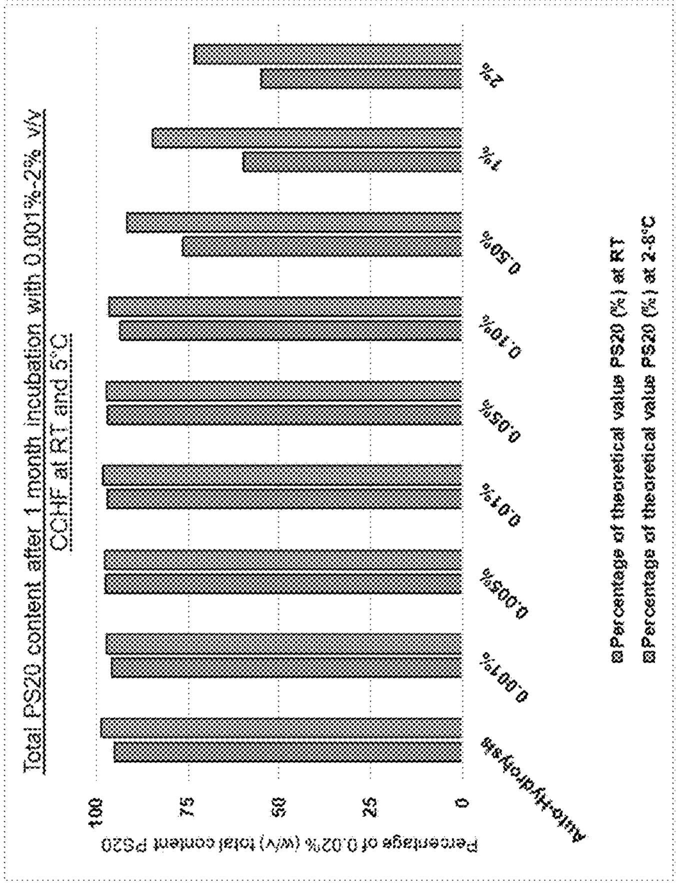
FIGS. 9A-9D relate to Example 9.
Figure 9B:
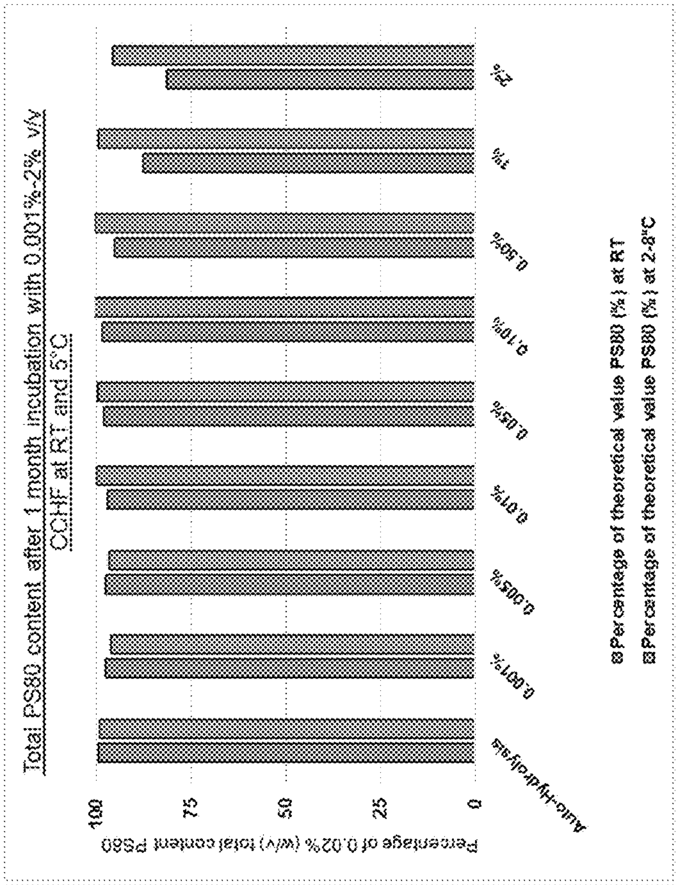

HCMB=high-concentration matrix buffer: 208 mM Bis-Tris pH 6, 600 mM NaCl, 5.2 mM $CaCl_2$ Results from the HPLC-FMA are shown in FIGS. 9A and 9B and indicate that polysorbate degradation was observed at CCHF concentrations greater than or equal to 0.10%. PS20 samples are more prone to degradation, with an effect seen at ~0.10% CCHF. Higher concentrations showed decreased apparent polysorbate concentrations. The trend was more pronounced at 25° C. compared with 2-8° C. The PS20-containing samples were apparently more prone to degradation than PS80-containing samples, where decreased signal intensity could only be detected at 0.5% CCHF. It was seen in the before described experiments on surfactant evaluation that PS80 had a slightly enhanced negative effect on lipolytic activity in CCHF containing samples compared to PS20, and therefore, as a worst case, the PS80 containing samples from the HPLC-FMA assay were subjected to the lipase assay.

Figure 9D:
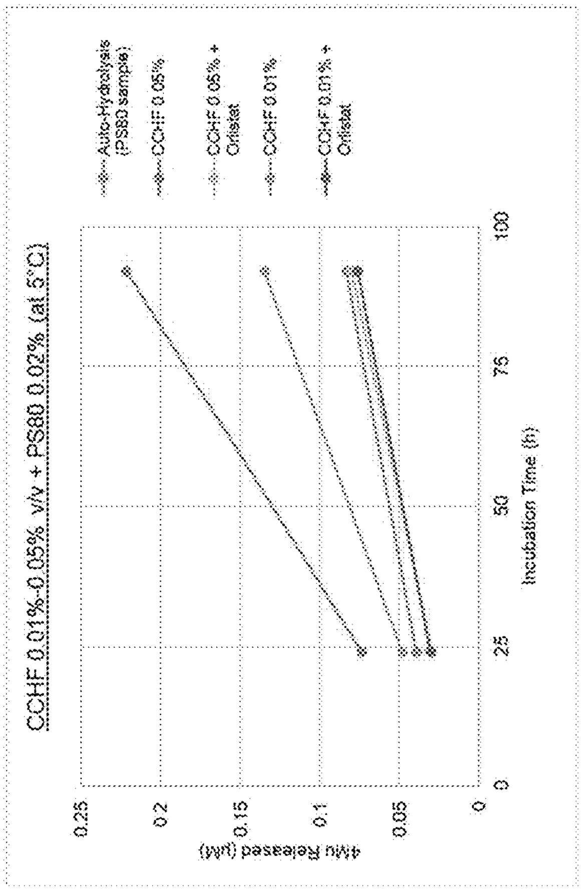
Figure 9C:
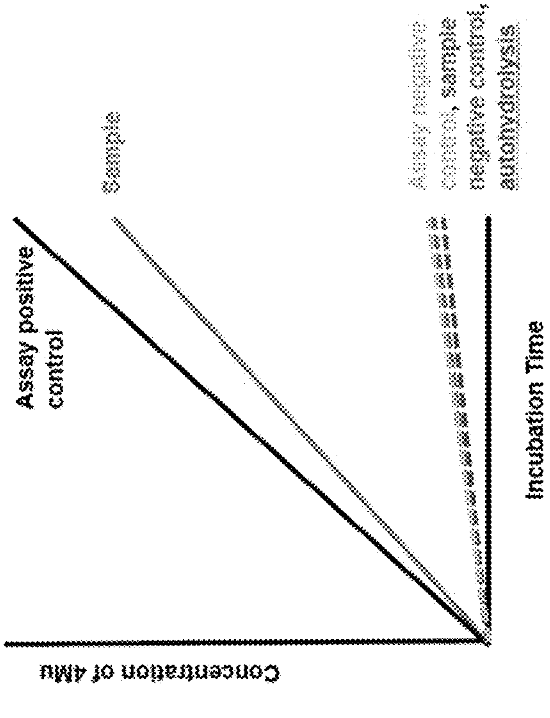
Figure 10A:
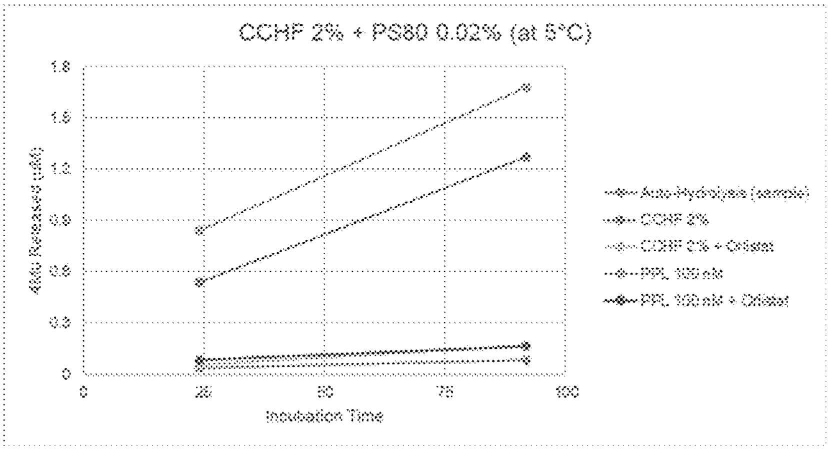
FIGS. 10A-10H relate to Example 9.
Figure 10B:
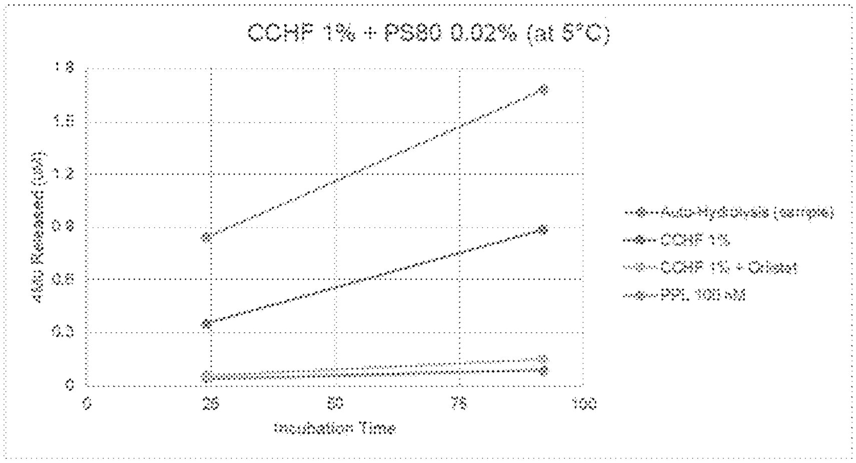
Figure 10C:
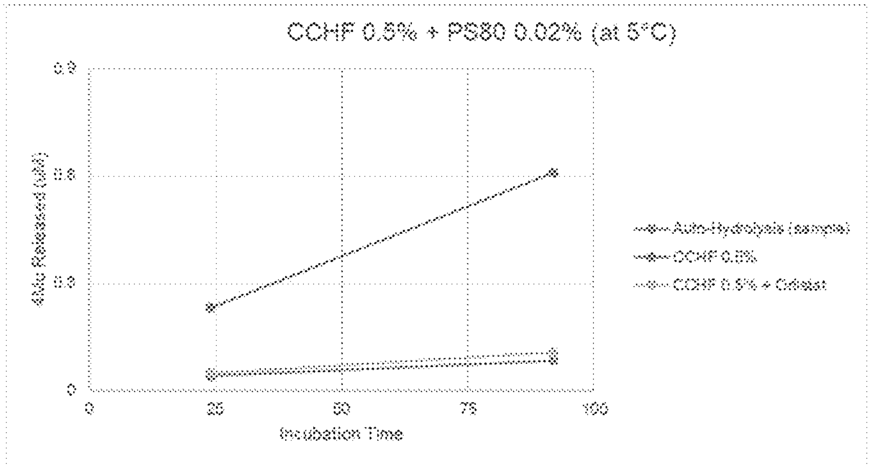
Figure 10D:
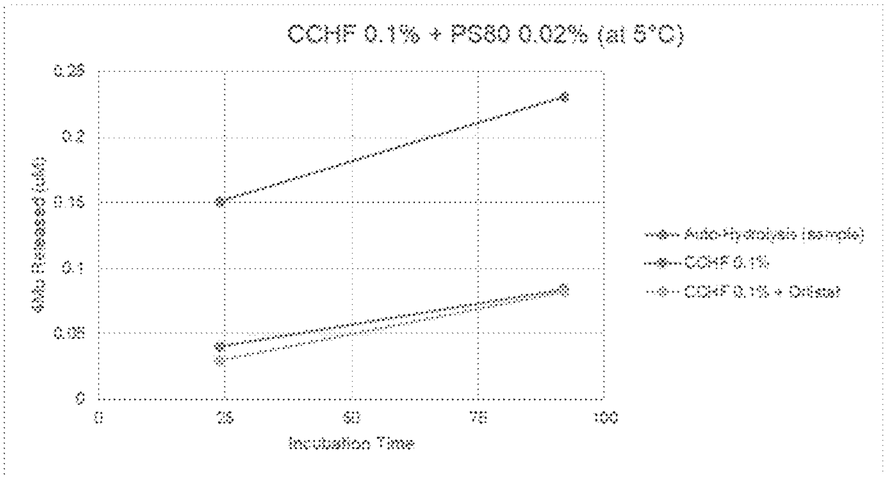
Figure 10E:
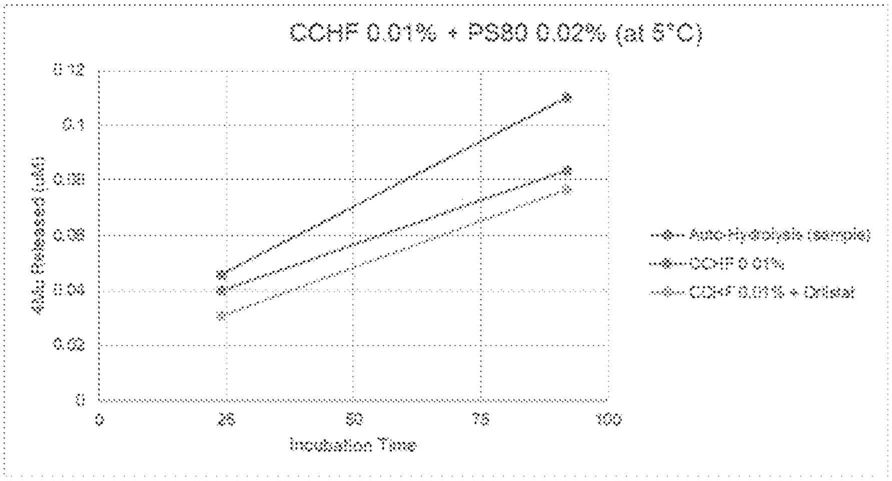
Figure 10F:
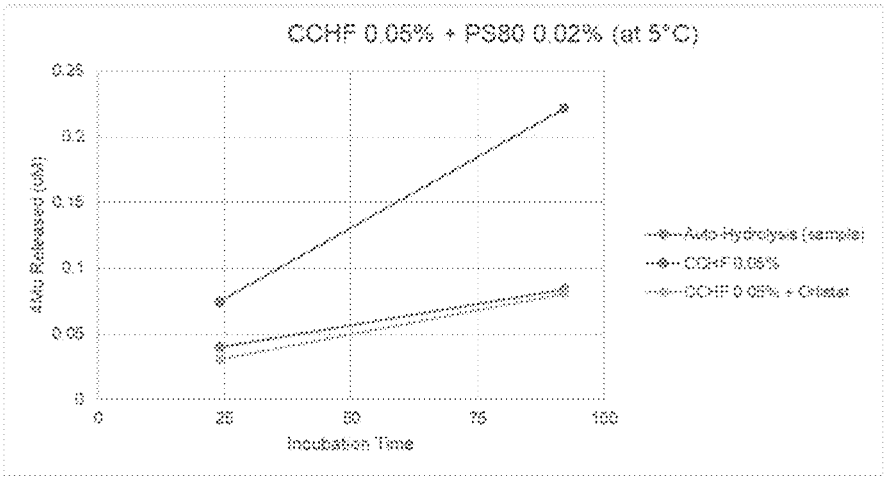
Figure 10G:
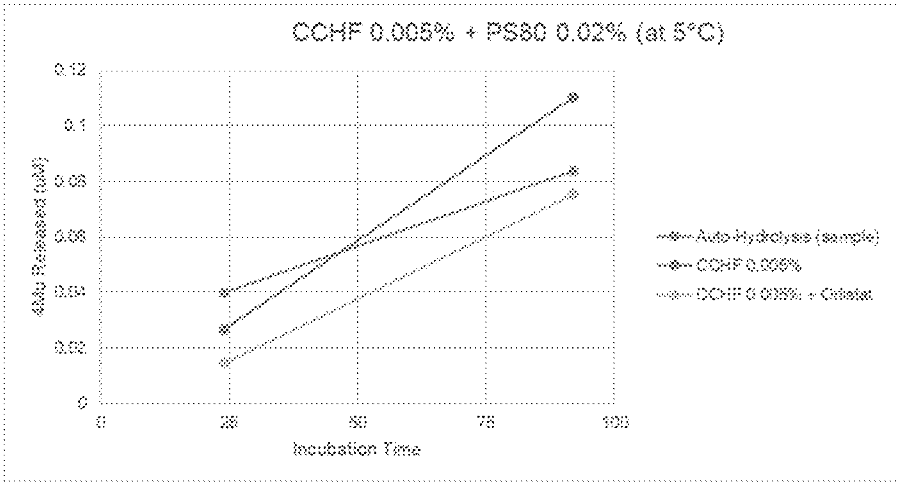
Figure 10H:
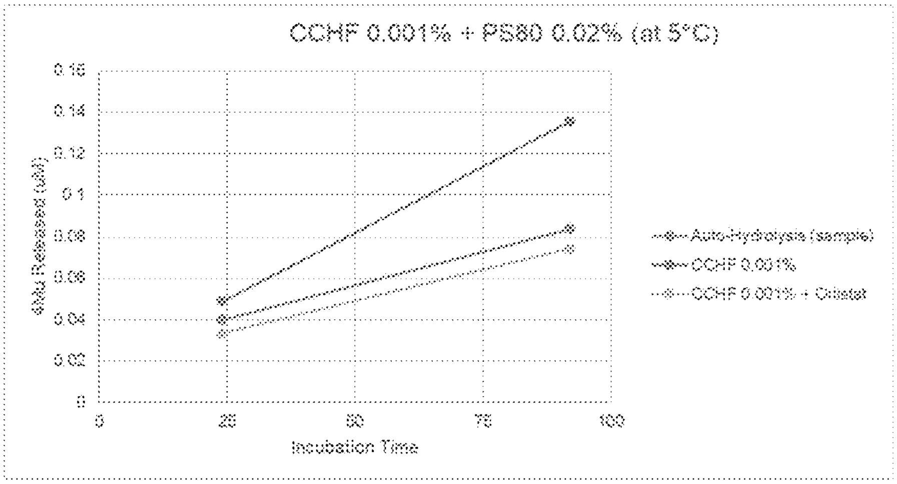

The theoretical readout of the lipase assay developed herein is shown in FIG. 9C, with the actual results shown in FIG. 9D. The actual results are comparable to the anticipated readout. The samples with CCHF at different concentrations showed 4Mu formation correlating with CCHF concentration. This enzymatic activity was higher than that of the three negative controls, i.e. autohydrolysis and the two CCHF samples spiked with orlistat. The assay was sensitive enough to detect lipase activity at concentrations where the HPLC-FMA method did not yet detect polysorbate degradation, i.e. at CCHF concentrations of <0.1%.

Additional lipase assay measurements with PS80 in different concentrations of CCHF ranging from 0.001% to 2% are shown in FIGS. 10A-10H. The indicated concentrations of CCHF and polysorbate were prior to addition of 4MuO and buffer.

Figure 18:
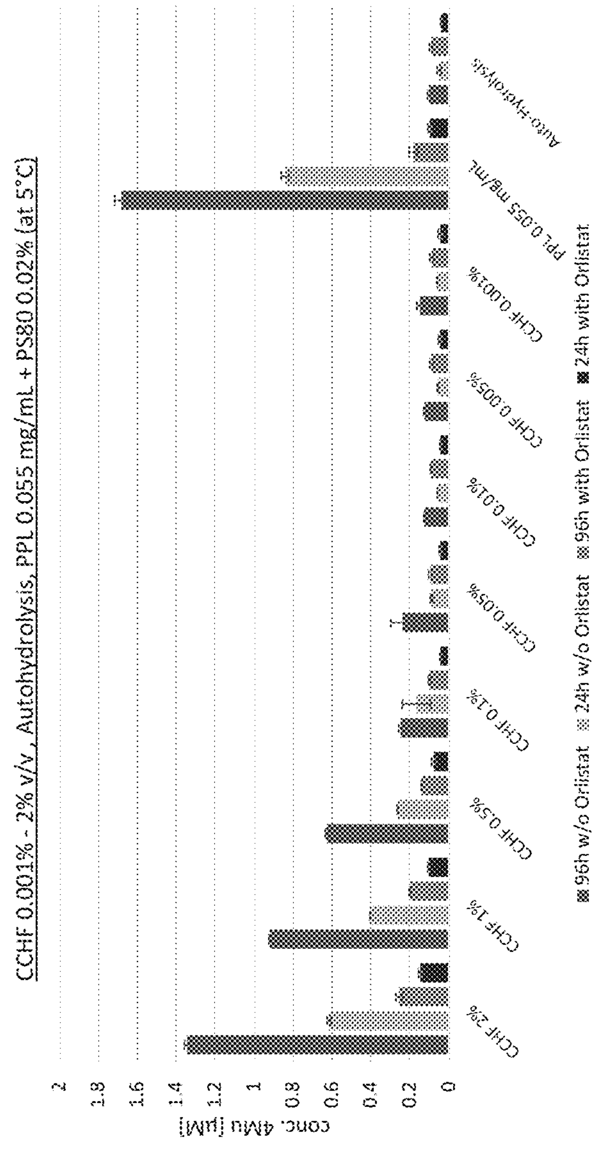
FIG. 18 relates to Example 9.

The lipase assay results are summarized in FIG. 18. The 1% CCHF sample spiked with PPL (assay positive control) showed higher activity than the one with the same CCHF concentration not spiked with PPL. 4Mu formation correlated with the concentration of CCHF, and this lipolytic activity was higher than that of the autohydrolysis and other negative controls spiked with orlistat. Most notably, the assay was sensitive enough to differentiate lipase activity from autohydrolysis and from negative controls at <0.1% CCHF concentrations, where the HPLC-FMA method did not yet detect polysorbate degradation, i.e., lipolytic activity could be detected at 0.01% and 0.05% CCHF concentration with the lipase assay.

Example 10

Lipase Assay Evaluation: Protein-Containing Formulation

The biopharmaceutical drug product formulations that can be negatively affected by lipolytic activity contain a biotherapeutic protein. The lipase assay developed in Examples 1-8 was tested with a protein-containing formulation.

The sample contained 20 mM L-histidine at pH 6, 250 mM sucrose, 0.02% PS80, 10 mg/mL mAb1 (a proprietary IgG 1), 0.5% CCHF or 0.025 mg/mL PPL. The HCMB consisted of 208 mM BIS-TRIS at pH 6, 600 mM NaCl, 5.2 mM $CaCl_2$. 5% (v/v) of the organic solvent MeOH containing 100 μM 4MuO were added to the assay. For negative controls that contained Orlistat the inhibitor was prepared in MeOH at 1000 μM, and 2.5% (v/v) were supplemented to the assay and pre-incubation for 30 min was performed. Then MeOH containing 4-MuO at 200 μM was added at 2.5% (v/v) to the assay. Assay components were transferred into 96 well plates and analyzed for fluorescent intensity as described for Example 1B. Table 10 summarizes the samples tested:

TABLE 10

| Sample/ control label | Sample/control matrix; volume ratio 75% (v/v) | HCMB; volume ratio 20% (v/v) | MeOH; volume ratio 5% (v/v) |
|---|---|---|---|
| Sample | 10 mg/mL mAb 1, 20 mM L-histidine, 250 mM sucrose, 0.02% PS80, pH 6, 0.5% CCHF | 200 mM BIS-TRIS, 600 mM NaCl, 5 mM CaCl2, pH 6 | 100 μM 4MuO |
| Sample negative | 10 mg/mL mAb 1, 20 mM L-histidine, 250 mM sucrose, 0.02% PS80, pH 6, 0.5% CCHF | 200 mM BIS-TRIS, 600 mM NaCl, 5 mM CaCl2, pH 6 | 200 μM 4MuO, 1000 μM Orlistat |
| Assay positive | 10 mg/mL mAb 1, 20 mM L-histidine, 250 mM sucrose, 0.02% PS80, pH 6, 0.5% CCHF, 0.025 mg/mL PPL | 200 mM BIS-TRIS, 600 mM NaCl, 5 mM CaCl2, pH 6 | 100 μM 4MuO |
| Assay negative | 10 mg/mL mAb 1, 20 mM L-histidine, 250 mM sucrose, 0.02% PS80, pH 6, 0.5% CCHF, 0.025 mg/mL PPL | 200 mM BIS-TRIS, 600 mM NaCl, 5 mM CaCl2, pH 6 | 200 μM 4MuO, 1000 μM Orlistat |
| Formulation positive | 20 mM L-histidine, 250 mM sucrose, 0.02% PS80, pH 6, 0.025 mg/mL PPL | 200 mM BIS-TRIS, 600 mM NaCl, 5 mM CaCl2, pH 6 | 100 μM 4MuO |
| Formulation negative | 20 mM L-histidine, 250 mM sucrose, 0.02% PS80, pH 6, 0.025 mg/mL PPL | 200 mM BIS-TRIS, 600 mM NaCl, 5 mM CaCl2, pH 6 | 200 μM 4MuO, 1000 μM Orlistat |
| Autohydrolysis | 20 mM L-histidine, 250 mM sucrose, 0.02% PS80, pH 6 | 200 mM BIS-TRIS, 600 mM NaCl, 5 mM CaCl2, pH 6 | 100 μM 4MuO |

Figure 17A:
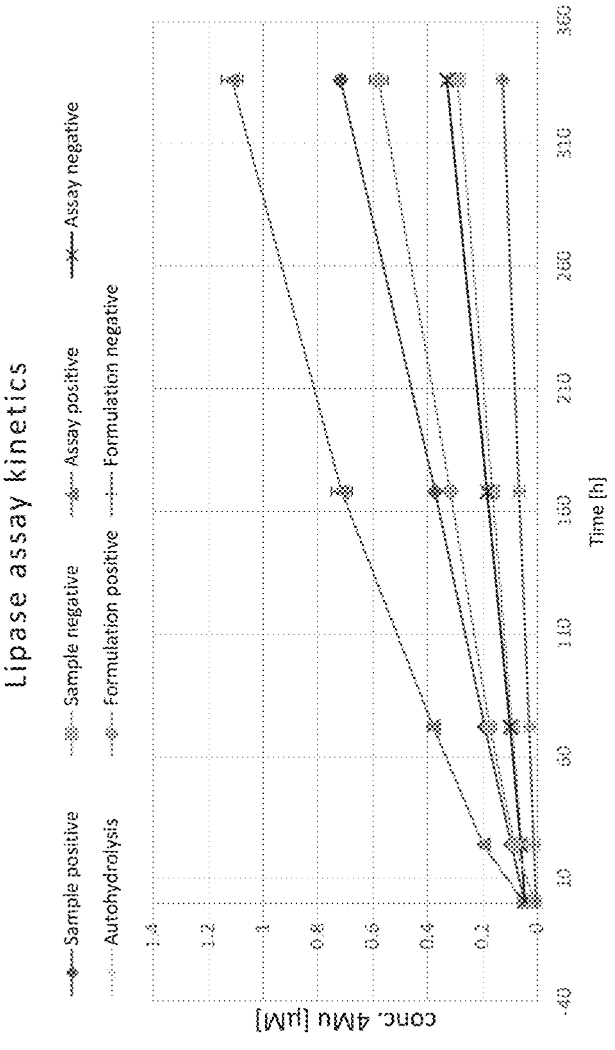
FIGS. 17A and 17B relate to Example 10.
Figure 17B:
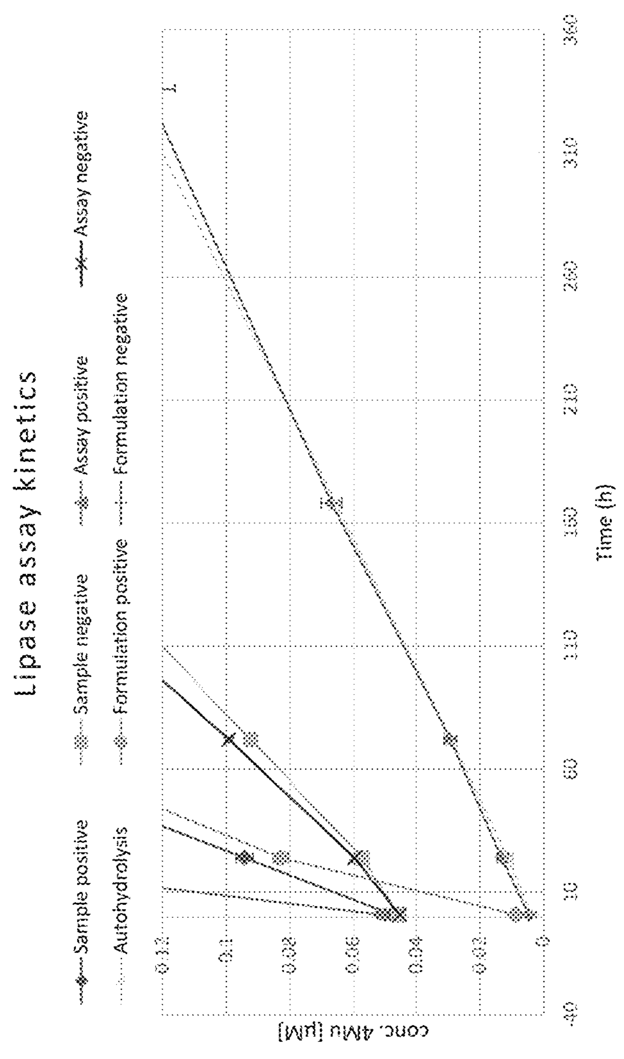

Assay results at different time points (1 h, 24 h, 72 h, 168 h, and 336 h) are shown in FIG. 17A. As expected, the assay positive control, containing both CCHF and PPL, showed the highest release of 4Mu.The assay negative control exhibited a strongly diminished activity, indicating that both PPL and the CCHF lipases were inhibited by Orlistat. The same trend can be seen for the sample and formulation positive controls (high activity), whereas sample negative control and formulation negative control were inhibited by Orlistat (low activity). Autohydrolysis control and the formulation negative control show at all timepoints similar readouts, that cannot be differentiated in FIG. 17A. FIG. 17B, showing a zoom of the negative controls, illustrates that the activity in both of the negative controls is similar.

An offset can be observed in the apparent activity of the assay/sample negative controls compared to autohydrolysis/formulation negative control. The same offset was observed in a blank sample containing no substrate (data not shown), indicating that the protein containing sample already has fluorescence response independent from 4Mu. Over the timeframe where lipolytic activity was studied, i.e. within 336 h, the offset increased, indicating that the initially inhibited lipases in CCHF and PPL were slowly reactivated, although apparently not in the formulation negative.

Lookene et al. previously reported that orlistat is not only a mechanism based inhibitor, but rather a true substrate for lipoprotein lipase, with fast inhibition, i.e. formation of the covalent enzyme-orlistat-complex at the active site serine, and slow hydrolysis of this complex (see, e.g., Lookene et al., "Interactions of lipoprotein lipase with the active-site inhibitor tetrahydrolipstatin (Orlistat)R," *Eur J Biochem.* 1994; 222:395-403). For the present assay and its application for the evaluation of lipolytic activity in drug substances/drug products, this is of relevance: if the culprits (e.g., lipolytic enzymes) that are part of the residual fraction of HCPs in drug substances/drug products, and that are responsible for degradation of polysorbate, can be inhibited by orlistat, they might be reactivated. If a differentiation of lipolytic activity between sample and sample negative control is not possible, this might be indicative for either low lipolytic activity in the sample, or for the presence of lipolytic enzymes that cannot be inhibited by orlistat. In the first case, if the 4Mu formation is not much increased compared to the autohydrolysis control, this indicates low lipolytic activity and low risk of polysorbate degradation in the drug substance/drug product. If high 4Mu formation is seen in the sample, as compared to autohydrolysis, this indicates that lipolytic enzymes are present, but cannot be inhibited by orlistat.

All references cited herein, including patents, patent applications, papers, textbooks and the like, and the references cited therein, to the extent that they are not already, are hereby incorporated herein by reference in their entirety.

What is claimed is:

1. A method of detecting lipolytic activity in an aqueous assay sample, the method comprising a. combining the aqueous assay sample comprising a protein preparation, wherein the protein preparation comprises a therapeutic protein that does not have lipolytic activity, with an organic solvent comprising 4-methylumbelliferyl oleate (4MuO); and b. measuring the formation of oleate and 4-methylumbelliferone (4Mu) by fluorescence.

2. A method of determining stability of a protein preparation, comprising a. combining an aqueous assay sample comprising the protein preparation, wherein the protein preparation comprises a therapeutic protein that does not have lipolytic activity, with an organic solvent comprising 4-methylumbelliferyl oleate (4MuO);

b. measuring the formation of oleate and 4-methylumbelliferone (4Mu) by fluorescence; and c. determining the stability of the protein preparation based on the measured fluorescence.

3. A composition comprising:

a. an aqueous assay sample comprising a protein preparation, wherein the protein preparation comprises a therapeutic protein that does not have lipolytic activity; and b. an organic solvent, wherein the organic solvent further comprises 4-methylumbelliferyl oleate (4MuO), wherein the aqueous assay sample has a pH of 5.0 to 6.9, and wherein the aqueous assay sample is about 80% to about 99.9% of the composition, and the organic solvent is about 0.1% to about 20% of the composition.

4. The composition of claim 3, wherein the protein preparation is a cell culture supernatant.

5. The composition of claim 3, wherein the protein preparation is a partially purified protein preparation.

6. The composition of claim 3, wherein the protein preparation is a purified protein preparation.

7. The composition of claim 3, wherein the protein preparation comprises a surfactant.

8. The composition of claim 7, wherein the surfactant is a polysorbate.

9. The composition of claim 8, wherein the polysorbate is polysorbate-20, polysorbate-80 or combinations thereof.

10. The composition of claim 3, wherein the protein preparation further comprises an additional host cell protein.

11. The composition of claim 3, wherein the aqueous assay sample further comprises a buffering agent, a salt, or both.

12. The composition of claim 11, wherein the salt is sodium chloride, calcium chloride or combinations thereof.

13. The composition of claim 12, wherein the sodium chloride is about 50 mM to about 400 mM in the aqueous assay sample.

14. The composition of claim 12, wherein the calcium chloride is about 0.2 mM to about 10 mM in the aqueous assay sample.

15. The composition of claim 11, wherein the buffering agent is Tris or Bis-Tris.

16. The composition of claim 11, wherein the buffering agent is about 2 mM to about 200 mM in the aqueous assay sample.

17. The composition of claim 3, wherein the organic solvent is an alcohol, a sulfoxide, a nitrile, or combination thereof.

18. The composition of claim 3, wherein the composition further comprises a lipase inhibitor.

19. The composition of claim 18, wherein the lipase inhibitor is(S)-2-formylamino-4-methyl-pentanoic acid(S)-1-[[(2S, 3S)-3-hexyl-4-oxo-2-oxetanyl] methyl]-dodecyl ester (orlistat).

20. The composition of claim 18, wherein the lipase inhibitor is in the organic solvent.

21. The composition of claim 6, wherein:

the aqueous assay sample is about 90% to about 99.9% (vol/vol) of the composition, wherein the aqueous assay sample comprises i. the purified protein preparation and a lipid;

ii. a buffering agent;

iii. about 1.0 mM to about 2.0 mM calcium chloride; and iv. about 100 mM to about 200 mM sodium chloride; and the organic solvent is about 0.1% to about 10% (vol/vol) of the composition, wherein the organic solvent is selected from methanol, ethanol, propanol, iso-propanol, butanol, sec-butanol, iso-butanol, tert-butanol, dimethyl sulfoxide (DMSO), acetonitrile, or combinations thereof; and the aqueous assay sample has a pH of 5.0 to 6.9.

22. The composition of claim 3, wherein the aqueous assay sample has a pH of about 5.5 to about 6.5.

* * * * *